United States Patent
Takáts et al.

(10) Patent No.: US 10,777,397 B2
(45) Date of Patent: Sep. 15, 2020

(54) INLET INSTRUMENTATION FOR ION ANALYSER COUPLED TO RAPID EVAPORATIVE IONISATION MASS SPECTROMETRY ("REIMS") DEVICE

(71) Applicant: Micromass UK Limited, Wilmslow (GB)

(72) Inventors: Zoltán Takáts, Cambridge (GB); Júlia Balog, Solymar (HU); Steven Derek Pringle, Darwen (GB); Tamás Karancsi, Budapest (HU); Michael Raymond Morris, Derbyshire (GB); Lajos Gödörhazy, Erd (HU); Dániel Szalay, Budapest (HU); Dániel Simon, Morichida (HU)

(73) Assignee: Micromass UK Limited, Wilmslow (GB)

( * ) Notice: Subject to any disclaimer, the term of this patent is extended or adjusted under 35 U.S.C. 154(b) by 322 days.

(21) Appl. No.: 15/555,720

(22) PCT Filed: Mar. 7, 2016

(86) PCT No.: PCT/GB2016/050620
§ 371 (c)(1),
(2) Date: Sep. 5, 2017

(87) PCT Pub. No.: WO2016/142690
PCT Pub. Date: Sep. 15, 2016

(65) Prior Publication Data
US 2018/0059119 A1    Mar. 1, 2018

(30) Foreign Application Priority Data

Mar. 6, 2015  (GB) .................................. 1503863.1
Mar. 6, 2015  (GB) .................................. 1503864.9

(Continued)

(51) Int. Cl.
*H01J 49/04*  (2006.01)
*A61B 1/04*  (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
None
See application file for complete search history.

(56) References Cited

U.S. PATENT DOCUMENTS 3,479,545 A    11/1969  Wilson
3,770,954 A    11/1973  Davis
(Continued)

FOREIGN PATENT DOCUMENTS

CA    2882003 A1    2/2014
CN    101170043 A    4/2008
(Continued)

OTHER PUBLICATIONS

Agar, Nathalie et al., "*Development of Stereotactic Mass Spectrometry for Brain Tumor Surgery*", Biosis, Neurosurgery Online, vol. 68, No. 2, (2011).
(Continued)

*Primary Examiner* — Xiaoyun R Xu

(57) ABSTRACT

An apparatus is disclosed comprising a first device for generating aerosol, smoke or vapour from one or more regions of a target, an inlet conduit to an ion analyser or mass spectrometer, the inlet conduit having an inlet through which the aerosol, smoke or vapour passes, and a Venturi pump arrangement arranged and adapted to direct the aerosol, smoke or vapour towards the inlet.

16 Claims, 31 Drawing Sheets

(30) Foreign Application Priority Data

| Mar. 6, 2015 | (GB) | 1503867.2 |
|---|---|---|
| Mar. 6, 2015 | (GB) | 1503876.3 |
| Mar. 6, 2015 | (GB) | 1503877.1 |
| Mar. 6, 2015 | (GB) | 1503878.9 |
| Mar. 6, 2015 | (GB) | 1503879.7 |
| Sep. 9, 2015 | (GB) | 1516003.9 |
| Oct. 16, 2015 | (GB) | 1518369.2 |

(51) Int. Cl.

| A61B 1/273 | (2006.01) |
|---|---|
| A61B 5/00 | (2006.01) |
| A61B 5/01 | (2006.01) |
| A61B 5/055 | (2006.01) |
| A61B 5/05 | (2006.01) |
| A61B 6/03 | (2006.01) |
| A61B 8/13 | (2006.01) |
| A61B 10/00 | (2006.01) |
| A61B 10/02 | (2006.01) |
| A61B 17/00 | (2006.01) |
| A61B 17/32 | (2006.01) |
| A61B 18/00 | (2006.01) |
| A61B 18/04 | (2006.01) |
| A61B 18/14 | (2006.01) |
| A61B 18/18 | (2006.01) |
| A61B 18/20 | (2006.01) |
| A61B 90/13 | (2016.01) |
| A61F 13/38 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 3/00 | (2006.01) |
| G01N 9/00 | (2006.01) |
| G01N 27/62 | (2006.01) |
| G01N 30/72 | (2006.01) |
| G01N 33/487 | (2006.01) |
| G01N 33/68 | (2006.01) |
| G01N 33/92 | (2006.01) |
| H01J 49/00 | (2006.01) |
| H01J 49/02 | (2006.01) |
| H01J 49/06 | (2006.01) |
| H01J 49/10 | (2006.01) |
| H01J 49/14 | (2006.01) |
| H01J 49/16 | (2006.01) |
| H01J 49/24 | (2006.01) |
| H01J 49/26 | (2006.01) |
| A61B 1/00 | (2006.01) |
| A61B 1/31 | (2006.01) |
| A61B 5/145 | (2006.01) |
| G16B 20/00 | (2019.01) |
| G16H 10/40 | (2018.01) |
| G16H 15/00 | (2018.01) |
| G16H 20/40 | (2018.01) |
| G16H 50/20 | (2018.01) |
| G16H 70/60 | (2018.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/622* (2013.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/044* (2013.01); *H01J 49/0404* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 20/40* (2018.01); *G16H 50/20* (2018.01); *G16H 70/60* (2018.01)

(56) References Cited

U.S. PATENT DOCUMENTS

| H000414 H | 1/1988 | Young et al. |
|---|---|---|
| 4,835,383 A | 5/1989 | Mahoney et al. |
| 4,845,367 A | 7/1989 | Amirav et al. |
| 4,883,958 A | 11/1989 | Vestal |
| 4,935,624 A | 6/1990 | Henion et al. |
| 5,033,541 A | 7/1991 | O'Silva |
| 5,053,343 A | 10/1991 | Vora et al. |
| 5,257,991 A | 11/1993 | Fletcher et al. |
| 5,308,977 A | 5/1994 | Oishi et al. |
| 5,374,755 A | 12/1994 | Neue et al. |
| 5,454,274 A | 10/1995 | Zhu |
| 5,509,916 A | 4/1996 | Taylor |
| 5,559,326 A | 9/1996 | Goodley et al. |
| 5,800,597 A | 9/1998 | Perrotta et al. |
| 5,828,062 A | 10/1998 | Jarrell et al. |
| 5,830,214 A | 11/1998 | Flom et al. |
| 5,836,909 A | 11/1998 | Cosmescu |
| 5,969,352 A | 10/1999 | French et al. |
| 5,989,015 A | 11/1999 | Guerin et al. |
| 6,032,673 A | 3/2000 | Savage et al. |
| 6,333,632 B1 | 12/2001 | Yang et al. |
| 6,348,688 B1 | 2/2002 | Vestal |
| 6,825,464 B2 | 11/2004 | De La Mora |

(56) References Cited

U.S. PATENT DOCUMENTS

| | | |
|---|---|---|
| 6,998,622 B1 | 2/2006 | Wang et al. |
| 7,238,936 B2 | 7/2007 | Okamura et al. |
| 7,247,845 B1 | 7/2007 | Gebhardt et al. |
| 7,329,253 B2 | 2/2008 | Brounstein et al. |
| 7,335,897 B2 | 2/2008 | Takats et al. |
| 7,365,309 B2 | 4/2008 | Denny et al. |
| 7,517,348 B2 | 4/2009 | Vetter et al. |
| 7,564,028 B2 | 7/2009 | Vestal |
| 7,718,958 B2 | 5/2010 | Shiea et al. |
| 7,828,948 B1 | 11/2010 | Hatch et al. |
| 7,947,039 B2 | 5/2011 | Santor |
| 7,960,711 B1 | 6/2011 | Sheehan et al. |
| 8,156,151 B2 | 4/2012 | Sidman |
| 8,193,487 B2 | 6/2012 | Briglin et al. |
| 8,232,520 B2 | 7/2012 | Cristoni |
| 8,253,098 B2 | 8/2012 | Hiraoka et al. |
| 8,286,260 B2 | 10/2012 | Vertes et al. |
| 8,314,382 B2 | 11/2012 | Takats |
| 8,334,504 B2 | 12/2012 | Finlay et al. |
| 8,431,409 B1 | 4/2013 | Meinhart et al. |
| 8,448,493 B2 | 5/2013 | McIntyre et al. |
| 8,481,922 B2 | 7/2013 | Musselman |
| 8,778,695 B2 | 7/2014 | Caprioli |
| 8,803,085 B2 | 8/2014 | Ouyang et al. |
| 8,834,462 B2 | 9/2014 | Johnson et al. |
| 8,970,840 B2 | 3/2015 | Kulkarni et al. |
| 9,046,448 B2 | 6/2015 | Takats |
| 9,053,914 B2 | 6/2015 | Pringle et al. |
| 9,082,603 B2 | 7/2015 | Bajic |
| 9,120,083 B2 | 9/2015 | Wyndham et al. |
| 9,255,907 B2 | 2/2016 | Heanue et al. |
| 9,281,174 B2 | 3/2016 | Takats |
| 9,287,100 B2 | 3/2016 | Szalay et al. |
| 9,709,529 B2 | 7/2017 | Takats |
| 9,731,219 B2 | 8/2017 | Wang et al. |
| 9,947,524 B2 | 4/2018 | Pringle et al. |
| 10,186,626 B2 | 1/2019 | Song et al. |
| 2002/0008871 A1 | 1/2002 | Poustka et al. |
| 2002/0070338 A1 | 6/2002 | Loboda |
| 2002/0076824 A1 | 6/2002 | Haglund et al. |
| 2003/0001084 A1 | 1/2003 | Bateman et al. |
| 2003/0008404 A1 | 1/2003 | Tomita et al. |
| 2003/0015657 A1 | 1/2003 | Takada et al. |
| 2003/0042412 A1 | 3/2003 | Park |
| 2003/0080278 A1 | 5/2003 | Okada et al. |
| 2003/0119193 A1 | 6/2003 | Hess et al. |
| 2003/0135222 A1 | 7/2003 | Baska |
| 2003/0136918 A1 | 7/2003 | Hartley |
| 2003/0193023 A1 | 10/2003 | Marsh |
| 2004/0007673 A1 | 1/2004 | Coon et al. |
| 2004/0079881 A1 | 4/2004 | Fischer et al. |
| 2004/0124352 A1 | 7/2004 | Kashima et al. |
| 2004/0197899 A1 | 10/2004 | Gomez et al. |
| 2004/0217274 A1 | 11/2004 | Bai et al. |
| 2004/0235395 A1 | 11/2004 | Hashish et al. |
| 2005/0017091 A1 | 1/2005 | Olsen et al. |
| 2005/0032471 A1 | 2/2005 | Pfarr et al. |
| 2005/0061779 A1 | 3/2005 | Blumenfeld |
| 2005/0067565 A1 | 3/2005 | Takada et al. |
| 2005/0072916 A1 | 4/2005 | Park |
| 2005/0074361 A1 | 4/2005 | Tanoshima et al. |
| 2005/0077644 A1 | 4/2005 | Bryan et al. |
| 2005/0124986 A1 | 6/2005 | Brounstein et al. |
| 2005/0138861 A1 | 6/2005 | O'Connor |
| 2005/0154490 A1 | 7/2005 | Blaine et al. |
| 2005/0159765 A1 | 7/2005 | Moutafis et al. |
| 2005/0178962 A1 | 8/2005 | Guevremont et al. |
| 2005/0178975 A1 | 8/2005 | Glukhoy |
| 2005/0230634 A1 | 10/2005 | Bajic et al. |
| 2005/0230635 A1 | 10/2005 | Takats et al. |
| 2005/0258358 A1 | 11/2005 | Thakur |
| 2005/0269518 A1 | 12/2005 | Bajic et al. |
| 2005/0274885 A1 | 12/2005 | Brown et al. |
| 2006/0035570 A1 | 2/2006 | Chisum et al. |
| 2006/0054806 A1 | 3/2006 | Yamada et al. |
| 2006/0091308 A1 | 5/2006 | Boyle et al. |
| 2006/0097084 A1 | 5/2006 | Gromer et al. |
| 2006/0108539 A1 | 5/2006 | Franzen |
| 2006/0113463 A1 | 6/2006 | Rossier et al. |
| 2006/0122593 A1 | 6/2006 | Jun |
| 2006/0138321 A1 | 6/2006 | Ahem et al. |
| 2006/0145089 A1 | 7/2006 | Cristoni et al. |
| 2006/0186334 A1 | 8/2006 | Jolliffe et al. |
| 2006/0250138 A1 | 11/2006 | Sparkman et al. |
| 2006/0255264 A1 | 11/2006 | Belford |
| 2007/0023631 A1 | 2/2007 | Takats et al. |
| 2007/0023677 A1 | 2/2007 | Perkins et al. |
| 2007/0094389 A1 | 4/2007 | Nussey et al. |
| 2007/0114394 A1 | 5/2007 | Combs et al. |
| 2007/0114437 A1 | 5/2007 | Kovtoun |
| 2007/0176113 A1 | 8/2007 | Shiea et al. |
| 2007/0181802 A1 | 8/2007 | Yamada et al. |
| 2008/0001081 A1 | 1/2008 | Jindai et al. |
| 2008/0015278 A1 | 1/2008 | Malik et al. |
| 2008/0042056 A1 | 2/2008 | Fischer et al. |
| 2008/0067352 A1 | 3/2008 | Wang |
| 2008/0073503 A1 | 3/2008 | Wu |
| 2008/0073512 A1 | 3/2008 | Siuzdak et al. |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0312651 A1 | 12/2008 | Pope et al. |
| 2009/0065714 A1 | 3/2009 | Keady |
| 2009/0082637 A1 | 3/2009 | Galperin |
| 2009/0126891 A1 | 5/2009 | Koivunen et al. |
| 2009/0159790 A1 | 6/2009 | Kostiainen et al. |
| 2009/0272893 A1 | 11/2009 | Hieftje et al. |
| 2009/0302211 A1 | 12/2009 | Takats |
| 2010/0012830 A1 | 1/2010 | Cristoni |
| 2010/0072359 A1 | 3/2010 | Briglin et al. |
| 2010/0078550 A1 | 4/2010 | Wiseman et al. |
| 2010/0101304 A1 | 4/2010 | McIntyre et al. |
| 2010/0176290 A1 | 7/2010 | Vidal-de-Miguel |
| 2010/0186524 A1 | 7/2010 | Ariessohn et al. |
| 2010/0229263 A1 | 9/2010 | Vertes et al. |
| 2011/0036978 A1 | 2/2011 | Franzen |
| 2011/0049352 A1 | 3/2011 | Ding et al. |
| 2011/0059554 A1 | 3/2011 | Albers et al. |
| 2011/0087308 A1 | 4/2011 | Morgan |
| 2011/0121173 A1 | 5/2011 | Koenig et al. |
| 2011/0295250 A1 | 12/2011 | Johnson et al. |
| 2012/0018628 A1 | 1/2012 | Wuijckhuijse et al. |
| 2012/0048264 A1 | 3/2012 | Finlay et al. |
| 2012/0074306 A1 | 3/2012 | Jesse et al. |
| 2012/0079894 A1 | 4/2012 | Van Berkel et al. |
| 2012/0080592 A1 | 4/2012 | Wiseman et al. |
| 2012/0085649 A1 | 4/2012 | Sano et al. |
| 2012/0119079 A1 | 5/2012 | Ouyang et al. |
| 2012/0149009 A1 | 6/2012 | Levis et al. |
| 2012/0156712 A1 | 6/2012 | Takats |
| 2012/0295276 A1 | 11/2012 | Cooks et al. |
| 2013/0178845 A1 | 7/2013 | Smith et al. |
| 2013/0181126 A1 | 7/2013 | Jong |
| 2013/0303846 A1 | 11/2013 | Cybulski et al. |
| 2014/0151547 A1 | 6/2014 | Bajic |
| 2014/0276775 A1 | 9/2014 | Funk et al. |
| 2014/0291506 A1 | 10/2014 | Tikhonski |
| 2014/0297201 A1 | 10/2014 | Knorr et al. |
| 2014/0299577 A1 | 10/2014 | Chung |
| 2014/0326865 A1 | 11/2014 | Pringle et al. |
| 2014/0353488 A1 | 12/2014 | Takats |
| 2014/0353489 A1 | 12/2014 | Szalay et al. |
| 2015/0021469 A1 | 1/2015 | Bajic |
| 2015/0048255 A1 | 2/2015 | Jarrell |
| 2015/0192590 A1 | 7/2015 | Sodeoka et al. |
| 2015/0201913 A1 | 7/2015 | Takats |
| 2016/0002696 A1 | 1/2016 | Galiano |
| 2016/0133450 A1 | 5/2016 | Green et al. |
| 2016/0215322 A1 | 7/2016 | Goodlett et al. |
| 2016/0247668 A1 | 8/2016 | Szalay et al. |
| 2016/0341712 A1 | 11/2016 | Agar |

(56) References Cited

U.S. PATENT DOCUMENTS

| | | |
|---|---|---|
| 2016/0372313 A1 | 12/2016 | Brown et al. |
| 2017/0103880 A1 | 4/2017 | Syage |
| 2018/0136091 A1 | 5/2018 | Ryan et al. |

FOREIGN PATENT DOCUMENTS

| | | |
|---|---|---|
| CN | 101223625 A | 7/2008 |
| CN | 101288146 A | 10/2008 |
| CN | 101413905 A | 4/2009 |
| CN | 101490524 A | 7/2009 |
| CN | 201266145 Y | 7/2009 |
| CN | 101657158 A | 2/2010 |
| CN | 101819179 A | 9/2010 |
| CN | 101871914 A | 10/2010 |
| CN | 102026709 A | 4/2011 |
| CN | 102121921 A | 7/2011 |
| CN | 102137618 A | 7/2011 |
| CN | 102164675 A | 8/2011 |
| CN | 102264404 A | 11/2011 |
| CN | 102367424 A | 3/2012 |
| CN | 102445544 A | 5/2012 |
| CN | 102483369 A | 5/2012 |
| CN | 102800553 A | 11/2012 |
| CN | 102879453 A | 1/2013 |
| CN | 102924993 A | 2/2013 |
| CN | 102928610 A | 2/2013 |
| CN | 103295873 A | 9/2013 |
| CN | 103335984 A | 10/2013 |
| CN | 103597574 A | 2/2014 |
| CN | 104254772 A | 12/2014 |
| CN | 104254901 A | 12/2014 |
| CN | 104582616 A | 4/2015 |
| EP | 0169469 A2 | 1/1986 |
| EP | 0437358 A2 | 7/1991 |
| EP | 1855306 A1 | 5/2006 |
| EP | 1730519 B1 | 7/2010 |
| EP | 3265817 A1 | 1/2018 |
| EP | 3265818 B1 | 2/2020 |
| GB | 2425178 A | 10/2006 |
| GB | 2491486 A | 12/2012 |
| JP | S63243864 A | 10/1988 |
| JP | 03001435 A | 8/1991 |
| JP | H0785834 A | 3/1995 |
| JP | H07130325 A | 5/1995 |
| JP | 10302710 A | 4/1997 |
| JP | H10247472 A | 9/1998 |
| JP | H1164283 A | 3/1999 |
| JP | 2000180413 A | 6/2000 |
| JP | 2001183345 A | 7/2001 |
| JP | 2002170518 A | 6/2002 |
| JP | 2004264043 A | 6/2002 |
| JP | 2005205181 A | 8/2005 |
| JP | 2006329710 A | 12/2006 |
| JP | 2007-51934 A | 3/2007 |
| JP | 2007170870 A | 7/2007 |
| JP | 2007218916 A | 8/2007 |
| JP | 2010169454 A | 8/2010 |
| JP | 2014515831 A | 7/2014 |
| JP | 2015503109 A | 1/2015 |
| JP | 2015504160 A | 2/2015 |
| KR | 1020020013544 A | 4/2007 |
| KR | 1020100106336 A | 10/2010 |
| WO | 9734534 A1 | 9/1997 |
| WO | 0160265 A1 | 8/2001 |
| WO | 2010075526 A2 | 7/2010 |
| WO | 2010136887 A1 | 12/2010 |
| WO | 2011114902 A1 | 9/2011 |
| WO | 20120143737 A1 | 10/2012 |
| WO | 2012164312 A2 | 12/2012 |
| WO | 2012174437 A1 | 12/2012 |
| WO | 2013098642 A2 | 7/2013 |
| WO | 2013098645 A2 | 7/2013 |
| WO | 2013102670 A1 | 7/2013 |
| WO | 2013/148162 | 10/2013 |
| WO | 2014/106165 A1 | 7/2014 |
| WO | 2014128629 A1 | 8/2014 |
| WO | 2014140601 A1 | 9/2014 |
| WO | 2014142926 A1 | 9/2014 |
| WO | 2014202828 A1 | 12/2014 |
| WO | 2015004457 A1 | 1/2015 |
| WO | 2015132579 A1 | 9/2015 |
| WO | 2016046748 A1 | 3/2016 |
| WO | 2016142674 A1 | 9/2016 |
| WO | 2016156615 A1 | 10/2016 |

OTHER PUBLICATIONS

Ahlf, Dorothy R. et al., "*Correlated Mass Spectrometry Imaging and Confocal Raman Microscopy for Studies of Three-Dimensional Cell Culture Sections*", Analyst, vol. 139, No. 18, pp. 4578 (2014).

Azimzadeh, Omid et al., "*Formalin-Fixed Paraffin-Embedded (FFPE) Proteome Analysis Using Gel-Free and Gel-Based Proteomics*", Journal of Proteome Research, vol. 9, No. 9, pp. 4710-4720 (2010).

Balgley, Brian M. et al., "*Evaluation of Archival Time on Shotgun Proteomics of Formalin-Fixed and Paraffin-Embedded Tissues*", Journal of Proteome Research, vol. 8, No. 2, pp. 917-925 (2009).

Balog, Julia et al., "*Identification of Biological Tissues by Rapid Evaporative Ionization Mass Spectrometry*", Analytical Chemistry, vol. 82, No. 17, pp. 7343-7350 (2010).

Balog, Julia et al., "*Supporting Information for Identification of Biological Tissues by Rapid Evaporative Ionization Mass Spectrometry*", pp. S1-S9, http://pubs.acs.org/doi/suppl/10.1021/ac101, (2013).

Balog, J. et al., "*Intraoperative Tissue Identification Using Rapid Evaporative Ionization Mass Spectrometry*", Science Translational Medicine, vol. 5, No. 194, pp. 194ra93 (2013).

Balog, J. et al., "*Supplementary Materials: Intraoperative Tissue Identification Using Rapid Evaporative Ionization Mass Spectrometry*", Science Translational Medicine, vol. 5, No. 194, pp. 194ra93 (2013).

Bean, Heather D. et al., "*Bacterial Volatile Discovery Using Solid Phase Microextraction and Comprehensive Two-Dimensional Gas Chromatographytime-of-Flight Mass Spectrometry*", Journal of Chromatography B, vol. 901, pp. 41-46 (2012).

Bellet, V. et al., "*Proteomic Analysis of RCL2 Paraffin-Embedded Tissues*", Journal of Cellular and Molecular Medicine, vol. 12, No. 5B, pp. 2027-2036 (2008).

Bocklitz, T.W. et al., "*Deeper Understanding of Biological Tissue: Quantitative Correlation of MALDI-TOF and Raman Imaging*", Analytical Chemistry, vol. 85, No. 22, pp. 10829-10834 (2013).

Cole, Laura M. et al., "*Mass Spectrometry Imaging for the Proteomic Study of Clinical Tissue*", Proteomics-Clinical Applications, vol. 9, No. 3-4, pp. 335-341 (2015).

Crawshaw, Benjamin et al., "*Gastrointestinal Surgery: Real-Time Tissue Identification During Surgery*", Nature Review/Gastroenterology & Hepatology Nature, vol. 10, No. 11. pp. 624-625.

Cselik, Z. et al., "*Impact of Infrared Laser Light-Induced Ablation at Different Wavelengths on Bovine Intervertebral Disc Ex Vivo: Evaluation with Magnetic Resonance Imaging and Histology*", Lasers in Surgery and Medicine, vol. 44, No. 5, pp. 406-412 (2012).

Davies, T.J. et al., "*Volatile Products from Acetylcholine as Markers in the Rapid Urine Test Using Head-Space Gas-Liquid Chromatography B: Biomedical Sciences and Applications*", Journal of Chromatography, vol. 307, pp. 11-21 (1984).

European Commission, "*ISD Report Summary*", http://cordis.europa.eu/result/rcn/163435_e, (2016).

Fahy, Eoin, et al., "*Lipid Classification, Structures and Tools*", Biochimica at Biophysica Acta (BBA)—Molecular and Cell Biology of Lipids, vol. 1811, No. 11, pp. 637-647 (2011).

Gerbig, Stefanie et al., "*Analysis of Colorectal Adenocarcinoma Tissue by Desorption Electrospray Ionization Mass Spectrometric Imaging*", Analytical and Bioanalytical Chemistry, vol. 403, No. 8, pp. 2315-2325 (2012).

Golf, Ottmar et al., "*Rapid Evaporative Ionization Mass Spectrometry Imaging Platform for Direct Mapping from Bulk Tissue and Bacterial Growth Media*", Analytical Chemistry, vol. 87, No. 5, pp. 2527-2534 (2015).

(56) References Cited

OTHER PUBLICATIONS

Golf, Ottmar et al., "XMS: Cross-Platform Normalization Method for Multimodal Mass Spectrometric Tissue Profiling", Journal of the American Society for Mass Spectrometry, vol. 26, No. 1, pp. 44-54 (2014).
Guenther, Sabine et al., "Electrospray Post-Ionization Mass Spectrometry of Electrosurgical Aerosols", Journal of the American Society for Mass Spectrometry, vol. 22, No. 11, pp. 2082-2089 (2011).
Gustafsson, Ove J.R. et al., "Proteomic Developments in the Analysis of Formalin-Fixed Tissue", Biochimica et Biophysica Acta, vol. 1854, No. 6, pp. 559-580.
Hobbs, S.K. et al., "Magnetic Resonance Image-Guided Proteomics of Human Glioblastoma Multiforme", Journal of Magnetic Resonance Imaging, vol. 18, pp. 530-536 (2003).
Hsu, Cheng-Chih et al., "Visualizing Life with Ambient Mass Spectrometry", Current Opinion in Biotechnology, vol. 31, pp. 24-34 (2015).
Jadoul, L. et al., "Matrix-Assisted Laser Desorption/Ionization Mass Spectrometry and Raman Spectroscopy: An Interesting Complementary Approach for Lipid Detection in Biological Tissues", European Journal of Lipid Science and Technology. vol. 116, No. 8, pp. 1080-1086 (2014).
Jain, M. et al., "Metabolite Profiling Identifies a Key Role for Glycine in Rapid Cancer Cell Proliferation", American Association for the Advancement of Science, vol. 336, No. 6084, pp. 1040-1044 (2012).
Jarmusch, Alan K et al., "Detection of Strep Throat Causing Bacterium Directly from Medical Swabs by Touch Spray-Mass Spectrometry", Analyst, vol. 139, No. 19, pp. 4785 (2014).
Jarmusch, Alan K. et al., "Supplemental Information Detection of Strep Throat Causing Bacterium Directly from Medical Swabs by Touch Spray-Mass Spectrometry", http://www.rsc.org/suppdata/an/c4/c4an00959(2016).
Lazova, Rossitza et al., "Imaging Mass Spectrometry—A New and Promising Method to Differentiate Spitz Nevi From Spitzoid Malignant Melanomas", American Journal of Dermatopathology, vol. 34, No. 1, pp. 82-90 (2012).
Li, Yan et al., "Aberrant Mucin5B Expression in Lung Adenocarcinomas Detected by iTRAQ Labeling Quantitative Proteomics and Immunohistochemistry", Clinical Proteomics, vol. 10, No. 1, pp. 15 (2013).
Lieuwe, D.J. et al., "Volatile Metabolites of Pathogens: A Systematic Review", PLoS Pathogens, vol. 9, No. 5, pp. 1003311.
Luge, S. et al., "Use of a Lower Power, High Frequency Stabilized Capacitive Plasma Combined with Graphite Furnace Vaporization for the Atomic Emission Spectrometric Analysis of Serum Samples", Analytical Chimica Acta, vol. 332, No. 2-3, pp. 193-199 (1996).
Mccullough, Bryan J. et al., "On-Line Reaction Monitoring by Extractive Electrospray Ionisation", Rapid Communications in Mass Spectrometry, vol. 25, No. 10, pp. 1445-1451 (2011).
Murray, Patrick R, "What Is New in Clinical Microbiology-Microbial Identification by MALDI-TOF Mass Spectrometry", Journal of Molecular Diagnostics, vol. 14, No. 5, pp. 419-423 (2012).
Nicholson, Jeremy K. et al., "Metabolic Phenotyping in Clinical and Surgical Environments", Nature, vol. 491, No. 7424 pp. 384-392 (2012).
Pirro, Valentina et al., "Direct Drug Analysis from Oral Fluid Using Medical Swab Touch Spray Mass Spectrometry", Analytica Chimica Acta, vol. 861, pp. 47-54.
Plata, N. et al., "Aerosols Sampling Using a New Cryogenic Instrument", Journal of Aerosol Science, vol. 37, No. 12, pp. 1871-1875 (2006).
Rodriguez-Rigueiro, Teresa et al., "A Novel Procedure for Protein Extraction from Formalin-Fixed Paraffin-Embedded Tissues", Proteomics, vol. 11, No. 12, pp. 2555-2559 (2011).
Schafer, Karl-Christian et al., "In Vivo, In Situ Tissue Analysis Using Rapid Evaporative Ionization Mass Spectrometry", Angewandte Chemie International, vol. 48, No. 44, pp. 8240-8242 (2009).
Shane, Ellis R. et al., "Surface Analysis of Lipids by Mass Spectrometry: More Than Just Imaging", Progress in Lipid Research Pergamon Press, vol. 52, No. 4, pp. 329-353.
Shoemaker, Robert H., "The NCI60 Human Tumour Cell Line Anticancer Drug Screen", (2013).
Strittmatter, N. et al., "Anaylsis of Intact Bacteria Using Rapid Evaporative Ionisation Mass Spectrometry", Chemical Communications, vol. 49, No. 55, pp. 6188 (2013).
Strittmatter, N. et al., "Characterization and Identification of Clinically Relevant Microorganisms Using Rapid Evaporative Ionization Mass Spectrometry", Analytical Chemistry, vol. 86, No. 13, pp. 6555-6562 (2014).
Strittmatter, N. et al., "Taxon-Specific Markers for the Qualitative and Quantitative Detection of Bacteria in Human Samples", http://www.msacl.org/2015_US_Long_Abstract.
Tait, Emma et al., "Identification of Volatile Organic Compounds Produced by Bacteria Using HS-SPME-GC-MS", Journal of Chromatographic Sci, pp. 1-11.
Uribe, D.O. et al., "Piezoelectric Self-Sensing System for Tactile Intraoperative Brain Tumor Delineation in Neurosurgery", Proceedings of the $31^{st}$ Annual International Conference of the IEEE Engineering in Medicine and Biology Society: Engineering the Future of BioMedicine, pp. 737-740 (2009).
Vander Wilp, W. et al., "Lead in Micro-Samples of Whole Blood by Rhenium-Cup in-Torch Vaporization-Inductively Coupled Plasma-Atomic Emission Spectrometry (ITV-ICP-AES)", Fresenius' Journal of Analytical Chemistry, vol. 368, No. 7, pp. 734-736 (2000).
Vircks, Kyle E. et al., "Rapid Screening of Synthetic Cathinones as Trace Residues and in Authentic Seizures Using a Portable Mass Spectrometer Equipped with Desorption Electrospray Ionization", Rapid Communications in Mass Spectrometry, vol. 26, No. 23, pp. 2665-2672 (2012).
Summons to Attend Oral Proceedings Pursuant to Rule 115(1) EPC of EP Application No. 12726643.5, dated Apr. 20, 2018, 7 pages.
Chen et al., "Surface desorption atmospheric pressure chemical ionization mass spectrometry for direct ambient sample analysis without toxic chemical contamination", Journal of Mass Spectrometry, 42(8):1045-1056, Jan. 1, 2007.
Chen, H., et al: "Neutral desorption sampling coupled to extractive electrospray ionization mass spectrometry for rapid differentiation of biosamples by metabolomic fingerprinting", Journal of Mass Spectromety, vol. 42, No. 9, Sep. 1, 2007 pp. 1123-1135.
Hensman C., et al: "Chemical Composition of Smoke Produced by High-Frequency Electrosurgery in a Closed Gaseous Environment an in Vitro Study", Surgical Endoscopy, vol. 12, No. 8, Aug. 1, 1998 (Aug. 1, 1998), pp. 1017-1019.
Moot, A. et al: "Composition of Volatile Organic Compouds in Diathermy Plume as Detected by Selected Ion Flow Tube Mass Spectrometry", ANZ Journal of Surgery, vol. 77, No. 1-2, (Jan. 2007) pp. 20-23.
Strittmatter, N.: "Home—Miss Nicole Strittmatter" Retrieved from the Internet URL: http://www.imperial.ac.uk/people/n.strittmatter12 [retrieved on May 19, 2016] the whole document.
Wehofsky, et al "Automated deconvolution and deisotoping of electrospray mass spectra" J. Mass Spectrom. 2002; 37: pp. 223-229.
Al Sahaf et al., "Chemical Composition of Smoke Produced by High-Frequency Electrosurgery", Irish Journal of Medical Science, vol. 176, No. 3, pp. 229-232, 2007.
Barrett et al., "Surgical Smoke: A Review of the Literature", Surgical Endoscopy, vol. 17, No. 6, pp. 979-987, 2003.
Down, "A DESI-Rable Ionization Revolutionizes Mass Spectrometry", Base Peak, 2005.
International Search Report and Written Opinion for International Application. No. PCT/IB2012/003009, dated Aug. 14, 2013, 17 pages.
PCT International Search Report and Written Opinion for International Appln. No. PCT/IB2010/001261, dated Sep. 21, 2010, 5 pages.
PCT International Search Report and Written Opinion for International Appln. No. PCT/IB2012/002995, dated Sep. 10, 2013, 3 pages.

(56) References Cited

OTHER PUBLICATIONS

Qiao et al., "Electrostatic-Spray Ionization Mass Spectrometry", Analytical Chemistry, vol. 84, No. 17, pp. 7422-7430, 2012.

Lee et al., "Thermally Assisted Electrospray Interface for Liquid Chromatography/Mass Spectrometry", Rapid Communications in Mass Spectrometry, vol. 6, pp. 727-733, 1992.

McEwen et al., "Analysis of Solids, Liquids, and Biological Tissues Using Solids Probe Introduction at Atmospheric Pressure on Commercial LC/MS Instruments", Anal. Chem., vol. 77, pp. 7826-7831, 2005.

Sakairi et al., "Characteristics of a Liquid Chromatograph/Atmospheric Pressure Ionization Mass Spectrometer", Anal. Chem., vol. 60, pp. 774-780, 1988.

Takats et al., "Characterization of DESI-FTICR Mass Spectrometry—From ECD to Accurate Mass Tissue Analysis", Journal of Mass Spectrometry, vol. 43, pp. 196-203, 2008.

Eagles, et al., "Fast Atom Bombardment Mass Spectrometry of Amine Mixtures", John Wiley & Sons, Ltd, 1988.

Slemr et al., Concentration Profiles of Diamines in Fresh and aerobically Stored Park and Beef, American Chemical Society, 1985.

Mulligan, Christopher C. et al., "Desorption electrospray ionization with a portable mass spectrometer in situ analysis of ambient surfaces", Chemical Communications—Chemcom, No. 16, pp. 1709-1711, (Jan. 2006).

Van Berkel, "Thin-Layer Chromatography and El3ectrospray Mass Spectrometry Coupled Using a Surface Sampling probe". Anal. Chem. 2002.

Takats et al., "Mass Spectrometry Sampling Under Ambient Conditions with Desorption Electrospray Ionization", Science, vol. 306, 2004.

Tottszer et al., "Laser Heating Versus Resistive Heating in the Field-Desorption Mass Spectrometry of Organic Polymers", J. Phys. D: Appl. Phys., vol. 21, pp. 1713-1720, 1988.

Zhou, X., et al., "Development of miniature mass spectrometry systems for bioanalysis outside the conventional laboratories." Bioanalysis, 6 (11) 1497-1508 (2014).

Bolt, F., et al., "Automated High-Throughput Identification and Characterization of Clinically Important Bacteria and Fungi using Rapid Evaporative Ionization Mass Spectrometry," American Chemical Socieity, 88 9419-9426 (2016).

McJimpsey, E.L., et al., "Parameters Contributing to Efficient Ion Generation in Aerosol MALDI Mass Spectrometry," American Society for Mass Spectrometry pp. 1044-0305 (2007).

Mutters, N.T., et al., "Performance of Kiestra Total Laboratory Automation Combined with MS in Clinical Microbiology Practice," Annals of Laboratory Medicine 34: 111-117 (2014).

Longuespée, R., et al., Tissue Proteomics for the Next Decade? Towards a Molecular Dimension in Histology, OMICS A Journal of Integrative Biology 28(9): 539-552 (2014).

Lu, K., et al., "Arsenic Exposure Perturbs the Gut Microbiome and its Metabolic Profile in Mice: An Integrated Metagenomics and Metabolomics Analysis," Environmental Health Perspectives, 122(3): 284-291 (2014).

Suarez, S., et al., Ribosomal proteins as biomarkers for bacterial identification by mass spectrometry in the clinical microbiology laboratory, Journal of microbiological Methods, 94: 390-396 (2013).

Trimpin, S. et al., New Ionization Method for Analysis on Atmospheric Pressure Ionization Mass Spectrometers Requiring Only Vacuum and Matrix Assistance, Analytical Chemistry, 85:2005-2009 (2013).

Cha, S., Laser desorption/ionization mass spectrometry for direct profiling and imaging of small moledcules from raw biological materials, Doctoral Dissertation, Iowa State University (2008).

Asano et al., "Self-aspirating atmospheric pressure chemical ionization source for direct sampling of analytes on Surfaces in liquid solution", Rapid Communications in Mass Spectrometry 2005.

International Search Report and Written Opinion for application No. PCT/GB2017/051050, dated Jun. 27, 2017, 15 pages.

Gerbig, Stefanie et al, "Spatially resolved investigation of systemic and contact pesticides in plant material by desorption electrospray ionization mass spectrometry imagine", Analytical and Bioanalytical Chemistry, 407(24):7379-7389 (2015).

Lesiak, A., et al., "Rapid detection by direct analysis in real time-mass spectrometry (DART-MS) of psychoactive plant drugs of abuse: the case of Mitragyna speciosa aka "Kratom"", 242:210-218 (2014).

Bartels, B. et al., "Spatially resolved in vivo plant metabolomics by laser ablation-based mass spectrometry imaging (MSI) techniques: LDI-MSI and LAESI", Frontiers in Plant Science vol. 6 (2015).

Nielen, M et al., "Desorption electrospray ionization mass spectrometry in the analysis of chemical food contaminants in food", Trac Trends in Analytical Chemistry, 30(2):165-180 (2011).

Boughton, B. et al., "Mass spectrometry imaging for plant biology: a review", Phytochemistry Reviews, 15(3):445-488 (2015).

Schäfer, K.C., et al., "In Situ, Real-Time Identification of Biological Tissue by Ultraviolet and Infrared Laser Desorption Ionization Mass Spectrometry", Analytical Chemistry, 83(5):1632-1640, Mar. 1, 2011.

International Search Report and Written Opinion for International Application No. PCT/GB2016/052956, dated Jan. 26, 2017, 16 pages.

Hsu, et al., "Microscopy ambient ionization top-down mass spectrometry reveals developmental patterning", Proceedings of the National Academy of Sciences, vol. 110, No. 37, pp. 14855-14860, Aug. 22, 2013.

Na, et al., "Development of a Dielectric Barrier Discharge Ion Source for Ambient Mass Spectrometry", Journal of the American Society for Mass Spectrometry, Elsevier Science Inc, vol. 18, No. 10, pp. 1859-1862, Sep. 20, 2007.

Jackson, S. N. et al. On-line laser desorption/ionization mass spectrometry of matrix-coated aerosols, Rapid Communications in Mass Spectrometry, vol. 18, pp. 2041-2045 (2004).

Dong, Y., et al., "Sample Preparation for Mass Spectrometry Imaging of Plant Tissues: A Review", Frontiers in Plant Science 7(60): 1-16 (2016).

Communication pursuant to Article 94(3) EPC, for application No. 16710788.7, dated Jun. 13, 2019, 9 pages.

Examination Report under Section 18(3), for application No. GB1714122.7, dated May 9, 2019, 6 pages.

Bagley, B.M., et al., "Evaluation of archival time on shotgun proteomics of formalin fixed and paraffin-embedded issues", Journal of Proteome Research 8(2):917-925, (2009).

Cho, YT., et al. "Differentiation of Virulence of Helicobacter Pyloriby Matrix-Assited Laser Desorption/Ionization Mass Spectrometry and Multivariate Analyses" Clinica Chimica ACTA, Elsevier BV, 424:123-130, May 26, 2013.

Kohler, M. et al. "Characterization of lipid extracts from brain tissue and tumors using Raman spectroscopy and mass spectrometry," Anal Bioana Chem, 393:1513-1520, Jan. 20, 2009.

Harry, K. H., et al. "Effect of protein coating of flocked swabs on the collection and release of clinically important bacteria", Indian Journal of Medical Microbiology, 32(3):301-303 (2014).

Blais, B. W., "Swab-Based Enzyme Immunoassay System for Detection of Meat Residues on Food Contact Surfaces as a Hygiene Monitoring Tool", Journal of Food Protection, 62(4):386-389 (1999).

Farhat, S. E., et al., "Efficacy of a Swab Transport System in Maintaining Viability of Neisseria gonorrhoeae and *Streptococcus pneumoniae*", Journal of Clinical Microbiology, 39(8)2958-2960 (2001).

Harry, E. L. et al., "Direct analysis of pharmaceutical formulations from non-bonded reversed-phase thin-layer chromatography plates by desorption electrospray ionisation ion mobility mass spectrometry", Rapid Communications in Mass Spectrometry, 23(17):2597-2604, Jul. 28, 2009.

Hachmoeller et al., "Element bioimaging of liver needle biopsy specimens from patients with Wilson's disease by laser ablation-inductively coupled plasma-mass spectrometry", Journal of Trace Elements in Medicine and Biology, 35:97-102, Feb. 10, 2016.

Guenther et al., "Spatially Resolved Metabolic Phenotyping of Breast Cancer by Desorption Electrospray Ionization Mass Spectrometry", Cancer Research, 75:1828-1837, Feb. 17, 2015.

(56) References Cited

OTHER PUBLICATIONS

Chipuk, J. E., et al., "Transmission Mode Desorption Electrospray Ionization ", Journal of the American Society for Mass Spectrometry, 19(11):1612-1620, Nov. 1, 2008.

Santagata, S., et al., "Intraoperative mass spectrometry mapping of an onco-metabolite to guide brain tumor surgery", Proceedings of the National Academy of Sciences (PNAS), 111(30):11121-11126, Jun. 30, 2014.

Chen, H., et al., "What Can We Learn from Ambient Ionization Techniques?", Journal of the American for Mass Spectrometry, 20:1947-1963, (2009).

Sankaranaryanan, G., et al., "Common Uses and Cited Complications of Energy in Surgery", Surg Endosc., 27;3056-3072, (2013).

Rau, H.G., et al., "The use of water-jet dissection in open and laparoscopic liver resection", HPB, 10: 275-280, (2008).

Chen, H., et al., "Desorption Electrospray Ionization Mass spectometry for high-throughput analysis of Pharmaceutical samples in the ambient environment" Anal. Chem 77:6915-6927 (2005).

Adams, F., et al, "Inorganic Mass Spectrometry", copyright John Wiley Sons, Inc. pp. 174-180 (1988).

Office Action for CN Patent Application No. 201680025801.0 dated Apr. 7, 2020.

Office Action for CN Patent Application No. 201680025801.0 dated Apr. 7, 2020 [translation].

Vemury, S., and Pratsinis, S.E., "Charging and Coagulation During Flame Synthesis of Silica", Journal or Aerosol Science 21(6):951-966.

Examination Report under Section 18(3), for application No. GB1715787.6, dated Jun. 1, 2020, 6 pages.

CNOA for application No. 201680026285.3 dated Jun. 12, 2020.

Panpradist, N., et al., "Swab Sample Transfer for Point-Of-Care Diagnostics: Characterization of Swab types and Manual Agitation Methods", PLOS One 9(9):1-11 (2014).

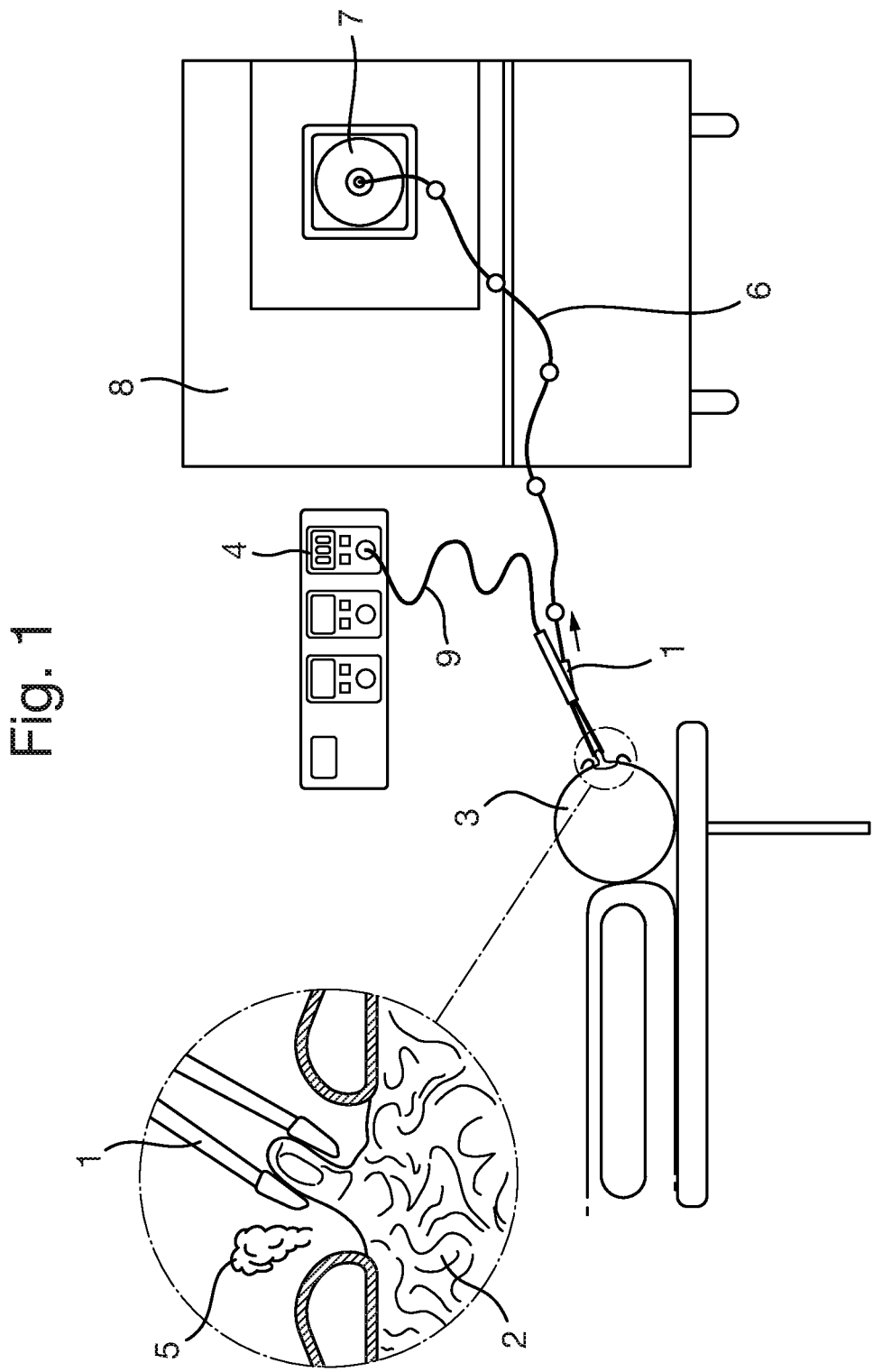

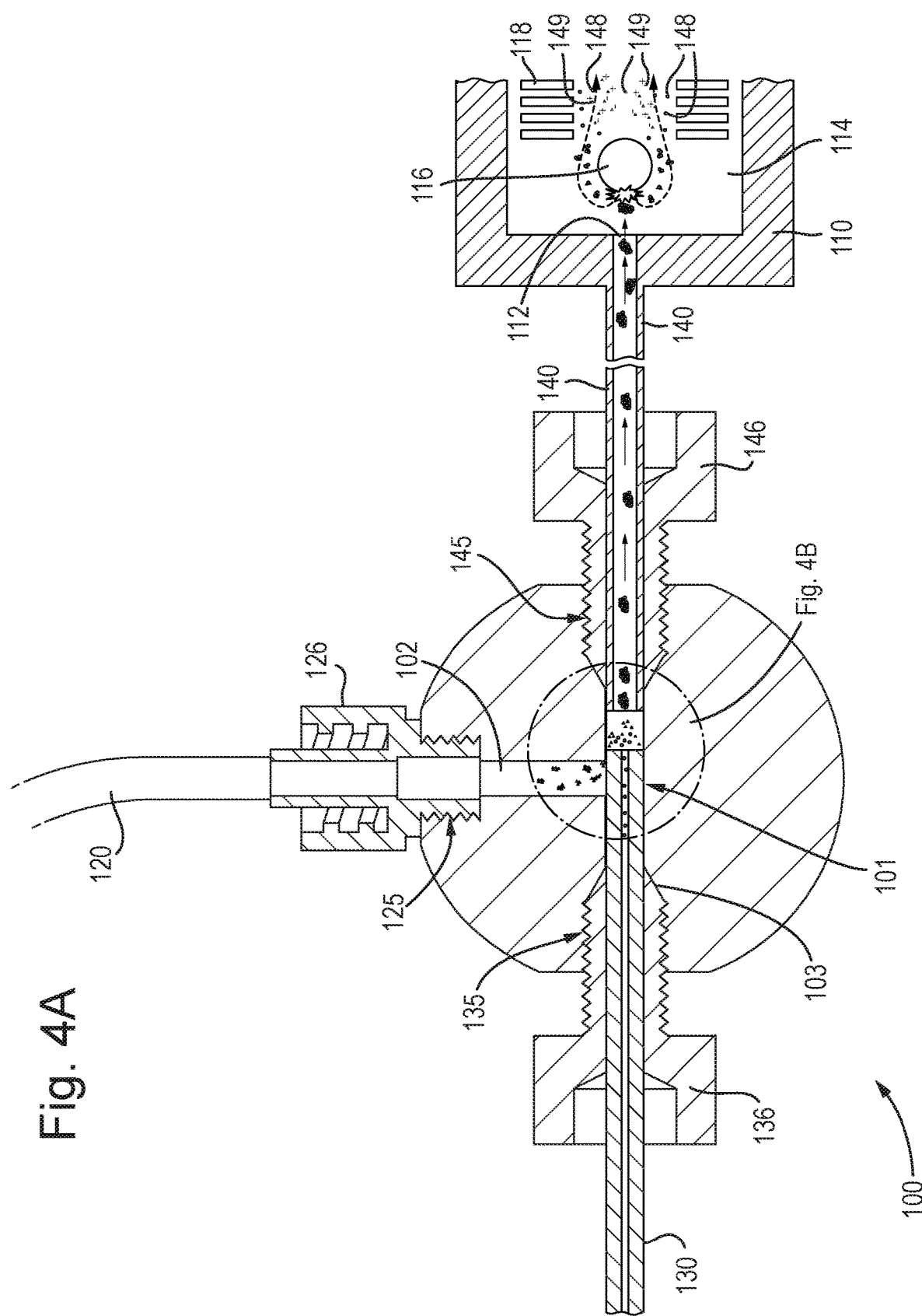

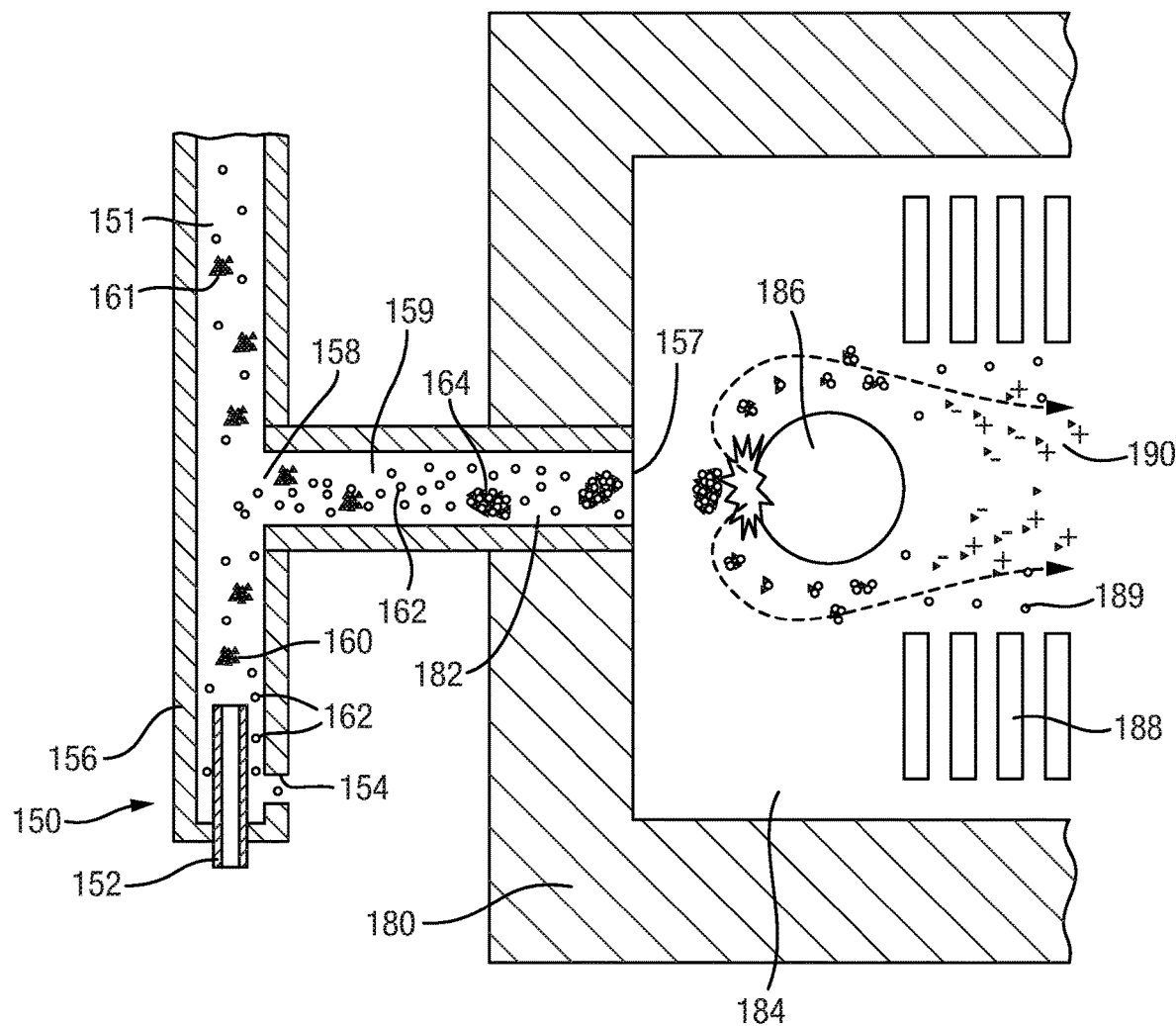

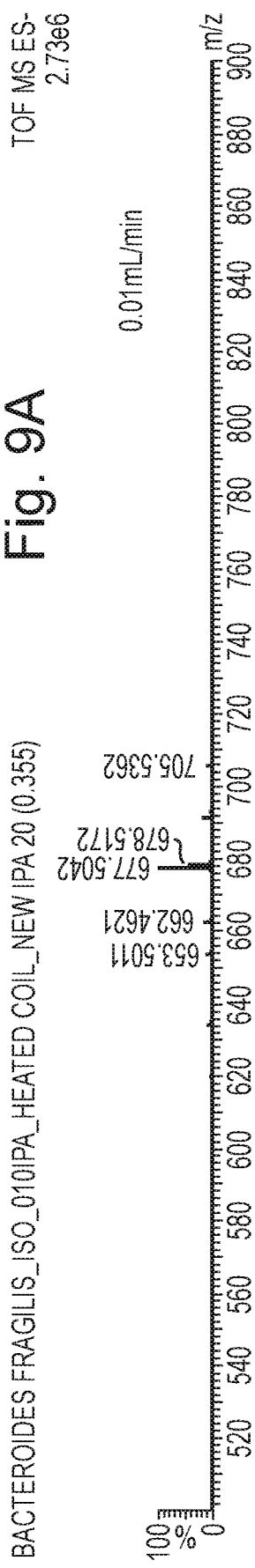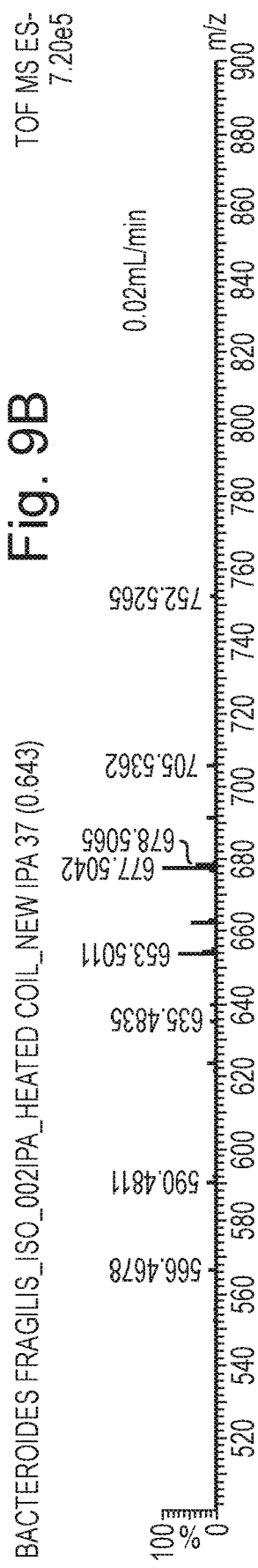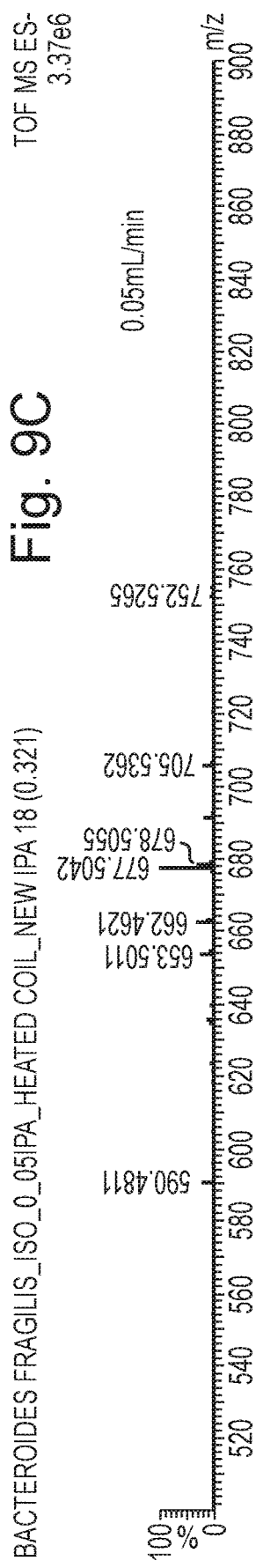

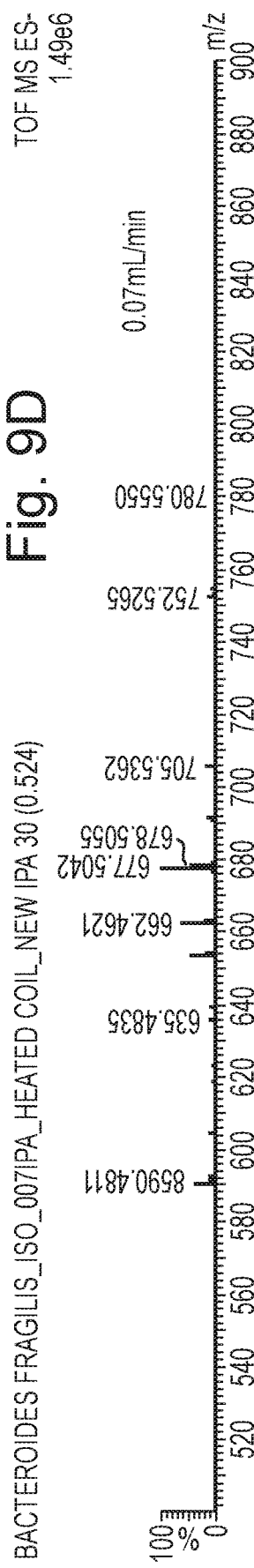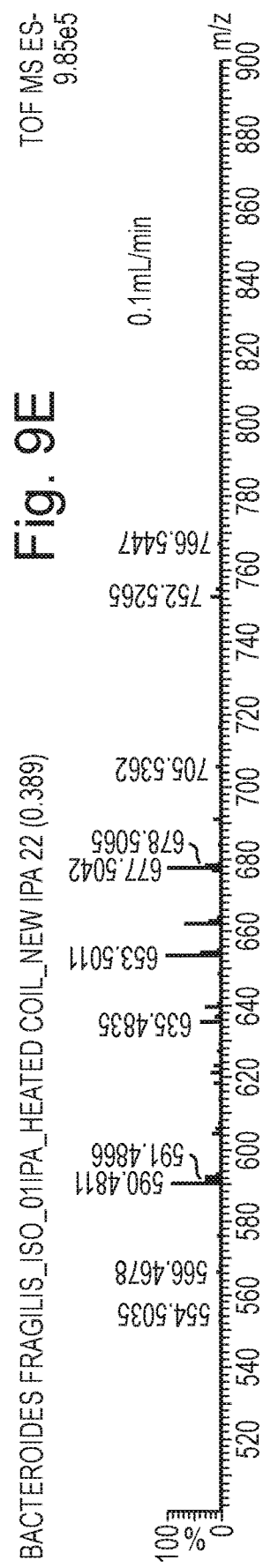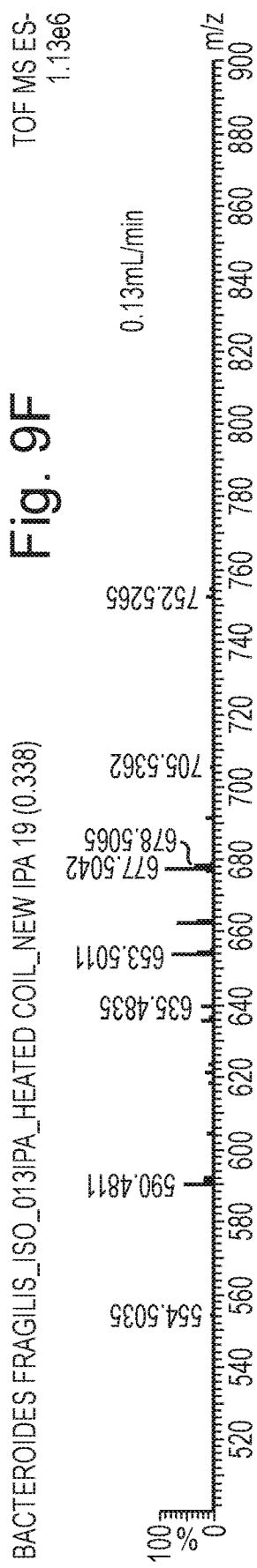

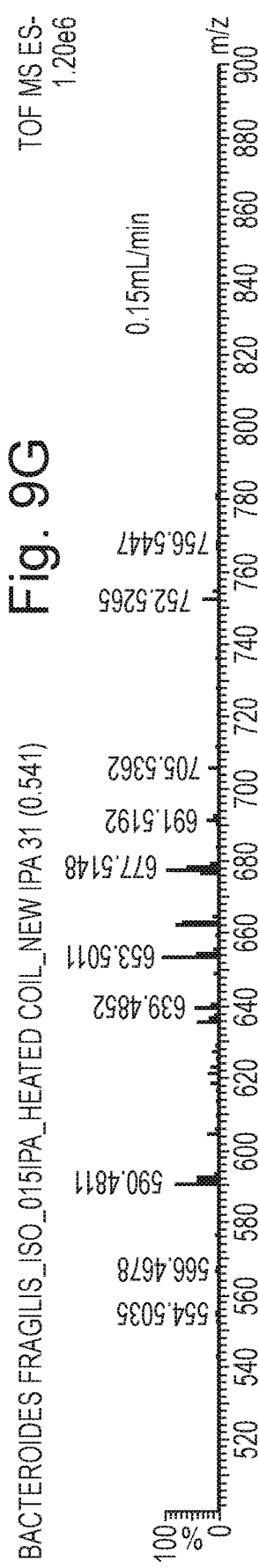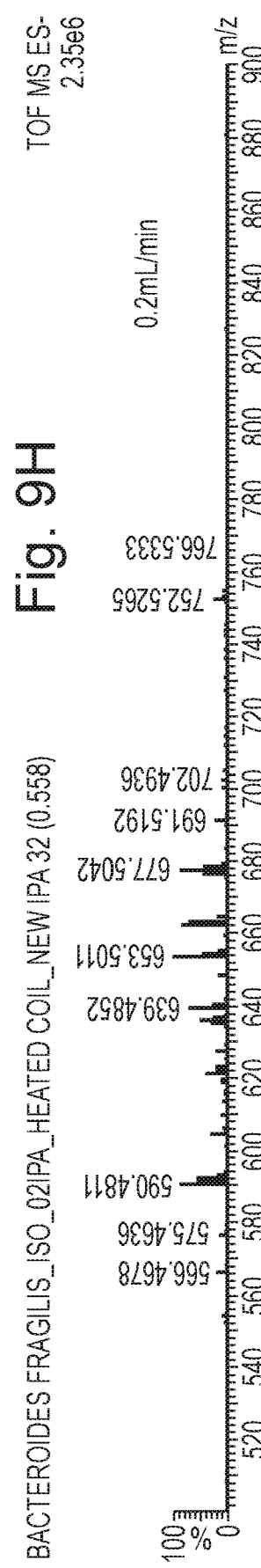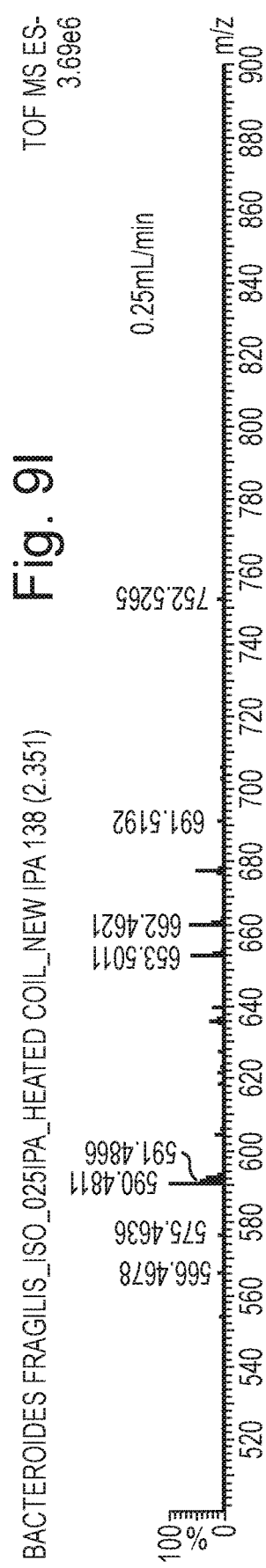

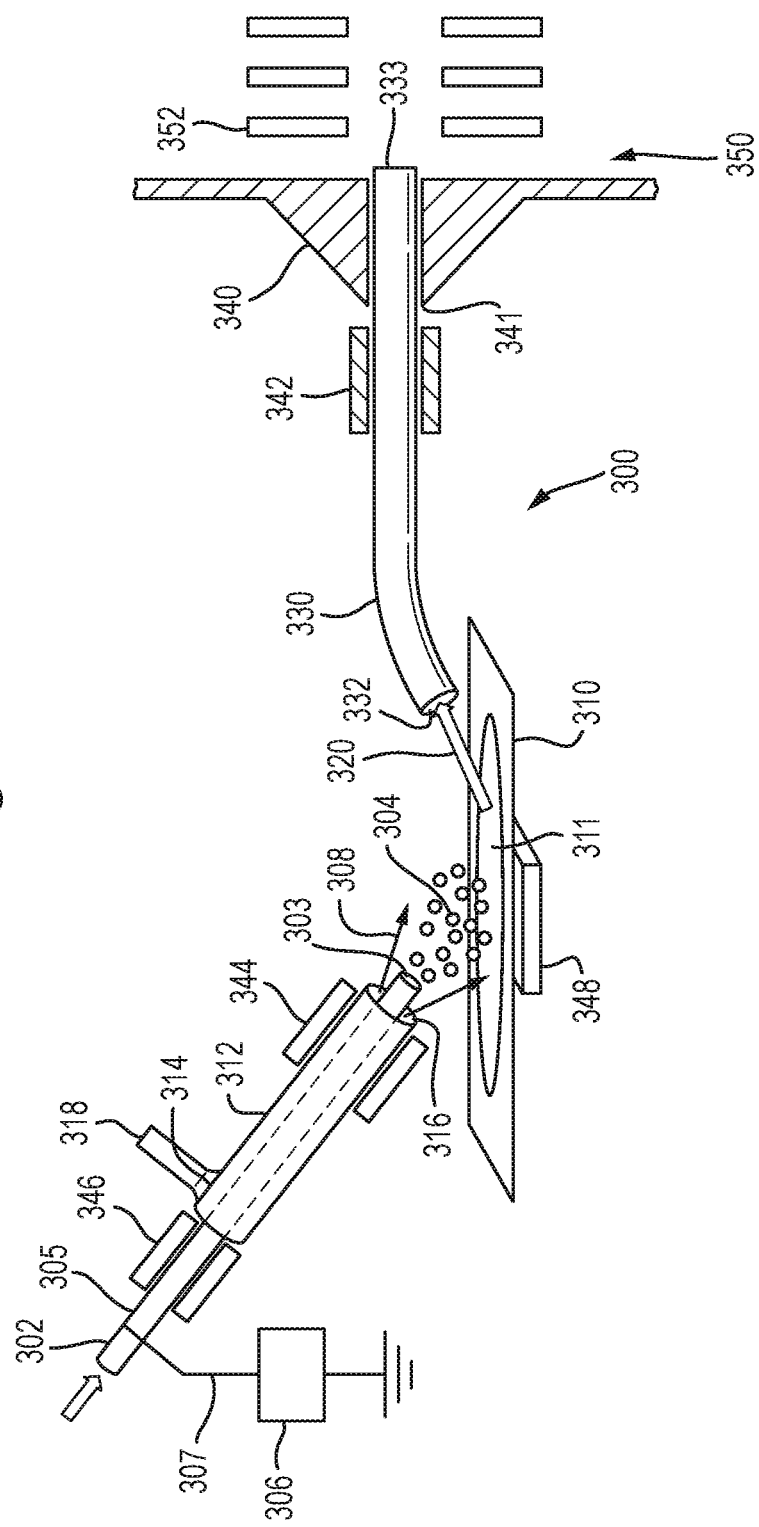

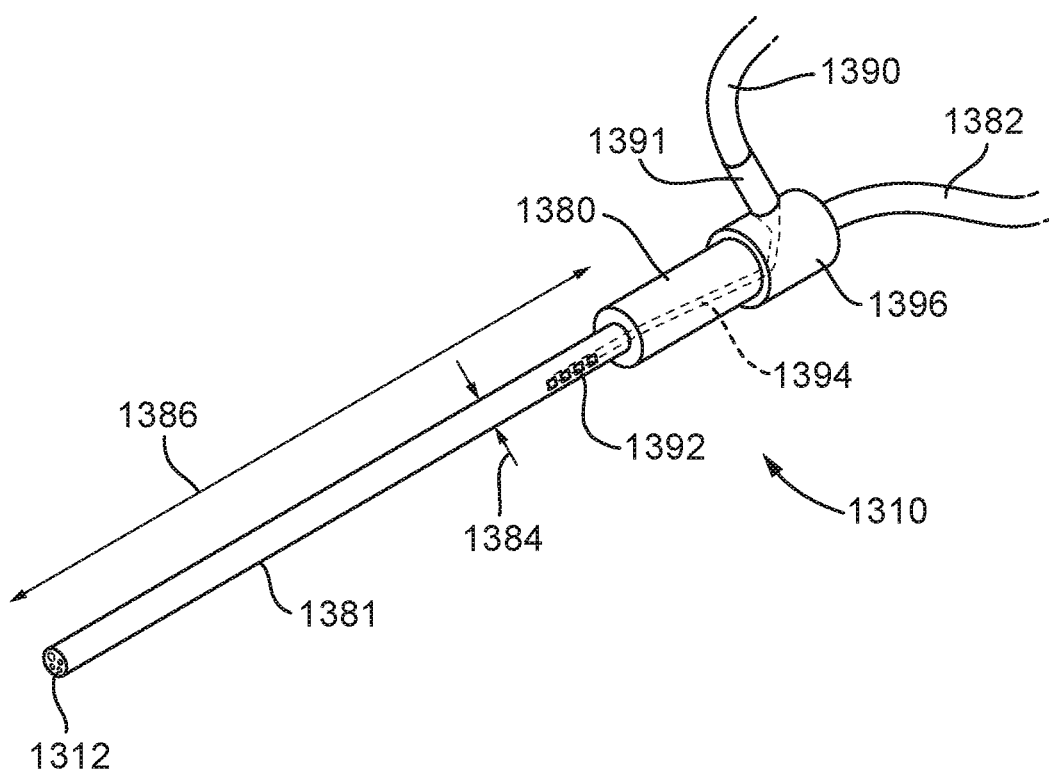

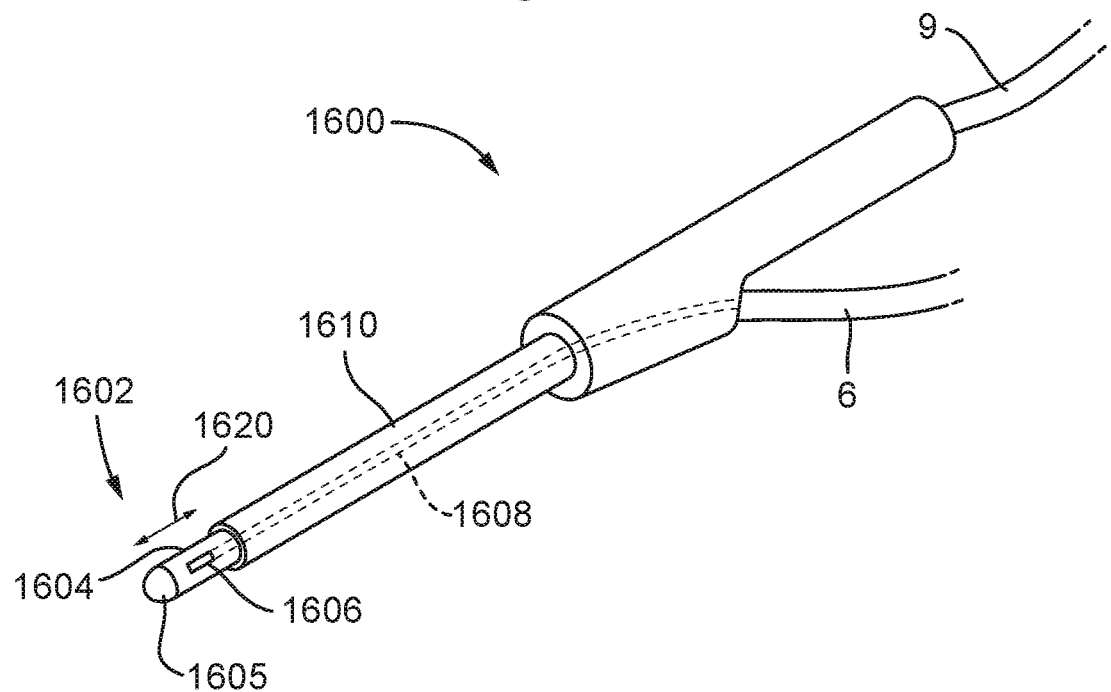
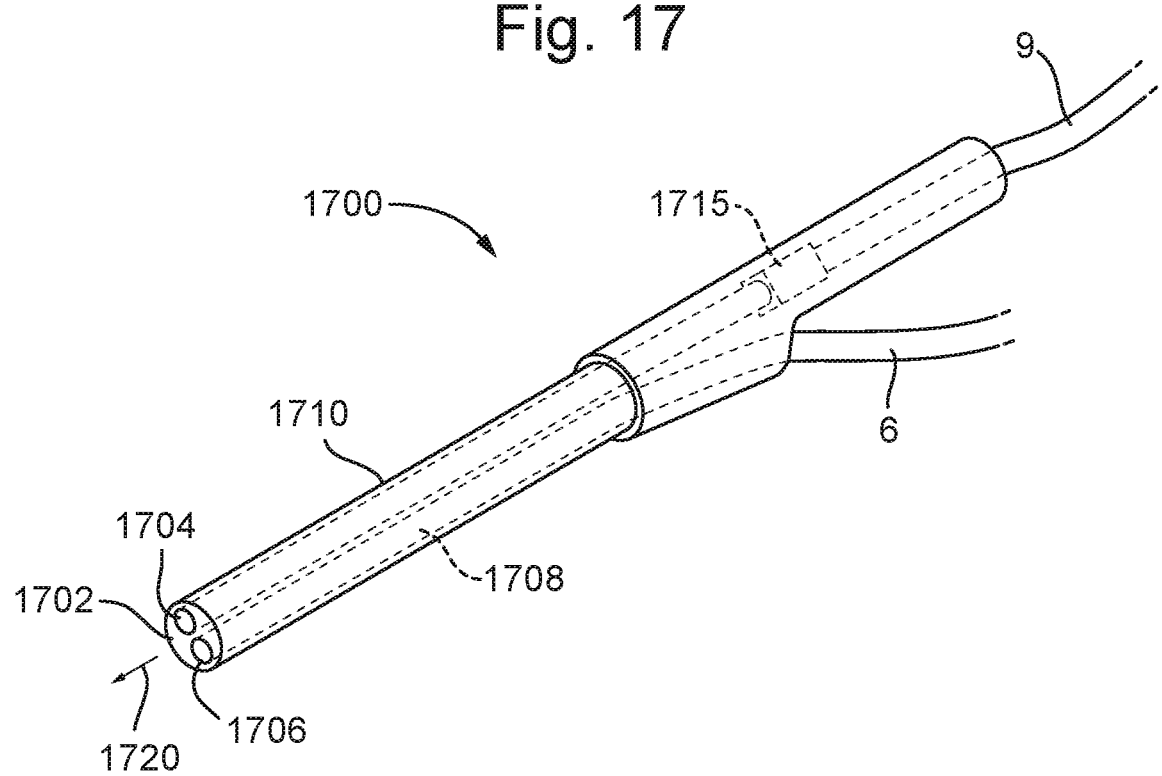

INLET INSTRUMENTATION FOR ION ANALYSER COUPLED TO RAPID EVAPORATIVE IONISATION MASS SPECTROMETRY ("REIMS") DEVICE

CROSS-REFERENCE TO RELATED APPLICATIONS

This application represents the U.S. National Phase of International Application number PCT/GB2016/050620 entitled "Inlet Instrumentation for Ion Analyser Coupled to Rapid Evaporative Ionisation Mass Spectrometry ("REIMS") Device" filed 7 Mar. 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention generally relates to mass spectrometry and/or ion mobility spectrometry, and in particular to apparatus for performing ambient ionisation mass spectrometry and/or ion mobility spectrometry including rapid evaporative ionisation mass spectrometry ("REIMS"), mass spectrometers, ion mobility spectrometers, methods of rapid evaporative ionisation mass spectrometry, methods of mass spectrometry, methods of ion mobility spectrometry and methods of electrosurgery and an electrosurgical apparatus.

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

Rapid evaporative ionisation mass spectrometry ("REIMS") is a relatively new technique that is useful for the analysis of many different types of samples including the identification of tissue.

Reference is made to N. Strittmatter et al., Anal. Chem. 2014, 86, 6555-6562 which discloses an investigation into the suitability of using rapid evaporative ionisation mass spectrometry as a general identification system for bacteria and fungi.

The known approach for analysing bacterial colonies by rapid evaporative ionisation mass spectrometry involves using bipolar electrosurgical forceps and an electrosurgical RF generator. A bacterial colony is scraped from the surface of an agar layer using the bipolar electrosurgical forceps and a short burst of RF voltage from the electrosurgical RF generator is applied between the bipolar electrosurgical forceps. For example, it is known to apply 60 W of power in a bipolar mode at a frequency of 470 kHz sinusoid. The RF voltage which is applied to the electrosurgical forceps has the result of rapidly heating the particular portion of the bacterial colony which is being analysed due to its nonzero impedance. The rapid heating of the microbial mass results in an aerosol being generated. The aerosol is transferred directly into a mass spectrometer and the aerosol sample may then be analysed by the mass spectrometer. It is known to utilise multivariate statistical analysis in order to help distinguish and identify different samples.

It is desired to provide an improved apparatus for analysing a target or tissue using an ambient ionisation ion source.

SUMMARY

According to an aspect there is provided apparatus comprising:

a first device for generating aerosol, smoke or vapour from one or more regions of a target;

an inlet conduit to an ion analyser or mass spectrometer, the inlet conduit having an inlet through which the aerosol, smoke or vapour passes; and a Venturi pump arrangement arranged and adapted to direct the aerosol, smoke or vapour towards the inlet.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The arrangement disclosed in N. Strittmatter et al., Anal. Chem. 2014, 86, 6555-6562 does not teach or suggest providing a Venturi pump arrangement to direct aerosol, smoke or vapour towards an inlet of an inlet conduit. The provision of a Venturi pump arrangement results in improved aspiration of the aerosol, smoke or vapour and results in an improved signal intensity of analyte ions.

The Venturi pump arrangement may be arranged and adapted to direct the aerosol, smoke or vapour onto a deflection device or surface prior to the aerosol, smoke or vapour passing through the inlet.

The deflection device may comprise a hollow member having a first side and a second side, wherein the first side may be solid and the second side may comprise one or more apertures arranged and adapted to allow the aerosol, smoke or vapour to pass therethrough; and the Venturi pump arrangement may be arranged and adapted to direct the aerosol, smoke or vapour onto the first surface of the deflection device.

The first side may be arranged and adapted to deflect oncoming matter away from the second side and/or the one or more apertures. In use, relatively large particles of oncoming matter (e.g., contained in the aerosol, smoke or vapour) may be deflected away from the inlet conduit. Relatively small particles of matter (e.g., contained in the aerosol, smoke or vapour) may be deflected but may still be drawn into the inlet conduit, for example due to a pressure difference between the region adjacent the one or more apertures and the ion analyser or mass spectrometer.

The apertures may be in fluid communication with a cavity or passage within the hollow member, and the inlet may be in fluid communication with the cavity or passage.

The apparatus may further comprise a matrix conduit for introducing and mixing a matrix with the aerosol, smoke or vapour prior to the aerosol, smoke or vapour passing through the inlet.

The matrix may comprise polar molecules, water, one or more alcohols, methanol, ethanol, isopropanol, acetone or acetonitrile. The matrix may comprise a lockmass or calibration compound.

The matrix conduit may be in fluid communication with the cavity or passage.

The hollow member may comprise an axial passage and a radial passage, wherein the radial passage extends to the second side and the axial passage extends longitudinally along the length of the hollow member. The radial passage may have an outlet forming one of said one or more apertures.

The hollow member may comprise a substantially cylindrical outer surface (e.g., except for the one or more apertures the outer surface forms a cylinder) and the axial passage may extend from a first axial end of the cylinder to a second axial end of the cylinder. The inlet conduit may be inserted into the first end of the cylinder and the matrix conduit may be inserted into the second end of the cylinder.

The inlet conduit and/or the matrix conduit and/or the axial passage may be coaxial with respect to one another.

The inlet of the inlet conduit and an outlet of the matrix conduit may be located within the cavity or passage and oppose one another, and the outlet may be spaced at a distance x from the inlet of the inlet conduit, wherein x may be greater than, less than or equal to about 0 mm, about 0.5 mm, about 1 mm, about 1.5 mm, about 2 mm, about 2.5 mm, about 3 mm, about 3.5 mm, about 4 mm, about 4.5 mm or about 5 mm and optionally between about 3 mm and 4 mm.

The radial passage may meet the axial passage at a junction, and in use aerosol, smoke or vapour may pass through the radial passage and into the axial passage before passing into the inlet of the inlet conduit.

If a matrix conduit is provided, then at some point the aerosol, smoke or vapour will mix with the matrix emerging from the matrix conduit. This depends on the position of the matrix conduit within the axial passage. The matrix conduit may comprise an outlet end. If this outlet end is located within the axial passage before the junction, then matrix emerging from the matrix conduit and the aerosol, smoke or vapour will initially mix at said junction.

If the outlet end is located within the axial passage and past the junction, then the aerosol, smoke or vapour may be arranged and adapted to travel around the matrix conduit (e.g., coaxially) and mix with matrix emerging from the matrix conduit past the junction.

The matrix conduit may be inserted into the inlet conduit of the ion analyser or mass spectrometer. For example, an outer diameter of the matrix conduit may be less than the inner diameter of the inlet conduit. In this case the aerosol, smoke or vapour would travel around the matrix conduit (e.g., coaxially) within the axial passage as well as within the inlet conduit, and then mix with the aerosol, smoke or vapour within the inlet conduit.

The matrix conduit and/or inlet conduit and/or axial passage may have an inner and/or outer diameter of (i) about 0.01 to 0.02 mm; (ii) about 0.02-0.03 mm; (iii) about 0.03-0.04 mm; (iv) about 0.04-0.05 mm; (v) about 0.05-0.06 mm; (vi) about 0.06-0.07 mm; (vii) about 0.07-0.08 mm; (viii) about 0.08-0.09 mm; (ix) about 0.1-0.2 mm; (x) about 0.2-0.3 mm; (xi) about 0.3-0.4 mm; (xii) about 0.5-0.6 mm; (xiii) about 0.6-0.7 mm; (xiv) about 0.7-0.8 mm; (xv) about 0.8-0.9 mm; (xvi) about 0.9-1 mm; (xvii) about 1-2 mm; (xviii) about 2-3 mm; (xix) about 3-4 mm; (xx) about 4-5 mm or (xxi) >5 mm.

The matrix conduit and/or the inlet conduit and/or the cavity or passage may be aligned substantially co-axially with one another.

The Venturi pump arrangement may comprise an elongated portion having an outlet through which the aerosol, smoke or vapour passes, and the elongated portion may have a longitudinal axis that may be perpendicular, or substantially perpendicular to a longitudinal axis be of the cavity or passage and/or the inlet conduit and/or the matrix conduit.

The first device may comprise an ambient ion source.

The target may comprise native or unmodified target material.

The native or unmodified target material may be unmodified by the addition of a matrix or reagent.

The first device may be arranged and adapted to generate aerosol, smoke or vapour from one or more regions of the target without the target requiring prior preparation.

The first device may comprise an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysmay be Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) probe electrospray ionisation ("PESI") ion source; (xix) a solid-probe assisted electrospray ionisation ("SPA-ESI") ion source; (xx) a cavitron ultrasonic surgical aspirator ("CUSA") ion source; (xxi) a focussed or unfocussed ultrasonic ablation ion source; (xxii) a microwave resonance ion source; and (xxiii) a pulsed plasma RF dissection device.

The first device may comprise one or more electrodes arranged and adapted to generate the aerosol, smoke or vapour from one or more regions of the target.

The one or more electrodes may comprise a bipolar device or a monopolar device.

The one or more electrodes may comprise a rapid evaporation ionization mass spectrometry ("REIMS") device.

The apparatus may further comprise a voltage source arranged and adapted to apply an AC or RF voltage to the one or more electrodes in order to generate the aerosol, smoke or vapour.

The voltage source may be arranged and adapted to apply one or more pulses of the AC or RF voltage to the one or more electrodes.

The step of applying the AC or RF voltage to the one or more electrodes may cause heat to be dissipated into the target.

The first device may comprise a laser source and a device for irradiating the target with laser light from the laser source to generate the aerosol, smoke or vapour.

The first device may be arranged and adapted to generate an aerosol from one or more regions of the target by direct evaporation or vaporisation of target material from the target by Joule heating or diathermy.

The first device may comprise a transducer arranged and adapted to direct ultrasonic energy into the target in order to generate the aerosol, smoke or vapour.

The aerosol may comprise uncharged aqueous droplets optionally comprising cellular material.

At least 50%, 55%, 60%, 65%, 70%, 75%, 80%, 85%, 90% or 95% of the mass or matter generated by the first device and which forms the aerosol may be in the form of droplets.

The first device may be arranged and adapted to generate aerosol wherein the Sauter mean diameter ("SMD", d32) of the aerosol may be in a range: (i)<5 μm; (ii) 5-10 μm; (iii) 10-15 μm; (iv) 15-20 μm; (v) 20-25 μm; or (vi) >25 μm.

The aerosol may traverse a flow region with a Reynolds number (Re) in the range: (i)<2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i)<50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number ($S_k$) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i)<20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

The target may comprise a sample containing organic compounds. The target may comprise organic synthetic or semi-synthetic compounds and/or may comprise one or more polymers, for example plastic or rubber.

References to a sample or sample portion herein may refer to a sample containing organic compounds, or a sample comprising organic synthetic or semi-synthetic compounds and/or may comprise one or more polymers, for example plastic or rubber.

The target may comprise biological tissue, biologic matter, a bacterial colony or a fungal colony. References to biological tissue herein may refer to biologic matter, a bacterial colony or a fungal colony.

The biological tissue may comprise human tissue or non-human animal tissue.

The biological tissue may comprise in vivo biological tissue, biologic matter, bacterial colony or fungal colony.

The biological tissue may comprise ex vivo biological tissue, biologic matter, bacterial colony or fungal colony.

The biological tissue may comprise in vitro biological tissue, biologic matter, bacterial colony or fungal colony.

The biological tissue may comprise: (i) adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The first device may comprise a point of care ("POC"), diagnostic or surgical device.

The ion analyser or mass spectrometer may be arranged and adapted to ionise at least some of the aerosol, smoke or vapour so as to generate analyte ions.

The apparatus may further comprise an inlet device arranged and adapted to direct at least some of the aerosol, smoke or vapour into a vacuum chamber of an ion analyser or spectrometer.

The ion analyser or mass spectrometer may be arranged and adapted to ionise at least some of the aerosol, smoke or vapour within a or the vacuum chamber of the ion analyser or mass spectrometer so as to generate a plurality of analyte ions.

The apparatus may further comprise a collision surface located within a or the vacuum chamber arranged and adapted such that the aerosol, smoke or vapour may be caused to impact upon the collision surface so as to generate a plurality of analyte ions.

The apparatus may further comprise a mass analyser and/or ion mobility analyser arranged and adapted to mass analyse or ion mobility analyse the analyte ions in order to obtain mass spectrometric and/or ion mobility data.

The apparatus may further comprise a mass analyser and/or ion mobility analyser arranged and adapted to mass analyse or ion mobility analyse the aerosol, smoke or vapour or ions derived from the aerosol, smoke or vapour in order to obtain mass spectrometric and/or ion mobility data.

The apparatus may further comprise control means arranged and adapted to analyse the mass spectrometric and/or ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances may be present in the target; (vi) to confirm the identity or authenticity of the target; (vii) to determine whether or not one or more impurities, illegal substances or undesired substances may be present in the target; (viii) to determine whether a human or animal patient may be at an increased risk of suffering an adverse outcome; (ix) to make or assist in the making a diagnosis or prognosis; and (x) to inform a surgeon, nurse, medic or robot of a medical, surgical or diagnostic outcome.

The apparatus may further comprise a processing device arranged and adapted to analyse the mass spectrometric and/or ion mobility data by performing a supervised multivariate statistical analysis of the mass spectrometric and/or ion mobility data.

Either: (i) the multivariate statistical analysis may comprise principal component analysis ("PCA"); (ii) the multivariate statistical analysis may comprise linear discriminant analysis ("LDA"); (iii) the multivariate statistical analysis may be performed by a neural network; (iv) the multivariate statistical analysis may be performed by a support vector machine; or (v) the multivariate statistical analysis may comprise subspace discriminant analysis.

The processing device may be arranged and adapted to analyse the mass spectrometric and/or ion mobility data by analysing a profile of the aerosol, smoke or vapour or a profile of ions derived from the aerosol, smoke or vapour The profile may be selected from the group consisting of: (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; (viii) a phosphatidylinositol (PI) profile; or (ix) a triglyceride (TG) profile.

According to an aspect there is provided an apparatus comprising:

a first device for generating aerosol, smoke or vapour from one or more regions of a target;

a device arranged and adapted to mix said aerosol, smoke or vapour with said matrix or solvent in order to create a mixture of particles of said aerosol, smoke or vapour and said matrix, wherein said device comprises:

a first conduit arranged and adapted to receive said aerosol, smoke or vapour from said first device;

a second conduit arranged and adapted to receive a matrix conduit or tube, wherein said matrix conduit is arranged and adapted to supply a matrix or solvent from a source of matrix or solvent to said device; and a third conduit arranged and adapted to receive an inlet tube for transferring a mixture of said matrix or solvent and said aerosol, smoke or vapour to an ion analyser or mass spectrometer.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The apparatus may comprise said matrix conduit and/or said inlet tube. The first conduit, second conduit and third conduit may be in fluid communication with one another.

The device may comprise or form a hollow member, and said hollow member may comprise a single-piece of material having one or more internal cavities or passages forming said first conduit, said second conduit and said third conduit.

The first conduit may be arranged orthogonal to said second conduit and/or said third conduit. The first conduit may meet the second conduit and/or the third conduit at a junction. In use, sample may pass from the first conduit to the third conduit via said junction, before being passed (or drawn) into said inlet tube.

At some point the aerosol, smoke or vapour will mix with the matrix emerging from the matrix conduit. This depends on the position of the matrix conduit within the device.

The matrix conduit may comprise an outlet end. If this outlet end is located within the device and before the junction (i.e., within the second conduit and before the first conduit meets the second conduit), then matrix emerging from the matrix conduit and the aerosol, smoke or vapour will initially mix at said junction.

If the outlet end is located within the device and past the junction (i.e., within the third conduit and after the first conduit meets the third conduit), then the aerosol, smoke or vapour may be arranged and adapted to travel around the matrix conduit (e.g., coaxially) and mix with matrix emerging from the matrix conduit past the junction.

The matrix conduit may be inserted into the inlet tube. For example, an outer diameter of the matrix conduit may be less than the inner diameter of the inlet tube. In this case the aerosol, smoke or vapour would travel around the matrix conduit (e.g., coaxially and/or through a gap between the outer surface of the matrix conduit and the surface of the third conduit and/or junction) within the third conduit as well as within the inlet tube, and then mix with the aerosol, smoke or vapour within the inlet tube.

The matrix conduit and/or inlet tube and/or first conduit and/or second conduit and/or third conduit may have an inner and/or outer diameter of (i) about 0.01 to 0.02 mm; (ii) about 0.02-0.03 mm; (iii) about 0.03-0.04 mm; (iv) about 0.04-0.05 mm; (v) about 0.05-0.06 mm; (vi) about 0.06-0.07 mm; (vii) about 0.07-0.08 mm; (viii) about 0.08-0.09 mm; (ix) about 0.1-0.2 mm; (x) about 0.2-0.3 mm; (xi) about 0.3-0.4 mm; (xii) about 0.5-0.6 mm; (xiii) about 0.6-0.7 mm; (xiv) about 0.7-0.8 mm; (xv) about 0.8-0.9 mm; (xvi) about 0.9-1 mm; (xvii) about 1-2 mm; (xviii) about 2-3 mm; (xix) about 3-4 mm; (xx) about 4-5 mm or (xxi) >5 mm.

The third conduit may be in fluid communication with a first vacuum chamber of the ion analyser or mass spectrometer.

Aerosol, smoke or vapour may be drawn, in use, into said first conduit by the inherent vacuum of the ion analyser or mass spectrometer. Matrix or solvent may be drawn, in use, into said second conduit by the inherent vacuum of the ion analyser or mass spectrometer.

The first conduit may meet the second conduit and the third conduit at a or the junction, and an outlet end of the matrix conduit may be located within the third conduit and after the junction, such that, in use, said aerosol, smoke or vapour may travel around the matrix conduit (e.g., through a gap between the outer surface of the matrix conduit and the surface of the third conduit and/or junction) and mix with matrix emerging from the matrix conduit past said junction and at said outlet end of the matrix conduit.

The matrix conduit may be a matrix tube or matrix introduction tube.

According to another aspect there is provided apparatus comprising:

a first device for generating aerosol, smoke or vapour from one or more regions of a target;

an inlet conduit to an ion analyser or mass spectrometer;

an aerosol, smoke or vapour introduction conduit which may be arranged and adapted to direct the aerosol, smoke or vapour at the inlet conduit; and a matrix introduction conduit which may be arranged and adapted to direct a matrix (or solvent) at the inlet conduit.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The aerosol, smoke or vapour introduction conduit may be aligned substantially co-axially with the matrix introduction conduit.

The aerosol, smoke or vapour introduction conduit may be located concentrically within or about the matrix introduction conduit. The matrix introduction conduit may be located concentrically around the aerosol, smoke or vapour introduction conduit.

The combination of the matrix introduction conduit and the aerosol, smoke or vapour introduction conduit may form a Venturi pump configured to draw and nebulise the aerosol, smoke or vapour from the aerosol, smoke or vapour introduction conduit.

The apparatus may further comprise a pump arranged and adapted to pump the matrix past or around the aerosol, smoke or vapour introduction conduit at a flow rate of greater than 1 ml/min, 1.5 ml/min, 2 ml/min, 2.5 ml/min or 3 ml/min.

The aerosol, smoke or vapour introduction conduit and/or the matrix introduction conduit may be arranged and adapted to direct the aerosol, smoke or vapour and/or the matrix orthogonally past the inlet conduit. Aerosol, smoke or vapour may be drawn, in use, into said inlet conduit by the inherent vacuum of the ion analyser or mass spectrometer. Matrix or solvent may be drawn, in use, into said inlet conduit by the inherent vacuum of the ion analyser or mass spectrometer.

The matrix introduction conduit and/or inlet conduit and/or first conduit and/or aerosol, smoke or vapour introduction conduit may have an inner and/or outer diameter of (i) about 0.01 to 0.02 mm; (ii) about 0.02-0.03 mm; (iii) about 0.03-0.04 mm; (iv) about 0.04-0.05 mm; (v) about 0.05-0.06 mm; (vi) about 0.06-0.07 mm; (vii) about 0.07-0.08 mm; (viii) about 0.08-0.09 mm; (ix) about 0.1-0.2 mm; (x) about 0.2-0.3 mm; (xi) about 0.3-0.4 mm; (xii) about 0.5-0.6 mm; (xiii) about 0.6-0.7 mm; (xiv) about 0.7-0.8 mm; (xv) about 0.8-0.9 mm; (xvi) about 0.9-1 mm; (xvii) about 1-2 mm; (xviii) about 2-3 mm; (xix) about 3-4 mm; (xx) about 4-5 mm or (xxi) >5 mm.

According to another aspect there is provided apparatus comprising:

a first device for generating aerosol, smoke or vapour from one or more regions of a target;

a Venturi pump arrangement arranged and adapted to direct the aerosol, smoke or vapour towards a junction;

an inlet conduit having an inlet located at the junction and arranged and adapted to transfer the aerosol, smoke or vapour to an ion analyser or mass spectrometer;

a matrix introduction conduit arranged and adapted to introduce a matrix or solvent into the junction or said inlet conduit.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

In use, the particles of the aerosol, smoke or vapour may mix with the matrix or solvent at the junction or within the inlet conduit.

The Venturi pump arrangement may comprise a sample transfer portion arranged and adapted to direct the aerosol, smoke or vapour towards the junction.

The sample transfer portion may be elongated, and may have a longitudinal axis and may be arranged and adapted such that, in use, aerosol, smoke or vapour is directed along the longitudinal axis.

The inlet conduit may be located or positioned orthogonally with respect to the sample transfer portion.

The matrix introduction conduit may be located or positioned orthogonally with respect to the sample transfer portion.

The matrix introduction conduit may have a first longitudinal axis, the inlet conduit may have a second longitudinal axis, and the first longitudinal axis may be parallel to the second longitudinal axis.

The matrix introduction conduit may have an outlet through which matrix passes in use, and the position of the outlet with respect to the inlet of the inlet conduit may be adjustable.

The distance between the outlet of the matrix introduction conduit and the inlet of the inlet conduit may be between 0-10 mm, 2-8 mm, 2-6 mm or 2-4 mm.

The outlet may be positioned within the inlet conduit, such that aerosol, smoke or vapour may be arranged and adapted to travel around the matrix introduction conduit (e.g., coaxially and/or through a gap between the outer surface of the matrix introduction conduit and the inner surface of the inlet conduit) and mix with matrix emerging from the matrix conduit within the inlet conduit.

The matrix introduction conduit and/or inlet conduit and/or sample transfer portion may have an inner and/or outer diameter of (i) about 0.01 to 0.02 mm; (ii) about 0.02-0.03 mm; (iii) about 0.03-0.04 mm; (iv) about 0.04-0.05 mm; (v) about 0.05-0.06 mm; (vi) about 0.06-0.07 mm; (vii) about 0.07-0.08 mm; (viii) about 0.08-0.09 mm; (ix) about 0.1-0.2 mm; (x) about 0.2-0.3 mm; (xi) about 0.3-0.4 mm; (xii) about 0.5-0.6 mm; (xiii) about 0.6-0.7 mm; (xiv) about 0.7-0.8 mm; (xv) about 0.8-0.9 mm; (xvi) about 0.9-1 mm; (xvii) about 1-2 mm; (xviii) about 2-3 mm; (xix) about 3-4 mm; (xx) about 4-5 mm or (xxi) >5 mm.

In use, particles of the aerosol, smoke or vapour may intermix with particles of the matrix within the inlet conduit so as to form molecules comprising the molecular constituents of both particles of the aerosol, smoke or vapour and particles of the matrix.

The apparatus may further comprise a collision surface, wherein, in use, the molecules comprising the molecular constituents of both particles of the aerosol, smoke or vapour and particles of the matrix may be accelerated or otherwise directed onto the collision surface so as to form analyte ions.

The apparatus may further comprise a heater or heating device arranged and adapted to heat the collision surface.

The collision surface may be located within a vacuum chamber.

The vacuum chamber may form part of the ion analyser or mass spectrometer.

According to another aspect there is provided apparatus comprising:

a first device arranged and adapted to emit a stream of electrically charged droplets towards a target in use;

a transfer capillary arranged and adapted to transfer ions generated from the target towards an ion analyser or mass spectrometer; and a heating device arranged and adapted to heat either: (i) a capillary of the first device; (ii) the stream of electrically charged droplets emitted from the first device; (iii) the target; or (iv) the transfer capillary.

The ion analyser or mass spectrometer may comprise a mass spectrometer and/or a mass to charge ratio spectrometer and/or ion mobility spectrometer. The ion analyser may comprise a tandem mass spectrometer and ion mobility spectrometer system.

The first device may comprise a Desorption Electrospray Ionisation ("DESI") device.

The heating device may comprise a heater.

The heater may comprise a wire heater.

The heating device may be arranged and adapted to heat the capillary of the first device, the stream of electrically charged droplets emitted from the first device, the target or the transfer capillary to a temperature above ambient temperature, and/or to a temperature of at least 30° C., 50° C., 100° C., 200° C., 300° C., 400° C., 500° C. or greater than 500° C.

The heating device may be located adjacent an inlet to the ion analyser or mass spectrometer.

The inlet may form the entrance to a first vacuum stage of the ion analyser or mass spectrometer.

According to another aspect there is provided a method of introducing ions into an ion analyser or mass spectrometer, comprising:

producing ions by Desorption Electrospray Ionisation ("DESI"); and transferring the ions into a mass spectrometer or analyser via a heated capillary.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The method may further comprise heating the capillary to a temperature above ambient temperature, and/or to a temperature of at least 30° C., 50° C., 100° C., 200° C., 300° C., 400° C., 500° C. or greater than 500° C.

The step of producing ions may comprise desorbing ions from a biologic sample, wherein the sample may comprise lipids. The sample may comprise or further comprise carbohydrates, enzymes, hormones, fatty acids, neurotransmitters, nucleic acids, proteins, peptides, amino acids, lectins, vitamins, fats and oils.

The sample may comprise phospholipids.

According to another aspect there is provided apparatus comprising:

a first device for generating aerosol, smoke or vapour from one or more regions of a target;

a portable apparatus comprising one or more stacks of instruments, wherein each of the one or more stacks of instruments may comprise one or more wheels or tracks for facilitating movement thereof; and an ion analyser or mass spectrometer carried by one of the one or more stacks of instruments and connected in use to the first device.

The ion analyser or mass spectrometer may comprise a mass spectrometer and/or a mass to charge ratio spectrometer and/or ion mobility spectrometer. The ion analyser may comprise a tandem mass spectrometer and ion mobility spectrometer system.

The one or more stacks of instruments may be operatively connected to an endoscope comprising the first device.

The endoscope may comprise one or more gas channels or ports located at least partially along its length, wherein the gas channels may be arranged and adapted to transfer the aerosol, smoke or vapour to the ion analyser or mass spectrometer.

The apparatus may further comprise a first endoscope control system arranged and adapted to control the endoscope, and a second control system arranged and adapted to control the first device.

The first control system may comprise a first monitor arranged and adapted to display images relayed from a distal end of the endoscope.

The second control system may comprise a second monitor arranged and adapted to display data or information output from the ion analyser or mass spectrometer.

The first and second monitors could be located on orconsist of a mobile device, for example a mobile tablet device.

The first and second monitors may be the same component.

The ion analyser or mass spectrometer and the endoscope control system may be carried by the same stack of instruments.

Each of the one or more stacks of instruments may weigh less than 500 kg, 400 kg, 300 kg, 200 kg, 150 kg, 100 kg, 50 kg, 40 kg, 30 kg, 20 kg, 10 kg or 5 kg.

According to another aspect there is provided surgical apparatus comprising apparatus as disclosed above.

The apparatus may further comprise a set of operating theatres and a track or rail between each of the operating theatres, wherein the wheels or tracks on the one or more stacks of instruments may be configured to move along the track or rail to allow movement of the one or more stacks of instruments between each operating theatre.

According to another aspect there is provided apparatus comprising:

a first device for generating aerosol, smoke or vapour from one or more regions of a target, wherein the first device may be arranged and adapted for surgical use.

The first device may comprise one or more electrodes arranged and adapted to contact a sample to generate the aerosol, smoke or vapour.

The one or more electrodes may have a length less than 20 mm, 15 mm, 10 mm or 5 mm.

The one or more electrodes may have a surface area less than 200 mm$^2$, 100 mm$^2$, 50 mm$^2$, 40 mm$^2$, 30 mm$^2$, 20 mm$^2$ or 10 mm$^2$, 2 mm$^2$, 1 mm$^2$, 0.5 mm$^2$, 0.4 mm$^2$, 0.3 mm$^2$, 0.2 mm$^2$ or 0.1 mm$^2$.

The first device may comprise an internal passage for transferring aerosol, smoke or vapour generated by the one or more electrodes to an external device.

At least one of the one or more electrodes may comprise an aperture arranged and adapted such that the aerosol, smoke or vapour passes through the aperture in use, wherein the aperture may form the entrance to the internal passage.

The one or more electrodes may be sharpened towards a distal end, the distal end forming a contact area of the one or more electrodes.

The contact area may be defined as the surface area of the electrode that may be arranged and adapted to contact a sample in use.

The contact area may be defined as the surface area of the one or more electrodes within a distanced from the distal end of the one or more electrodes, wherein d may be 10 mm, 5 mm, 4 mm, 3 mm, 2 mm, 1 mm, 0.8 mm, 0.6 mm, 0.5 mm, 0.4 mm, 0.3 mm, 0.2 mm or 0.1 mm.

The contact area may be less than 200 mm$^2$, 100 mm$^2$, 50 mm$^2$, 40 mm$^2$, 30 mm$^2$, 20 mm$^2$ or 10 mm$^2$, 2 mm$^2$, 1 mm$^2$, 0.5 mm$^2$, 0.4 mm$^2$, 0.3 mm$^2$, 0.2 mm$^2$ or 0.1 mm$^2$.

The apparatus may further comprise a voltage supply arranged and adapted to supply a voltage to the one or more electrodes, wherein the voltage supply may have a voltage limit of less than 3 kV, 2.5 kV, 2 kV, 2.5 kV, 2 kV, 1.5 kV, 1 kV, 500 V, 400 V, 350 V, 300 V, 250 V, 200 V, 150 V, 100 V, 50 V, 20 V or 10 V peak or RMS.

The first device may comprise a single monopolar electrode arranged and adapted to generate the aerosol, smoke or vapour.

The first device may comprise dual bipolar electrodes arranged and adapted to generate the aerosol, smoke or vapour.

According to another aspect there is provided surgical apparatus comprising apparatus as disclosed above.

According to another aspect there is provided a method of using the apparatus as disclosed above comprising:

scanning the first device across one or more regions of a target;

determining whether one or more compounds of interest are present at one or more locations at the target; and guiding, modifying, initiating or stopping a surgical procedure based on whether the compound of interest may have been determined to be present.

The step of guiding, modifying, initiating or stopping a surgical procedure may comprise removing tissue present at the one or more locations if the compound is determined to be present at the locations.

The step of guiding, modifying, initiating or stopping a surgical procedure may comprise ceasing to remove tissue present at the one or more locations if the compound is not or no longer determined to be present at the locations.

According to another aspect there is provided a robotic surgery method comprising: providing a handheld manipulator which may be operatively coupled to a probe via one or more actuators;

manually moving the handheld manipulator;

automatically causing the one or more actuators to move the probe in response to movement of the handheld manipulator;

energising the probe so as to generate aerosol, smoke or vapour; and analysing the aerosol, smoke or vapour. The analysing may comprise mass analysing and/or ion mobility analysing and/or a combination of mass and ion mobility analysing.

According to another aspect there is provided apparatus comprising:

a user interface;

a robotic probe which is responsive to or controlled by the user interface, wherein the robotic probe is arranged to generate aerosol, smoke or vapour; and a mass analyser and/or ion mobility analyser for analysing or ion mobility analysing the aerosol, smoke or vapour. The analysing may comprise mass analysing and/or ion mobility analysing and/or a combination of mass and ion mobility analysing.

The user interface may comprise a handheld manipulator operatively coupled to the robotic probe to control movement thereof.

The user interface may be arranged and adapted such that, in use, movement of the handheld manipulator causes movement of the one or more actuators.

The robotic probe may comprise one or more electrodes arranged and adapted to generate analyte, smoke, fumes, liquid, gas, surgical smoke, aerosol or vapour when the probe is in contact with biological tissue, biologic matter, a bacterial colony or a fungal colony.

The probe may form part of a robotically-controlled endoscopic or laparoscopic device.

The endoscopic or laparoscopic device may comprise an endoscope and a camera at a distal end of the endoscope, wherein the camera may be arranged and adapted to transmit images to the user interface.

The robotic probe may be located at a distal end of the endoscopic or laparoscopic device.

The endoscopic or laparoscopic device may comprise one or more instrument channels or ports that travel at least partially along the endoscope, and the robotic probe may be operatively coupled to the user interface via one or more actuators located within the one or more instrument channels or ports.

The probe or endoscopic device or laparoscopic device may comprise a rapid evaporative ionisation mass spectrometry ("REIMS") electrosurgical tool comprising one or more electrodes.

The one or more electrodes may be arranged to generate the aerosol, smoke or vapour.

According to another aspect there is provided apparatus comprising:

a first device for generating aerosol, smoke or vapour from one or more regions of a target;

analysing the aerosol, smoke or vapour or ions derived from aerosol, smoke or vapour; and adjusting one or more ion-optic devices and/or altering one or more ion pathways in response to the analysis.

The analysing step may comprise determining whether a particular compound or compounds present in the aerosol, smoke or vapour exceeds or falls below a defined intensity threshold or limit.

The adjusting step may comprise adjusting the attenuation or otherwise adjusting the transmission of ions if the compound or compounds present in the aerosol, smoke or vapour exceed or fall below the defined intensity threshold or limit.

According to another aspect there is provided a laparoscopic tool comprising:

an elongated portion arranged and adapted for insertion into a human or animal body through an incision in the human or animal body; and a first device located at a distal end of the elongated portion, wherein the first device may be arranged and adapted to generate aerosol, smoke or vapour from tissue located within the human or animal body.

The elongated portion may have a maximum lateral dimension or width less than 20 mm, 15 mm, 10 mm or 5 mm.

The elongated portion may have a length greater than 5 mm, 10 mm, 15 mm, 20 mm, 25 mm, 30 mm, 35 mm, 40 mm, 50 mm, 60 mm, 70 mm, 80 mm, 90 mm, 100 mm, 150 mm, 200 mm, 300 mm, 400 mm or 500 mm.

The laparoscopic tool may further comprise a handle arranged and adapted to aid in moving and/or guiding the laparoscopic tool.

The laparoscopic tool may further comprise an internal passage for transferring aerosol, smoke or vapour generated by the first device to an external device.

The first device may comprise an aperture arranged and adapted such that the aerosol, smoke or vapour passes through the aperture in use, wherein the aperture may form the entrance to the internal passage.

The first device may comprise one or more electrodes arranged and adapted to generate the aerosol, smoke or vapour when the probe may be in contact with the tissue.

According to another aspect there is provided a method of analysis comprising:

providing a tool comprising a first device located within a tubing or a housing, wherein the tubing or the housing may comprise a tool deployment opening and one or more separate aspiration ports;

using the first device to generate aerosol, smoke or vapour from one or more regions of a target; and obtaining chemical or other data from the one or more regions of the target.

The first device may comprise one or more electrodes.

The one or more electrodes may comprise a snare, optionally wherein the snare comprises a polypectomy snare.

The one or more electrodes may comprise one or more hooks, one or more grabbers, one or more blades, one or more knives, one or more serrated blades, one or more probes, one or more biopsy tools, one or more robotic tools, one or more pincers, one or more electrosurgical pencils, one or more forceps, one or more bipolar forceps, one or more coagulation devices, one or more irrigation devices and one or more imaging tools.

The one or more electrodes may comprise a monopolar device.

The method may further comprise providing a separate return electrode.

The one or more electrodes may comprise a bipolar device.

The one or more electrodes may comprise: (i) a monopolar device, wherein the apparatus optionally further comprises a separate return electrode; (ii) a bipolar device; or (iii) a multi phase RF device, wherein the apparatus optionally further comprises a separate return electrode or electrodes.

According to another aspect there is provided apparatus comprising:

an ultrasonic scalpel, probe, aspirator or dissector for use in surgery and arranged and adapted to liquefy, disrupt or otherwise fragment tissue contacting the ultrasonic scalpel, probe, aspirator or dissector; and an analysis device arranged and adapted to analyse particles of the tissue, for example using an ambient ionisation technique.

The apparatus may further comprise an endoscope comprising the ultrasonic scalpel and a distal end for inserting into a human or animal body, wherein the ultrasonic scalpel may be located at the distal end.

The apparatus may further comprise an electrosurgical tool arranged and adapted to contact tissue to generate an aerosol, smoke or vapour, wherein the analysis device may comprise an ion analyser or mass spectrometer arranged and adapted to analyse the aerosol smoke or vapour.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The ultrasonic scalpel, probe, aspirator or dissector and the electrosurgical tool may be housed within or on the same component, for example an endoscope.

The ultrasonic scalpel, probe, aspirator or dissector may comprise an electrode, such that the ultrasonic scalpel, probe, aspirator or dissector may form the electrosurgical tool.

According to another aspect there is provided apparatus comprising:

a surgical laser arranged and adapted to generate an aerosol, smoke or vapour from a sample; and an ion analyser or mass spectrometer arranged and adapted to analyse the aerosol, smoke or vapour.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

According to another aspect there is provided a method comprising:

providing a surgical laser arranged and adapted to generate an aerosol, smoke or vapour from a sample;

scanning the surgical laser across one or more regions of the sample to generate aerosol, smoke or vapour; and transferring the aerosol, smoke or vapour generated at the one or more sample regions to an ion analyser or mass spectrometer.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The method may further comprise analysing the aerosol, smoke or vapour using an ambient ionisation technique.

The method may further comprise a control device arranged and adapted to control the frequency and/or power and/or energy and/or wavelength and/or pulse duration of the surgical laser.

The control system may be arranged and adapted to modify the frequency and/or power and/or energy and/or wavelength and/or pulse duration of the surgical laser in response to analysis of the aerosol, smoke or vapour by the ion analyser or mass spectrometer.

According to another aspect there is provided an electrosurgical tool or probe arranged and adapted:

to apply an electric current to a sample to cut, coagulate, desiccate or fulgurate the sample or a portion of the sample; and to capture particles from the portion of the sample that have been vapourised by the electrosurgical tool and transfer the particles to an analysis device.

The analysis device may comprise an ion analyser or mass spectrometer arranged and adapted to analyse the vapourised particles, for example using an ambient ionisation technique.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The electrosurgical tool may comprise a rapid evaporative ionization mass spectrometry device or probe.

The electrosurgical tool may comprise an electrode arranged and adapted to evaporate or vapourise the sample to form an aerosol, smoke or vapour.

The electrosurgical tool further may comprise a counter or return electrode arranged and adapted to contact the sample.

According to another aspect there is provided apparatus comprising:

a laparoscope comprising a first device for generating aerosol, smoke or vapour from one or more regions of a target; and one or more insufflation gas outlets for transferring an insufflation gas from a source of gas and into a human or animal body.

The apparatus may further comprise a control system arranged and adapted to control the flow of gas from the gas source to the gas outlets, wherein the control system may be arranged and adapted to modify the flow of gas based on analysis of the aerosol, smoke or vapour by an ion analyser or mass spectrometer.

The apparatus may further comprise an ion analyser or mass spectrometer arranged and adapted to analyse the aerosol, smoke or vapour using an ambient ionisation technique. The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The apparatus may further comprise an insufflation device comprising the source of insufflation gas and a or the control system arranged and adapted to control the flow of gas from the gas source to the gas outlets.

According to another aspect there is provided a method comprising:

providing a first device for generating aerosol, smoke or vapour from one or more regions of a sample;

scanning the first device across one or more regions of the sample to generate aerosol, smoke or vapour;

transferring the aerosol, smoke or vapour generated at the one or more sample regions to an ion analyser or mass spectrometer; and analysing the aerosol, smoke or vapour to determine the molecular constituents located at the one or more regions of the sample. The analysing may comprise mass analysing and/or ion mobility analysing and/or a combination of mass and ion mobility analysing.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

According to another aspect there is provided apparatus comprising:

a first device for generating aerosol, smoke or vapour from one or more regions of a sample, wherein the first device may comprise one or more electrodes arranged and adapted to apply a voltage to the one or more regions of the sample in order to generate the aerosol, smoke or vapour from one or more regions of the target, and wherein the electrodes have a largest dimension less than 5 cm, 2 cm, 1 cm, 5 mm, 2 mm, 1 mm, 0.5 mm or 0.1 mm.

The apparatus may further comprise a robot arranged and adapted to move the first device, or the one or more electrodes.

The robot may be arranged and adapted to move the first device, or the one or more electrodes in single movements that may be less than 10 mm, 5 mm, 4 mm, 3 mm, 2 mm, 1 mm, 0.5 mm, 0.4 mm, 0.3 mm, 0.2 mm or 0.1 mm.

The robot may be arranged and adapted to move the first device, or the one or more electrodes, in a stepped manner, wherein each step corresponds to a movement of less than 10 mm, 5 mm, 4 mm, 3 mm, 2 mm, 1 mm, 0.5 mm, 0.4 mm, 0.3 mm, 0.2 mm or 0.1 mm.

According to another aspect there is provided apparatus comprising:

a first device arranged and adapted to generate an aerosol, smoke or vapour from one or more regions of a target;

an ion analyser or mass spectrometer arranged and adapted to analyse the aerosol, smoke or vapour; and a transfer device arranged and adapted to transfer the aerosol, smoke or vapour to an inlet portion of the ion analyser or mass spectrometer, wherein the inlet portion may comprise an inlet to a first vacuum chamber of the ion analyser or mass spectrometer;

wherein the first device and the transfer device may be removable and/or replaceable from the ion analyser or mass spectrometer.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

According to another aspect there is provided apparatus comprising:

a first device arranged and adapted to generate an aerosol, smoke or vapour from one or more regions of a target;

a second device arranged and adapted to mix the aerosol, smoke or vapour with a matrix or solvent at a junction;

a third device for transferring the mixture of aerosol, smoke or vapour and the matrix or solvent to an ion analyser or mass spectrometer; and a transfer device arranged and adapted to transfer the aerosol, smoke or vapour to the junction;

wherein the first device and the transfer device may be removable and/or replaceable from the third device and the ion analyser or spectrometer.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The ion analyser or mass spectrometer may comprise a first vacuum chamber, and the third device may be arranged and adapted, in use, to be held at the same pressure as the first vacuum chamber.

In any of the aspects or embodiments disclosed herein, the matrix may comprise polar molecules, water, one or more alcohols, methanol, ethanol, isopropanol, acetone or acetonitrile. The matrix may comprise a lockmass or calibration compound.

According to another aspect there is provided a method comprising:

providing a surgical tool having an identification device, wherein the surgical tool may be arranged and adapted to generate an aerosol, smoke or vapour from one or more regions of a target; and setting or controlling operational parameters of the surgical tool in response to the identification device.

The identification device may comprise a Radio Frequency Identification ("RFID") tag.

The method may further comprise restricting use of the surgical tool to operational parameters indicated by the identification device.

The method may further comprise utilizing a database which may be restricted by or determined by the identification device.

The database may include tissue identification data which may be restricted by or determined by the identification device.

The operational parameter may comprise a power setting or a maximum power setting of the surgical tool.

The operational parameter may comprise a power duration or a power interval setting of the surgical tool.

The method may further comprise utilizing a statistical model or algorithm, wherein data contained on the identification device forms or comprises part of a parameter or input for the statistical model or algorithm.

The outcome of the model or algorithm may be used to determine operational parameters of the surgical tool, or instrument parameters of the analyser.

The method may further comprise setting operational parameters, for example optimal operational parameters, indicated by the identification device.

The operational parameters may include mass or mass to charge ratio range of a mass filter, operating mode of a mass spectrometer and/or ion mobility spectrometer (e.g., fragmentation, MS/MS, MS$^n$, etc.), ion-optical settings (for example resolution, transmission or attenuation), enhanced duty cycle, target ion current, trapping time, analysis time (e.g., resolution when using an orbitrap device), scan time or scan rates (e.g., coupled to a Time-of-Flight mass spectrometer), The method may further comprise setting a mode of operation of a mass spectrometer and/or ion mobility spectrometer and/or tandem mass spectrometer and ion mobility spectrometer system indicated by the identification device. For example, ion mobility separation could be enabled based on the information or data provided by the identification device.

Instead of ion mobility separation, or other devices, eg in the case of a trapping device, the target ion current, trapping time analysis time (resolution on orbitrap device) ion trap scan rates (eg coupled to ToF MS), or coupled to quad devices (eg could be parent ion scanning mode with high duty cycle)

The identification device may restrict the surgical tool to performing a limited number of procedures.

The identification device may restrict the surgical tool to performing a single procedure or a predefined number of procedures.

The identification device may impose an operational time limit upon the surgical tool.

The surgical tool may comprise a rapid evaporative ionisation mass spectrometry ("REIMS") device or probe.

According to another aspect there is provided apparatus comprising:

a surgical tool having an identification device, wherein the surgical tool may be arranged and adapted to generate an aerosol, smoke or vapour from one or more regions of a target.

The identification device may comprise a Radio Frequency Identification ("RFID") tag.

The apparatus may further comprise a controller wherein the controller may be arranged and adapted to communicate with and/or receive information from and/or interrogate the identification device.

The controller may be arranged and adapted to set or control operational parameters of the surgical tool in response to communicating with and/or receiving information from and/or interrogating the identification device.

The controller may be arranged and adapted to restrict use of the surgical tool to operational parameters indicated by the identification device.

The controller may be arranged and adapted to utilise a database which may be restricted by or determined by the identification device.

The database may include tissue identification data which may be restricted by or determined by the identification device.

The operational parameter may comprise a power setting or a maximum power setting of the surgical tool.

The operational parameter may comprise a power duration or a power interval setting of the surgical tool.

The controller may be arranged and adapted to utilize a statistical model or algorithm, wherein data contained on the identification device forms or comprises part of a parameter or input for the statistical model or algorithm.

The controller may be arranged and adapted to determine operational parameters of the surgical tool, or instrument parameters of the analyser using the outcome of the model or algorithm.

The identification device may restrict the surgical tool to performing a limited number of procedures.

The identification device may restrict the surgical tool to performing a single procedure or a predefined number of procedures.

The identification device may impose an operational time limit upon the surgical tool.

According to another aspect there is provided a method of treating a biologic sample, comprising:

identifying a first portion of the sample to be analysed;

vapourising or otherwise creating an aerosol, smoke or vapour from the first sample portion in a non-invasive or minimally invasive process;

analysing and/or ion mobility analysing the aerosol, smoke or vapour; and determining whether any compounds of interest are contained in the aerosol, smoke or vapour. The analysing may comprise mass analysing and/or ion mobility analysing and/or a combination of mass and ion mobility analysing.

The biologic sample and/or the first sample portion may comprise skin.

The non-invasive or minimally invasive process may create the aerosol, smoke or vapour from the sample portion by not penetrating more than 1 µm, 2 µm, 3 µm, 4 µm, 5 µm, 10 µm, 20 µm, 25 µm, 30 µm, 35 µm, 50 µm, 100 µm, 200 µm or 250 µm into the sample portion.

The method may further comprise applying a treatment to the first sample portion based on the type or amount of any compounds of interest that may be contained in the aerosol, smoke or vapour.

The method may further comprise removing tissue from the first sample portion based on the type or amount of any compounds of interest contained in the aerosol, smoke or vapour.

The method may further comprise, if the compounds of interest are contained (or not contained) in the aerosol, smoke or vapour, applying a treatment to the first sample portion and/or removing tissue from the first sample portion.

The method may further comprise, after the step of applying a treatment and/or removing tissue:

further vapourising or otherwise creating an aerosol, smoke or vapour from the first sample portion in a non-invasive or minimally invasive process;

analysing and/or ion mobility analysing the aerosol, smoke or vapour; and determining whether any compounds of interest may still be contained in the aerosol, smoke or vapour. The analysing may comprise mass analysing and/or ion mobility analysing and/or a combination of mass and ion mobility analysing.

The method may further comprise, after the step of determining whether any compounds of interest are still contained in the aerosol, smoke or vapour:

applying a treatment to the first sample portion and/or removing tissue from the first sample portion if either: (i) the compounds of interest are contained in the aerosol, smoke or vapour; or (ii) the compounds of interest are not contained in the aerosol, smoke or vapour; and/or ceasing to apply a treatment and/or remove tissue from the first sample portion if either: (i) the compounds of interest are contained in the aerosol, smoke or vapour; or (ii) the compounds of interest are not contained in the aerosol, smoke or vapour.

The method may further comprise, if either: (i) the compounds of interest are contained in the aerosol, smoke or vapour; or (ii) the compounds of interest are not contained in the aerosol, smoke or vapour, identifying a second portion of the sample to be analysed and carrying out the steps described above for the second sample portion.

Mass analysing (or mass analysing and/or ion mobility analysing and/or a combination of mass and ion mobility analysing) and/or ion mobility analysing the aerosol, smoke or vapour or analysing the spectrometric and/or ion mobility data may comprise analysing one or more sample spectra so as to classify an aerosol, smoke or vapour sample.

The one or more sample spectra may comprise one or more sample mass and/or mass to charge ratio and/or ion mobility (drift time) spectra. Ion mobility spectra may be obtained using different ion mobility drift gases, or dopants may be added to the drift gas to induce a change in drift time of one or more species. These spectra may then be combined or concatenated.

Analysing the one or more sample spectra so as to classify the aerosol, smoke or vapour sample may comprise supervised analysis of the one or more sample spectra and/or unsupervised analysis of the one or more sample spectra.

Analysing the one or more sample spectra so as to classify the aerosol, smoke or vapour sample may comprise using one or more of: univariate analysis; multivariate analysis;

principal component analysis (PCA); linear discriminant analysis (LDA); maximum margin criteria (MMC); library-based analysis; soft independent modelling of class analogy (SIMCA); factor analysis (FA); recursive partitioning (decision trees); random forests; independent component analysis (ICA); partial least squares discriminant analysis (PLS-DA); orthogonal (partial least squares) projections to latent structures (OPLS); OPLS discriminant analysis (OPLS-DA); support vector machines (SVM); (artificial) neural networks; multilayer perceptron; radial basis function (RBF) networks; Bayesian analysis; cluster analysis; a kernelized method; and subspace discriminant analysis.

Analysing the one or more sample spectra so as to classify the aerosol, smoke or vapour sample may comprise developing a classification model or library using one or more reference sample spectra.

Analysing the one or more sample spectra so as to classify the aerosol, smoke or vapour sample may comprise performing linear discriminant analysis (LDA) after performing principal component analysis (PCA).

Analysing the one or more sample spectra so as to classify the aerosol, smoke or vapour sample may comprise performing a maximum margin criteria (MMC) process after performing principal component analysis (PCA).

Analysing the one or more sample spectra so as to classify the aerosol, smoke or vapour sample may comprise defining one or more classes within a classification model or library.

Analysing the one or more sample spectra so as to classify the aerosol, smoke or vapour sample may comprise defining one or more classes within a classification model or library manually or automatically according to one or more class or cluster criteria.

The one or more class or cluster criteria for each class may be based on one or more of: a distance between one or more pairs of reference points for reference sample spectra within a model space; a variance value between groups of reference points for reference sample spectra within a model space; and a variance value within a group of reference points for reference sample spectra within a model space.

The one or more classes may be each defined by one or more class definitions.

The one or more class definitions may comprise one or more of: a set of one or more reference points for reference sample spectra, values, boundaries, lines, planes, hyperplanes, variances, volumes, Voronoi cells, and/or positions, within a model space; and one or more positions within a class hierarchy.

Analysing the one or more sample spectra so as to classify the aerosol, smoke or vapour sample may comprise using a classification model or library to classify one or more unknown sample spectra.

Analysing the one or more sample spectra so as to classify the aerosol, smoke or vapour sample may comprise classifying one or more sample spectra manually or automatically according to one or more classification criteria.

The one or more classification criteria may comprise one or more of:

a distance between one or more projected sample points for one or more sample spectra within a model space and a set of one or more reference points for one or more reference sample spectra, values, boundaries, lines, planes, hyperplanes, volumes, Voronoi cells, or positions, within the model space being below a distance threshold or being the lowest such distance;

a position for one or more projected sample points for one or more sample spectra within a model space being one side or other of one or more reference points for one or more reference sample spectra, values, boundaries, lines, planes, hyperplanes, or positions, within the model space;

a position for one or more projected sample points for one or more sample spectra within a model space being within one or more volumes or Voronoi cells within the model space; and a probability or classification score being above a probability or classification score threshold or being the highest such probability or classification score.

Various embodiments are contemplated which relate to generating smoke, aerosol or vapour from a target (details of which are provided elsewhere herein) using an ambient ionisation ion source. The aerosol, smoke or vapour may then be mixed with a matrix and aspirated into a vacuum chamber of a mass spectrometer and/or ion mobility spectrometer. The mixture may be caused to impact upon a collision surface causing the aerosol, smoke or vapour to be ionised by impact ionization which results in the generation of analyte ions. The resulting analyte ions (or fragment or product ions derived from the analyte ions) may then be mass analysed and/or ion mobility analysed and the resulting mass spectrometric data and/or ion mobility spectrometric data may be subjected to multivariate analysis or other mathematical treatment in order to determine one or more properties of the target in real time.

According to an embodiment the first device for generating aerosol, smoke or vapour from the target may comprise a tool which utilises an RF voltage, such as a continuous RF waveform.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to various embodiments the mass spectrometer and/or ion mobility spectrometer may obtain data in negative ion mode only, positive ion mode only, or in both positive and negative ion modes. Positive ion mode spectrometric data may be combined or concatanated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatonated.

It will be apparent that the requirement to add a matrix or a reagent directly to a sample may prevent the ability to perform in vivo analysis of tissue and also, more generally, prevents the ability to provide a rapid simple analysis of target material.

According to other embodiments the ambient ionisation ion source may comprise an ultrasonic ablation ion source or a hybrid electrosurgical-ultrasonic ablation source that generates a liquid sample which is then aspirated as an aerosol. The ultrasonic ablation ion source may comprise a focused or unfocussed ultrasound.

Optionally, the first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

BRIEF DESCRIPTION OF THE DRAWINGS

Various embodiments will now be described, by way of example only, and with reference to the accompanying drawings in which:

FIG. 1 illustrates the general principles of the rapid evaporative ionisation mass spectrometry technology disclosed herein, involving, for example, a method of rapid evaporative ionisation mass spectrometry ("REIMS") wherein an RF voltage is applied to bipolar forceps resulting in the generation of an aerosol or surgical plume which is then captured through an irrigation port of the bipolar forceps and is then transferred to a mass spectrometer and/or ion mobility spectrometer for mass and/or ion mobility analysis;

FIG. 4A shows a different inlet setup arrangement for an ion analyser or mass spectrometer according to another embodiment and comprising a T-junction arrangement for introducing aerosol and matrix and FIG. 4B shows in greater detail the T-junction arrangement of FIG. 4A;

FIG. 5A shows a modified version of the inlet setup arrangement shown in FIGS. 4A and 4B and includes a Venturi pump and FIG. 5B shows another embodiment which is similar to the embodiment shown in FIG. 5A except that a dedicated matrix introduction conduit is provided;

FIG. 9A shows a mass spectrum produced from *Bacteroides fragilis* at an isopropanol flow rate of 0.01 mL/min, FIG. 9B shows a mass spectrum produced from *Bacteroides fragilis* at an isopropanol flow rate of 0.02 mL/min, FIG. 9C shows a mass spectrum produced from *Bacteroides fragilis* at an isopropanol flow rate of 0.05 mL/min, FIG. 9D shows a mass spectrum produced from *Bacteroides fragilis* at an isopropanol flow rate of 0.0.07 mL/min, FIG. 9E shows a mass spectrum produced from *Bacteroides fragilis* at an isopropanol flow rate of 0.1 mL/min, FIG. 9F shows a mass spectrum produced from *Bacteroides fragilis* at an isopropanol flow rate of 0.13 mL/min, FIG. 9G shows a mass spectrum produced from *Bacteroides fragilis* at an isopropanol flow rate of 0.15 mL/min, FIG. 9H shows a mass spectrum produced from *Bacteroides fragilis* at an isopropanol flow rate of 0.2 mL/min, and FIG. 9I shows a mass spectrum produced from *Bacteroides fragilis* at an isopropanol flow rate of 0.25 mL/min;

FIG. 11 shows a Desorption Electrospray Ionisation ("DESI") device according to another embodiment;

FIG. 13C shows an embodiment of a laparoscopic device that may be used in the apparatus of FIGS. 13A and 13B;

FIG. 16 shows an embodiment of a surgical tool for use in the various embodiments and methods disclosed herein;

FIG. 17 shows an embodiment of a surgical tool for use in the various embodiments and methods disclosed herein;

DETAILED DESCRIPTION

Figure 2A:
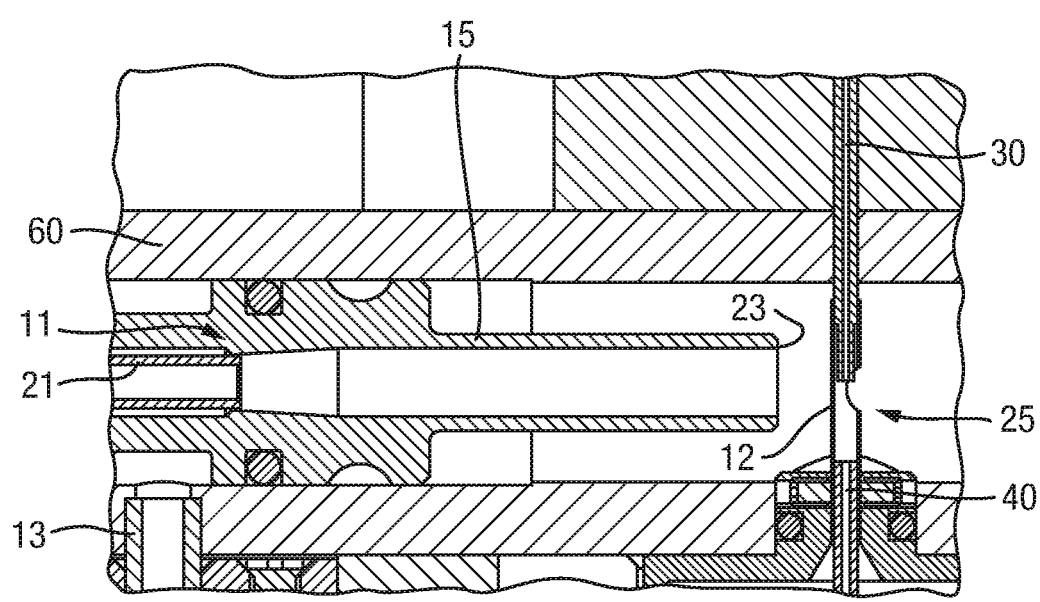
FIG. 2A shows an inlet setup for an ion analyser or mass spectrometer according to an embodiment and shows a Venturi pump arrangement which is arranged to direct aerosol particles towards an inlet conduit of an ion analyser or mass spectrometer.

Various embodiments are described below which relate to apparatus and methods for the chemical analysis of aerosols and gaseous samples containing analytes using mass spectrometry and/or ion mobility spectrometry or other gas-phase ion analysis modalities.

The embodiments disclosed herein may relate to the use of an electrosurgical tool, for example a device or probe such as a rapid evaporative ionisation mass spectrometry ("REIMS") device or probe that may be provided in the form of a surgical diathermy probe. The rapid evaporative ionisation mass spectrometry device or probe may comprise one or more electrodes configured to evaporate or vapourise biologic tissue to form an aerosol, surgical smoke or vapour comprising particles of the biologic tissue. The rapid evaporative ionisation mass spectrometry device or probe may further comprise a tube or other means for transferring the particles to a mass analyser and/or ion mobility analyser and/or mass spectrometer and/or ion mobility spectrometer. Various configurations of such a device or probe are possible.

Embodiments are disclosed in which alternative means are provided to create the aerosol, surgical smoke or vapour. For example, an ultrasound device or probe is described in relation to FIG. 16 and a laser device or probe is described in relation to FIG. 17.

Various embodiments disclosed herein relate to the use of the probes in surgical or other situations, such as an operating theatre or battlefield. Further embodiments disclosed herein relate to apparatus that enable or benefit from the use of such probes, such as a surgical robot which can be guided using information provided by the devices and probes disclosed herein.

Further embodiments are disclosed in which the probes are incorporated into surgical equipment such as an endoscope and laparoscope.

Other embodiments relate more generally to ambient ionisation ion source.

Various other embodiments are contemplated and disclosed herein.

Ambient Ionisation Ion Sources

Although various embodiments as described herein are described in the context of using a rapid evaporative ionisation mass spectrometry ("REIMS") ion source comprising an electrosurgical tool, other embodiments are contemplated wherein other devices may be used to generate an aerosol, smoke or vapour from one or more regions of a target (e.g., in vivo tissue).

Ambient ionisation is a form of ionisation in which ions are formed in an ion source outside a mass spectrometer without sample preparation or separation. Ions can be formed by extraction into charged electrospray droplets, thermally desorbed and ionised by chemical ionisation or laser desorbed or ablated and post-ionised before they enter the mass spectrometer.

The devices or ion sources may comprise ambient ionisation ion sources which are characterised by the ability to generate analyte aerosol, smoke or vapour from a native or unmodified target. By way of contrast, other types of ionisation ion sources such as Matrix Assisted Laser Desorption Ionisation ("MALDI") ion sources require the addition of a matrix, solvent or reagent to the sample prior to ionisation. As a result of the requirement to prepare a sample, such as a tissue sample, by adding a matrix, solvent or reagent to the sample prior to ionisation, ionisation ion sources such as Matrix Assisted Laser Desorption Ionisation ("MALDI") ion sources are not used to ionise native or unmodified samples.

It will be readily apparent that the requirement to add a matrix or a reagent to a sample prevents both in vivo analysis of tissue and rapid simple analysis of many other types of target material. It is recognised, therefore, that the ability of ambient ionisation ion sources to ionise a sample without requiring e.g. the addition of a solvent to the sample is particularly advantageous.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (i.e. untreated or unmodified) samples. A particular advantage of the various ambient ionisation techniques which are intended to fall within the scope of the present invention is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques which are intended to fall within the scope of the present invention are given in the following table:

| Acronym | Ionisation technique |
| --- | --- |
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |

| Acronym | Ionisation technique |
|---|---|
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate an aerosol or plume of surgical smoke by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a CO$_2$ laser having a wavelength of 10.6 µm may be used to generate the aerosol, smoke or vapour.

According to other embodiments the ambient ionisation ion source may comprise an ultrasonic ablation ion source which generates a liquid sample which is then aspirated as an aerosol. The ultrasonic ablation ion source may comprise a focused or unfocussed source.

According to an embodiment the first device for generating aerosol, smoke or vapour from one or more regions of a target may comprise an electrosurgical tool which utilises a continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

However, it will be appreciated that numerous other ambient ion sources may be utilised. For example, according to another embodiment the ambient ionisation ion source may comprise a laser ionisation ion source. A laser probe is disclosed herein and with reference to FIG. 17. According to an embodiment the laser ionisation ion source may comprise a mid-IR laser ablation ion source. For example, there are several lasers which emit radiation close to or at the 2.94 µm peak in the water absorption spectrum. According to various embodiments the ambient ionisation ion source may comprise a laser ablation ion source having a wavelength close to 2.94 µm (e.g., between 2.84 and 3.04 µm) on the basis of the high absorption coefficient of water at 2.94 µm, or the laser source described in relation to FIG. 17 may comprise a laser arranged and adapted to emit light having a wavelength close to 2.94 µm (e.g., between 2.84 and 3.04 µm), on the basis of the high absorption coefficient of water at 2.94 µm. According to an embodiment the laser ablation ion source may comprise a Er:YAG laser which emits radiation at 2.94 µm.

According to another embodiment the laser ablation ion source may comprise a laser, for example a carbon dioxide laser, and may emit radiation at between 10-11 µm or 10.4-10.8 µm, for example about 10.6 µm.

According to other embodiments the ambient ionisation ion source may comprise an ultrasonic ablation ion source. The ultrasonic ablation ion source may comprise a focused or unfocussed source. An example of an ultrasonic probe is described herein with reference to FIG. 16.

Rapid Evaporative Ionisation Mass Spectrometry ("REIMS")

FIG. 1 illustrates a method of rapid evaporative ionisation mass spectrometry ("REIMS") wherein bipolar forceps 1 may be brought into contact with in vivo tissue 2 of a patient 3. In the example shown in FIG. 1, the bipolar forceps 1 may be brought into contact with brain tissue 2 of a patient 3 during the course of a surgical operation on the patient's brain. An RF voltage from an RF voltage generator 4 may be applied to the bipolar forceps 1 which causes localised Joule or diathermy heating of the tissue 2. As a result, an aerosol or surgical plume 5 is generated.

The aerosol or surgical plume 5 may then be captured or otherwise aspirated through an irrigation port of the bipolar forceps 1. The irrigation port of the bipolar forceps 1 is therefore reutilised as an aspiration port. The aerosol or surgical plume 5 may then be passed from the irrigation (aspiration) port of the bipolar forceps 1 to tubing 6 (e.g. ⅛" or 3.2 mm diameter Teflon® tubing). The tubing 6 is arranged to transfer the aerosol or surgical plume 5 to an atmospheric pressure interface 7 of an ion analyser or mass spectrometer 8.

The ion analyser or mass spectrometer 8 may comprise a mass spectrometer and/or a mass to charge ratio spectrometer and/or an ion mobility spectrometer. The ion analyser may comprise a tandem mass spectrometer and ion mobility spectrometer system.

According to various embodiments a matrix comprising an organic solvent such as isopropanol may be added to the aerosol or surgical plume 5 at the atmospheric pressure interface 7. The mixture of aerosol 3 and organic solvent may then be arranged to impact upon a collision surface within a vacuum chamber of the ion analyser or spectrometer 8.

According to one embodiment the collision surface may be heated. The aerosol is caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour 5 to impact upon the collision surface are then passed through subsequent stages of the ion analyser or spectrometer and may be subjected to mass analysis in a mass analyser and/or ion mobility analysis in an ion mobility analyser. The mass analyser may, for example, comprise a quadrupole mass analyser or a Time of Flight mass analyser.

Figure 14A:
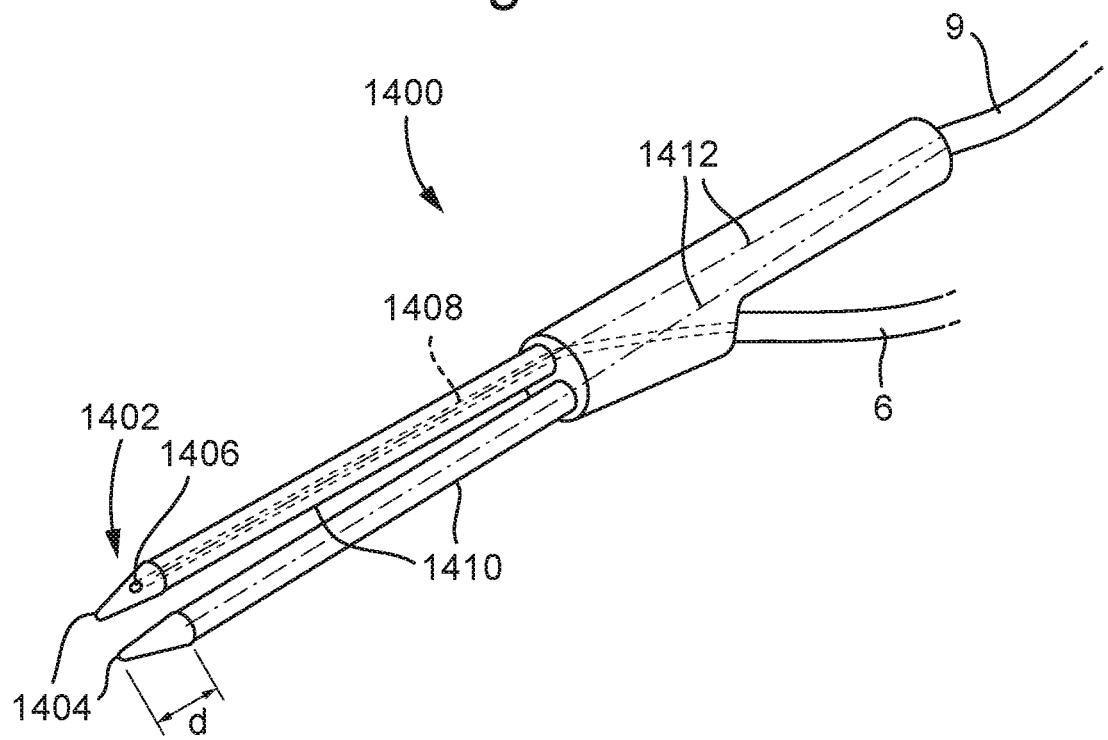
FIG. 14A shows an embodiment of an electrosurgical tool for use in the various embodiments and methods disclosed herein and FIG. 14B shows an embodiment of an electrosurgical tool for use in the various embodiments and methods disclosed herein.
Figure 14B:
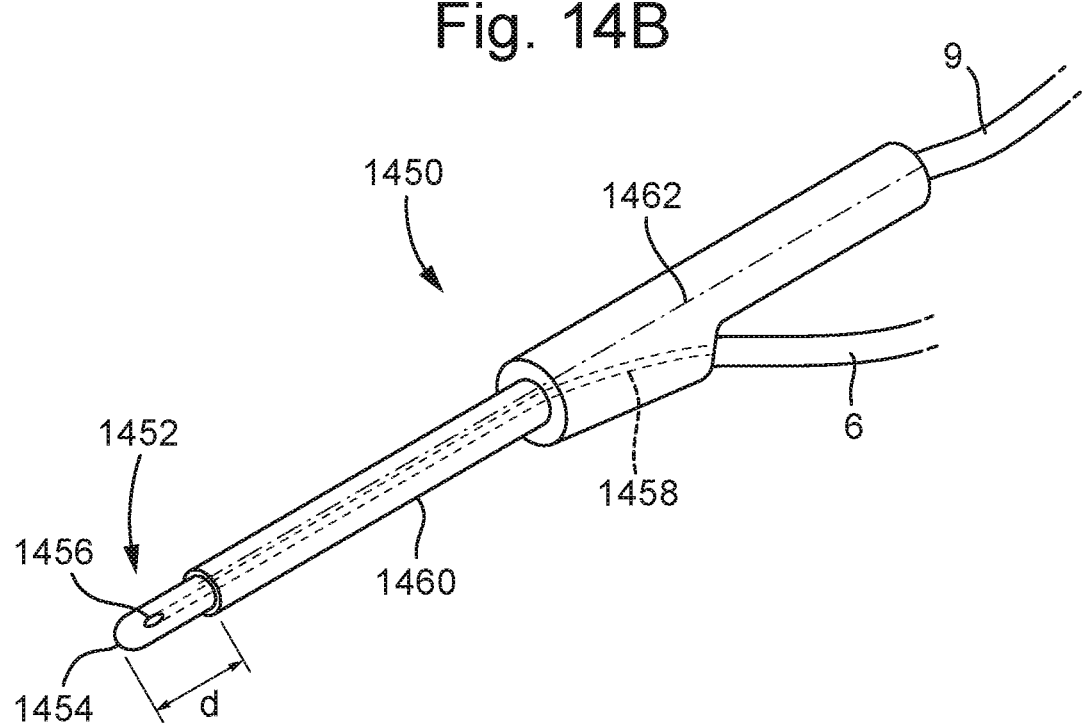

FIG. 14A shows one embodiment of suitable bipolar forceps 1400 and this is discussed in more detail below. An alternative embodiment is shown in FIG. 14B in which an RF voltage is applied to a monopolar device 1450.

In order to form a path for current, the apparatus used in respect of the monopolar device may involve a counter electrode placed at a suitable location on the sample. This is also discussed in more detail below.

Inlet Instrumentation

Various embodiments are concerned with the introduction of aerosol, smoke or vapour or other gaseous sample containing an analyte into an enclosed space, where the sample may be mixed with a low molecular weight matrix compound. According to an embodiment the sample may be mixed with an organic solvent such as isopropanol. This homogeneous or heterogeneous mixture may then be introduced into the atmospheric interface of an ion analyser or mass spectrometer and/or ion mobility spectrometer.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

Aerosol particles containing molecular constituents of the sample and the matrix compound (if present) are formed upon introduction of the mixture into the low pressure regime of the analytical instrument. The mixed composition aerosol particles may subsequently be dissociated via collisions with a solid collision surface. According to an embodiment the aerosol particles may be ionised by colliding with a collision surface located within a vacuum chamber of an ion analyser or mass spectrometer. The dissociation events produce neutral and charged species, including the molecular ions of the chemical constituents of the sample. The molecular ions are then subjected to mass or mobility analysis.

This provides a simple solution for the analysis of molecular constituents of aerosols in an on-line fashion, for example without the application of high voltages or lasers.

Inlet Setup #1—Venturi Pump

Figure 2B:
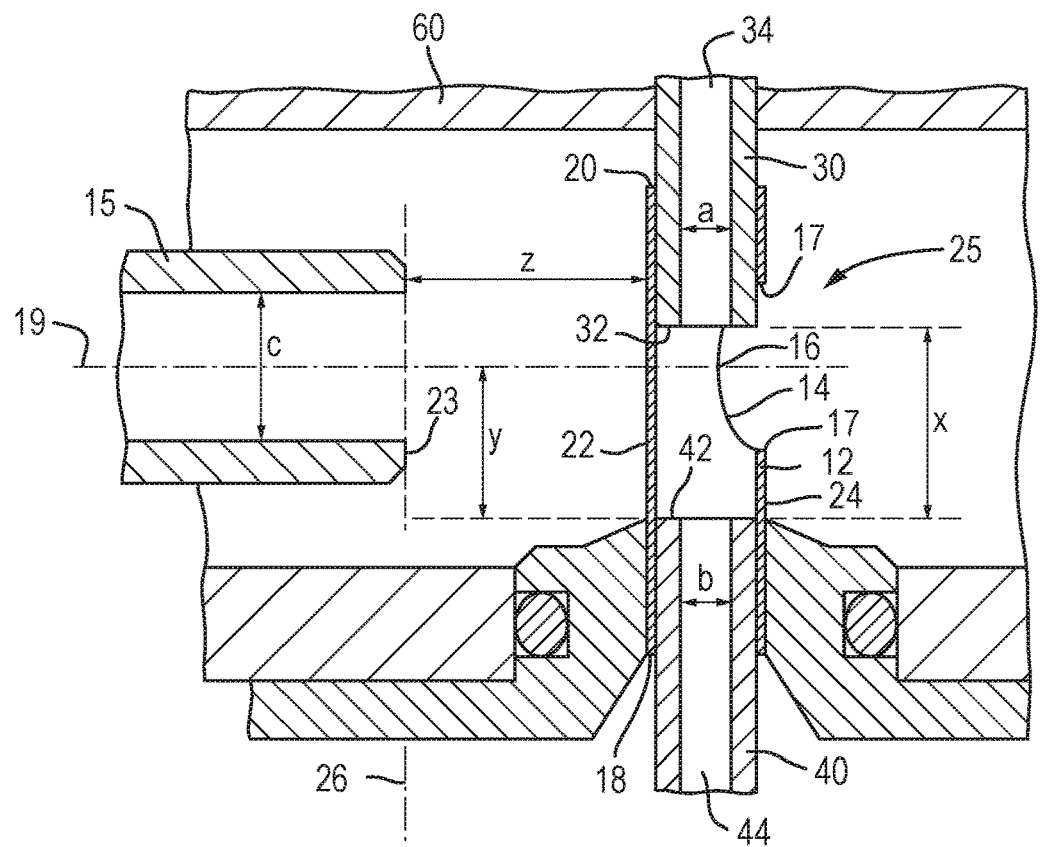
FIG. 2B shows a close-up of a sampling device which includes a whistle arrangement, wherein the sampling device is arranged to introduce a mixture of aerosol particles and matrix into an ion analyser or mass spectrometer
Figure 2C:
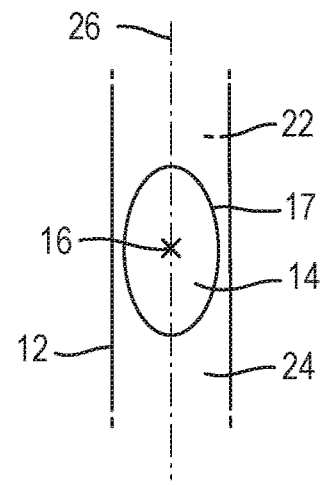
FIG. 2C shows a view of the whistle arrangement of the sampling device shown in FIG. 2B in isolation from the other features of the sampling device.

An inlet setup arrangement according to an embodiment is shown in FIGS. 2A-2C.

FIG. 2A shows an inlet setup arrangement or apparatus comprising a Venturi pump 11. The Venturi pump 11 optionally comprises a tube 21 that may be connected to a device or probe (e.g., a rapid evaporative ionisation mass spectrometry device or probe as described herein) and may be configured to transport aerosol particles from a sample (e.g., biologic tissue) to the Venturi pump 11. The Venturi pump 11 may comprise a gas inlet 13 that may be arranged and adapted to introduce a gas (e.g., a Venturi gas) into the flow path of the aerosol particles being transported into the Venturi pump 11 by the tube 21. The Venturi pump 11 may comprise a sample transfer tube 15 in the form of an elongated member or portion that may be arranged and adapted to transfer the sample and gas mixture from the tube 21 onto a sampling device 25 via an outlet end 23 of the sample transfer tube 15.

The sampling device 25 may broadly comprise a hollow tube or whistle 12, a matrix introduction conduit 30 and an inlet tube 40. The hollow tube or whistle 12 may be referred to as a deflection device.

The matrix introduction conduit 30 may be arranged and adapted to introduce a matrix in liquid form through a channel 34 (FIG. 2B) within the matrix introduction conduit 30. Matrix leaves the matrix introduction conduit 30 through an end 34 disposed or located within the whistle 12 and it may be nebulised by a gas that is being drawn into the inlet tube 40. The quality of nebulisation of the matrix may be controlled and affected by the dimensions and/or relative distances between the various parts of the sampling device 10, as described in more detail below.

The inlet tube 40 leads to an inlet of an ion analyser or mass spectrometer and may be arranged and adapted such that a mixture of sample, gas and matrix passes through an end 42 of the inlet tube 40 disposed or located within the whistle 12 and through a passage 44 to be transferred into a ion analyser or mass spectrometer.

The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

FIG. 2B shows a close-up view of the sampling device 10.

The whistle 12 may be provided in the form of a hollow tube optionally having a first side 22 that may be arranged so as to face the outlet end 23 of the sample transfer tube 15, and a second, opposite side 24 optionally facing away from the outlet end 23 of the sample transfer tube 15.

The whistle 12 may comprise a first end 18 that may be located concentrically around the inlet tube 40 and may be in sealing engagement therewith. The whistle may comprise a second end 20 that may be located concentrically around the matrix introduction conduit 30 and may be in sealing engagement therewith. An axial passage may extend from the first axial end 18 to the second axial end 20.

A void, aperture or cut-out 14 may be provided on the second side 24 of the whistle 12, and the cut-out 14 may form an inlet such that the sample and gas mixture flowing past the whistle 12 from the outlet end 23 of the sample transfer tube 15 may transfer into the interior of the whistle 12, for example the axial passage therein. The void, aperture or cut-out 14 may form the entrance to a radial passage fluidly connecting the axial passage to the region adjacent the second side 24 of the whistle 12.

The mixture of sample and gas exiting the outlet end 23 of the sample transfer tube 15 may impact on the first side 22 of the whistle 12, and then travel around the outside surface and into the cut-out 14. Once the sample and gas mixture is in the interior of the whistle, it may mix with the nebulised matrix emerging from the matrix introduction conduit 30 before the mixture of sample, gas and matrix is optionally transferred into the inlet tube 40 through the end 42 of the inlet tube 40. The mixture of sample, gas and matrix may then be transferred via the passage 44 to a ion analyser or mass spectrometer.

Positioning the cut-out 14 on the second side 24 of the whistle 12 means that the initial impact of the sample and gas mixture is on a surface that is not directly exposed to the vacuum (or decreased pressure region) of the ion analyser or mass spectrometer. In various embodiments, therefore, the sampling device 25 may be arranged and adapted such that the initial impact of the sample and gas mixture is on a surface that is not directly exposed to the vacuum (or decreased pressure region) of the ion analyser or mass spectrometer.

The cut-out 14 may have a semi-circular profile when the whistle 12 is viewed in cross-section (as shown, for example, in FIGS. 2A and 2B). This will mean that the edge 17 of the cut-out 14 is oval when viewed from a direction facing the second side 24 of the whistle 12 (see FIG. 2C). Alternatively, the cut-out 14 may have a different shape profile when the whistle 12 is viewed in cross-section, for example a square, triangular or irregular shaped profile. The edge 17 of the cut-out 14 may also be square, triangular or irregular when then whistle 12 is viewed from a direction facing the second side 24 of the whistle 12 (see FIG. 2C).

The position and orientation of the whistle 12 can affect the quantity and quality of sample that is transferred into the mass spectrometer. The cut-out 14 may comprise a centre point 16 which may be in line with a longitudinal centreline 19 of the sample transfer tube 15. FIG. 2C shows a view of the second side 24 of the whistle 12 (the whistle 12 is shown in isolation in FIG. 2C), and the centre point 16 can be seen as the centre point of the oval.

The whistle 12 may be oriented such that longitudinal axis 26 of the whistle lies coincident with an axis of symmetry of the cut-out 14. The centre point 16 may lie on the longitudinal axis 26 of the whistle 12 and/or an axis of symmetry of the cut-out. The axis of symmetry of the cut-out may comprise the longitudinal axis of symmetry, wherein the longitudinal direction may be defined as the direction along the longitudinal axis 26.

The position of the various parts of the sampling device 25 can also affect the quantity and quality of sample that is transferred into the mass spectrometer.

Now referring to FIG. 2B, a distance x is defined as the distance (e.g., the shortest distance) between the end 32 of the matrix introduction conduit 30 and the end 42 of the inlet tube 40.

A distance y is defined as the distance (e.g., the shortest distance) between the centre point 16 of the cut-out 14 and the end 42 of the inlet tube 40.

A distance z is defined as the distance (e.g., the shortest distance) between the outlet end 23 of the sample transfer tube 15 and the whistle 12 (e.g., the first side 22 of the whistle 12).

The diameter a of the matrix introduction conduit 30 can also affect the quantity and quality of sample that is transferred into the mass spectrometer, and can also affect the nebulisation of the matrix as it leaves the end of the matrix introduction conduit 30.

The diameter b of the inlet tube 40, and the diameter c of the sample transfer tube 15 can also affect the quantity and quality of sample that is transferred into the mass spectrometer.

The diameters a, b and c may correspond to the diameters at the end 32 of the matrix introduction conduit 30, the end 42 of the inlet tube and the outlet end 23 of the sample transfer tube 15, respectively.

Any or all of the diameters a, b and c may be greater than, less than or substantially equal to (i) about 0.01 to 0.02 mm; (ii) about 0.02-0.03 mm; (iii) about 0.03-0.04 mm; (iv) about 0.04-0.05 mm; (v) about 0.05-0.06 mm; (vi) about 0.06-0.07 mm; (vii) about 0.07-0.08 mm; (viii) about 0.08-0.09 mm; (ix) about 0.1-0.2 mm; (x) about 0.2-0.3 mm; (xi) about 0.3-0.4 mm; (xii) about 0.5-0.6 mm; (xiii) about 0.6-0.7 mm; (xiv) about 0.7-0.8 mm; (xv) about 0.8-0.9 mm; (xvi) about 0.9-1 mm; (xvii) about 1-2 mm; (xviii) about 2-3 mm; (xix) about 3-4 mm; (xx) about 4-5 mm or (xxi) >5 mm.

Any or all of the diameters/distances a, b, c, x, y and z may be changed to optimise the quantity and quality of sample that is transferred into the ion analyser or mass spectrometer.

The matrix introduction conduit (30) and/or inlet tube (40) and/or axial passage may have an inner and/or outer diameter of (i) about 0.01 to 0.02 mm; (ii) about 0.02-0.03 mm; (iii) about 0.03-0.04 mm; (iv) about 0.04-0.05 mm; (v) about 0.05-0.06 mm; (vi) about 0.06-0.07 mm; (vii) about 0.07-0.08 mm; (viii) about 0.08-0.09 mm; (ix) about 0.1-0.2 mm; (x) about 0.2-0.3 mm; (xi) about 0.3-0.4 mm; (xii) about 0.5-0.6 mm; (xiii) about 0.6-0.7 mm; (xiv) about 0.7-0.8 mm; (xv) about 0.8-0.9 mm; (xvi) about 0.9-1 mm; (xvii) about 1-2 mm; (xviii) about 2-3 mm; (xix) about 3-4 mm; (xx) about 4-5 mm or (xxi) >5 mm.

Aspects of the disclosure may extend to methods of optimising the sampling device 10, comprising identifying one or more parameters associated with the sampling device, for example ion abundance or ion signal intensity and changing one or more of the distances a, b, c, x, y and z until the one or more parameters are optimised or at a maximum or minimum value.

The Venturi pump 11 may be for introducing aerosol particles into the sample transfer tube 15. The sampling device 25 may be provided for sampling the aerosol. The matrix introduction conduit 30 may be arranged to introduce a matrix (such as isopropanol) into the sampling device 25 and the inlet tube 40 may be arranged to direct a mixture of aerosol particles and matrix onwards to an ion analyser or mass spectrometer.

The Venturi pump 11 may facilitate the aspiration of aerosol or other gaseous sample containing the analyte and may be driven by nitrogen or standard medical air. Aerosol sampling may be arranged to occur orthogonally to the outlet end 23 of the Venturi pump 11 as shown from FIGS. 2A and 2B. The outlet 32 of the matrix introduction conduit 30 may be spaced apart from the inlet tube 40 to the ion analyser or mass spectrometer by the distance x. The distance x can be modified as required to achieve an optimum ion signal intensity.

Altering the value of the distance x can change the velocity of the gas being drawn into the inlet tube 40 and can have an effect upon the nebulisation conditions. If the nebulisation conditions are less favourable then the matrix droplets may not be of the correct size for interacting with the analyte aerosol and/or may not fragment efficiently when the aerosol collides with a collision surface.

The matrix may include polar molecules, water, one or more alcohols, methanol, ethanol, isopropanol, acetone or acetonitrile. Isopropanol has been found to be particularly advantageous.

The inlet setup as shown in FIGS. 2A-2C may according to other embodiments be used without introducing a matrix. For example, according to an embodiment the matrix introduction conduit 30 may be removed or blocked. This may provide a direct aerosol introduction into the ion analyser or mass spectrometer.

However, introduction of a matrix (such as isopropanol) has been found to aid ionisation by partially or fully desolvating analyte molecules and also by reducing intermolecular forces which would otherwise negatively affect ionisation and thus reduce sensitivity.

Figure 3:
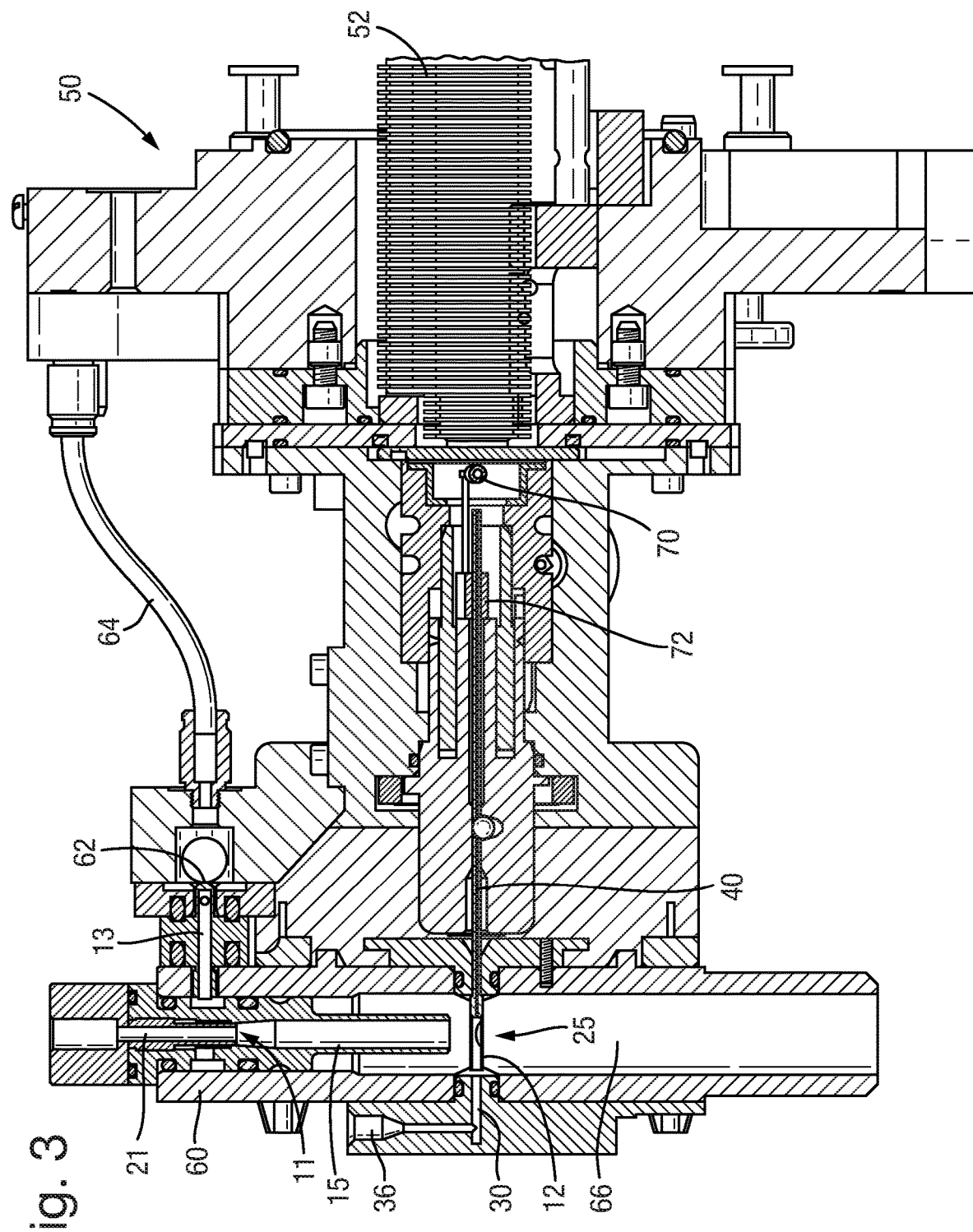
FIG. 3 shows in greater detail the overall inlet setup arrangement shown in FIGS. 2A-2C as connected to the initial stages of an ion analyser or mass spectrometer.

FIG. 3 shows in greater detail the inlet setup as shown in apparatus of FIGS. 2A-2C and connected to an ion analyser or mass spectrometer 50. In the illustrated example, the ion analyser or mass spectrometer 50 comprises an ion guide 52 (e.g. a Stepwave® ion guide), although any type of ion analyser or mass spectrometer may be provided as appropriate.

The apparatus may comprise a housing 60 arranged and adapted to house the Venturi pump 11. A matrix inlet port 36 may be provided for connection to a supply of matrix (e.g., isopropanol) and this may be in fluid communication with the matrix introduction conduit 3.

A gas connection 62 may be provided that may be in fluid communication via a gas line 64 with a source of aspirating gas such as nitrogen or standard medical air. The gas connection 62 may be in fluid communication with the gas line 3.

The apparatus may comprise an exhaust 66 for collecting the larger particles of sample that are not transferred into the whistle 12. A filter, for example a high efficiency particulate air ("HEPA") filter may be arranged and adapted to filter gases and other matter passed through the exhaust 66.

As described above, the mixture of sample, gas and matrix may be transferred from the sampling device 25 and through the inlet tube 40 and may emerge from the inlet tube 40 and impact upon a collision surface 70. The collision surface 70 may be heated, for example by an inductive or resistive heater. A further heater 72 may be provided to heat the mixture of sample, gas and matrix ("mixed composition") as it travels along the inlet tube 40. Heating the mixture can ensure that the matrix is in the form of droplets that can effectively bind to the sample. The heater 72 may be an inductive or resistive heater and may comprise a conductive metal (e.g., tungsten) wrapped around the inlet tube 40.

The mixed composition aerosol particles or analyte may be arranged to be ionised by impacting the collision surface 70. The resulting analyte ions may then be passed into the ion guide 52. The ion guide 52 may be arranged to separate analyte ions from neutral flux or background gas in a known manner.

Inlet Setup #2—T-Junction

Figure 4B:
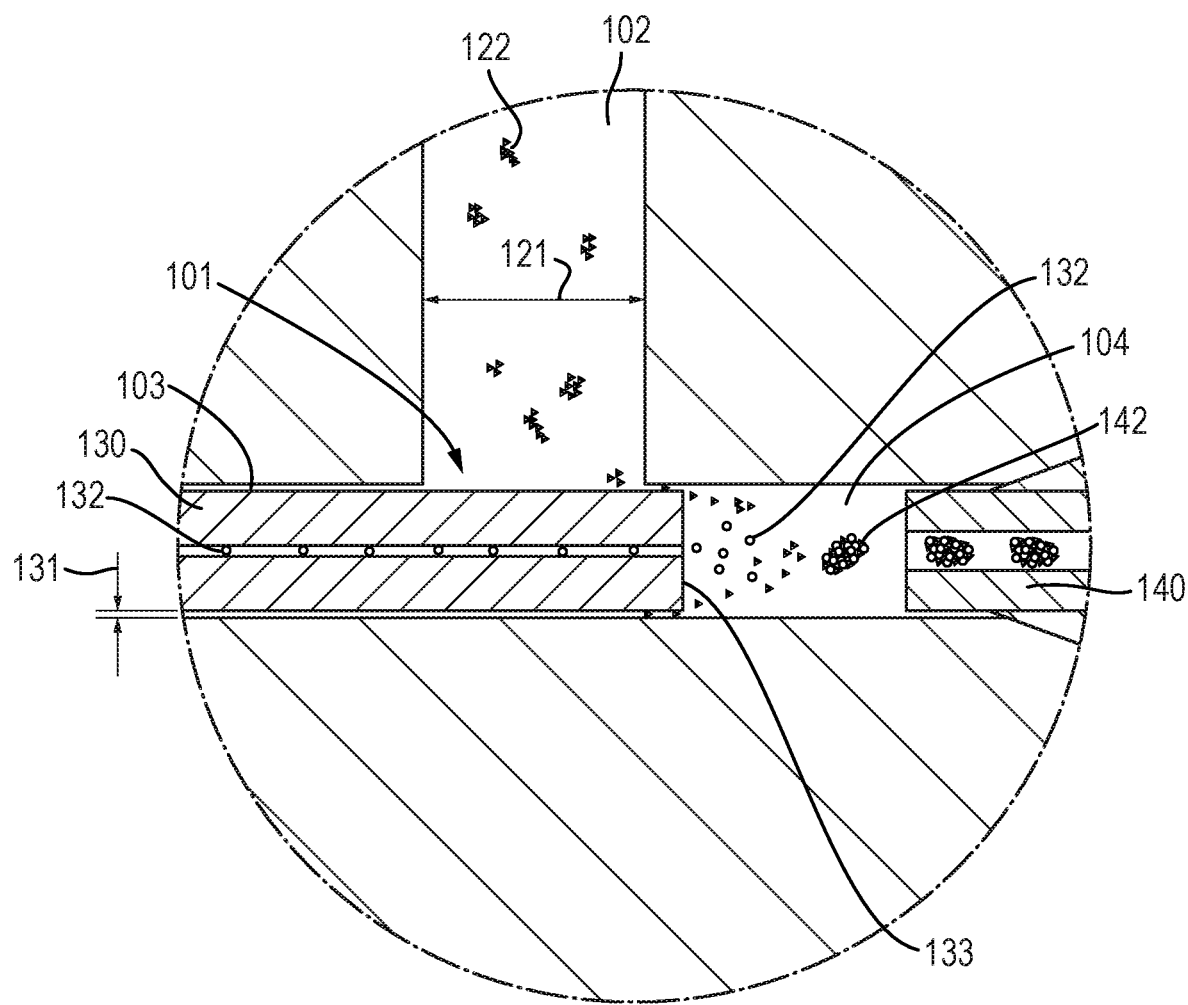

FIGS. 4A and 4B show an apparatus for introducing an aerosol mixture into an ion analyser or mass spectrometer 110 with a T-junction arrangement. In contrast to the arrangement shown in FIGS. 2A-2C, the T-junction arrangement may employ a direct mixing approach (i.e., without use of a Venturi pump) using a T-junction or device 100.

The apparatus may comprise an ion analyser or mass spectrometer 110. The ion analyser or mass spectrometer may comprise a mass spectrometer and/or a mass to charge ratio spectrometer and/or an ion mobility spectrometer. The ion analyser may comprise a tandem mass spectrometer and ion mobility spectrometer system.

The ion analyser or mass spectrometer 110 may comprise an inlet 112 and a decreased pressure region 114 (e.g., a first vacuum region). A collision surface 116 (e.g., a solid collision surface) and optionally ion optics 118 may be arranged within the decreased pressure region 114. The ion optics 118 may comprise an ion guide, for example a Stepwave® ion guide.

The apparatus may include a sample transfer tube 120 that may be connected to a device or probe (e.g., a rapid evaporative ionisation mass spectrometry device or probe as described herein) and may be configured to transport aerosol particles 122 (FIG. 4B) from a sample (e.g., biologic tissue) to the T-junction 100.

The sample transfer tube 120 may be fluidly sealed to the T-junction 100. For example, the sample transfer tube 120 may be fluidly sealed to a first conduit 102 of the T-junction 100, optionally at a sample connecting portion 125 located at the end of the first arm 102. Any mechanism for fluidly sealing the sample transfer tube 120 and the T-junction 100 may be used, for example a clamp 126 may be located around the sample transfer tube 120 at the sample connecting portion 125, and the clamp 126 may be sealed against the walls of the sample connecting portion 125, for example using an interference fit. The sample transfer tube 120 may be removable and/or replaceable from or with the T-junction 100.

In alternative embodiments, the sample transfer tube 120 may be contiguous with the T-junction 100, for example the first conduit 102 of the T-junction.

The apparatus may comprise a matrix introduction conduit 130 arranged and adapted to introduce a matrix or matrix compound 132 into the T-junction 100. The matrix introduction conduit 130 may be connected to a source (not shown) of matrix, for example isopropanol.

The matrix introduction conduit 130 may be fluidly sealed to the T-junction 100. For example, the matrix introduction conduit 130 may be fluidly sealed to a second conduit 103 of the T-junction 100, optionally at a matrix connecting portion 135 located at the end of the second conduit 103. Any mechanism for fluidly sealing the matrix introduction conduit 130 and the T-junction 100 may be used, for example a clamp 136 may be located around the matrix introduction conduit 130 at the matrix connecting portion 135, and the clamp 136 may be sealed against the walls of the matrix connecting portion 135, for example using an interference fit. The matrix introduction conduit 130 may be removable and/or replaceable from or with the T-junction 100.

In alternative embodiments, the matrix introduction conduit 130 may be contiguous with the T-junction 100, for example the second conduit 103 of the T-junction.

The apparatus may comprise an inlet tube or capillary 140 which may be in fluid communication with the mass spectrometer 110, for example the decreased pressure region 114 thereof. The connection between the inlet tube 140 and the mass spectrometer 110 is pictured schematically, and may take any form. In some embodiments, the inlet tube 140 is removable and/or replaceable from or with the mass spectrometer 110, for example the decreased pressure region 114 thereof.

The inlet tube 140 may be fluidly sealed to the T-junction 100. For example, the inlet tube 140 may be fluidly sealed to a third conduit 104 of the T-junction 100, optionally at a mass spectrometer connecting portion 145 located at the end of the third arm 104. Any mechanism for fluidly sealing the inlet tube 140 and the T-junction 100 may be used, for example a clamp 146 may be located around the inlet tube 140 at the mass spectrometer connecting portion 145, and the clamp 146 may be sealed against the walls of the mass spectrometer connecting portion 146, for example using an interference fit. The inlet tube 140 may be removable and/or replaceable from or with the T-junction 100.

In alternative embodiments, the inlet tube 140 may be contiguous with the T-junction 100, for example the third conduit 104 of the T-junction.

The T-junction 100 may comprise a single-piece of material, for example plastic, polyethylene, polycarbonate, polyvinyl chloride ("PVC") or polytetrafluoroethylene ("PTFE"). The T-junction 100 comprises the first conduit 102, second conduit 103 and third conduit 104 which all meet at a central junction 101.

As shown in FIG. 4B, the matrix introduction conduit 130 may be inserted into the second conduit 103 by any amount as required. Optionally, the matrix introduction conduit 130 is inserted such that it travels past the junction 101, for example into the third conduit 104.

It is envisaged that the matrix introduction conduit 130 may be inserted further into the third conduit 104, and may even be inserted into the inlet tube 140. To be able to be inserted into the inlet tube 140, the matrix introduction conduit 130 should have an outer diameter (or maximum dimension) smaller than the inner diameter of the inlet tube 140.

Aerosol particles 122 may travel along the first conduit 102 and may meet the matrix 132 particles at the junction 101 or in the third conduit 104 (depending on the position of the outlet end 133 of the matrix introduction conduit 130). At this point, the aerosol particles 122 may intermix with the matrix 132 and may form matrix molecules 142 in which both the molecular constituents of the aerosol particles 122 and the matrix 132 may be present. The matrix 132 may be in excess compared to the molecular constituents of the aerosol particles 122.

An outer diameter or dimension of the matrix introduction conduit 130 may be such that a gap 131 exists between the outer surface of the matrix introduction conduit 130 and the surfaces of the second conduit 103 and/or junction 101 and/or third conduit 104. In use, aerosol particles 122 may travel around the gap 131 and exit the gap 131 so as to surround the matrix 132 that is emerging from the end 133 of the matrix introduction conduit 130. This can assist in nebulising the matrix as it emerges from the matrix introduction conduit 130.

The gap 131 may be less than, greater than or equal to about 0.01 mm, 0.02 mm, 0.03 mm, 0.04 mm, 0.05 mm, 0.06 mm, 0.07 mm, 0.08 mm, 0.09 mm, 0.1 mm, 0.5 mm, 1 mm, 2 mm, 3 mm, 4 mm or 5 mm.

The first conduit 102 and/or second conduit 103 and/or third conduit 104 may have an inner or internal diameter (e.g., inner diameter 121 of first conduit 102) of less than, greater than and/or equal to about 0.5 mm, 1 mm, 2 mm, 3 mm, 4 mm or 5 mm.

The matrix introduction conduit 130 and/or inlet tube 140 may have an inner or internal diameter of less than, greater than and/or equal to about 0.01 mm, 0.02 mm, 0.03 mm, 0.04 mm, 0.05 mm, 0.06 mm, 0.07 mm, 0.08 mm, 0.09 mm, 0.1 mm, 0.5 mm, 1 mm, 2 mm, 3 mm, 4 mm or 5 mm. The inner or internal diameter of the matrix introduction conduit 130 and/or inlet tube 140 may correspond to the diameter of the passage through which matrix or matrix molecules (including both the molecular constituents of the aerosol particles 122 and the matrix 132) pass in use.

The T-junction arrangement and apparatus shown in respect of FIGS. 4A and 4B can provide a particularly effective manner in which to intermix analyte aerosol particles directly with a matrix, that is without the further assistance of a gas such as a Venturi gas.

The matrix (e.g., isopropanol) can aid in cleaning the parts of the apparatus that come into contact with it. In this case that comprises the matrix introduction conduit 130, second conduit 103 and third conduit 104 of the T-junction 100 and inlet tube 140. For this reason, it may be desirable to have a further connecting portion located at the central junction 101 that connects the first conduit 102 to the central junction 101. The first conduit 102 and the sample transfer tube 120 may then be disposable and/or replaceable such that any part of the apparatus that does not come into contact with the matrix may be disposable and/or replaceable.

The sample transfer tube 120 may have an inlet for receiving aerosol sample 122 from a sample being investigated.

The T-junction 100 may be directly attached onto the inlet tube 140. The inlet tube or capillary 140 may form an inlet capillary for the ion analyser or mass spectrometer 110.

It will be apparent that the inlet arrangement according to the embodiment shown and described above with reference to FIGS. 4A and 4B may not require a gas such as nitrogen or standard medical air. Furthermore, the arrangement shown and described above with reference to FIGS. 4A and 4B can utilise the inherent vacuum of the ion analyser or mass spectrometer 110 in order to aspirate the aerosol or other gaseous sample containing the analyte. Such an arrangement can help to avoid diluting the analyte in the aerosol and has been found to lead to an increase in ion signal sensitivity.

The aerosol particles 122 may be introduced into the T-junction 100 via the sample transfer tube 120. A matrix compound 132 such as isopropanol may be introduced into the T-junction via the matrix introduction conduit 130. The aerosol particles 122 and matrix compound 132 may be drawn towards the inlet 112 of the ion analyser or mass spectrometer 110 by a pressure differential caused by the decreased pressure region 114 being at a lower pressure to that of the inlet to the sample transfer tube 120 and the matrix introduction conduit 130.

The matrix molecules 142 (in which both the molecular constituents of the aerosol particles 122 and the matrix 132 may be present) may be arranged to enter into the decreased pressure or decreased pressure region 114 whereupon the matrix molecules 142 can gain substantial linear velocity e.g., due to the adiabatic expansion of gas entering the decreased pressure region 114 from the sample transfer tube 120 and/or due to the associated free jet formation.

The accelerated matrix molecules 142 may be arranged to impact upon a collision surface 9 such that the impact event fragments the matrix molecules 142. This can lead to the formation of gas phase ions 149 comprising the molecular constituents of the aerosol sample 122 and may also lead to the formation of matrix molecules 148.

The collision surface 116 may be heated, for example by an inductive or resistive heater, and/or may be controlled and maintained at a temperature that is substantially higher than the ambient temperature.

The matrix molecules 148 may freely diffuse into the vacuum. In contrast, the gas phase ions 149 of the molecular constituents of the aerosol sample 122 may be transferred by ion optics 118 to an analysis region of the ion analyser or mass spectrometer 110. The analyte ions 149 may be guided to the analysis region by applying voltages to the ion optics 118. The analyte ions 149 may then be analysed by the ion analyser or mass spectrometer 110.

According to an embodiment the ion analyser or mass spectrometer 110 may comprise an ion mobility spectrometer. According to another embodiment the ion analyser or mass analyser 110 may comprise a mass spectrometer. According to a yet further embodiment the ion analyser or mass spectrometer 110 may comprise the combination of an ion mobility spectrometer and a mass spectrometer.

As a result of the analysis, chemical information about the sample 122 may be obtained.

Parts of the T-junction arrangement may be arranged so as to form part of a disposable inlet arrangement for a rapid evaporative ionisation mass spectrometry device. For example, the sample transfer tube 120 may be disposable and form part of a disposable rapid evaporative ionisation mass spectrometry device. In this manner, the portion of the apparatus exposed to only aerosol (and not both aerosol and matrix) may be disposable after each use. Disposing of this portion of the device may reduce contamination in subsequent experiments. To achieve this, the T-junction may comprise a connecting portion located at the point at which the sample transfer tube 120 meets the matrix introduction conduit 130.

According to another embodiment the entire T-junction 100 may form part of a disposable rapid evaporative ionisation mass spectrometry device. According to this embodiment the sample transfer tube 120, matrix introduction conduit 130 may be disposable and form part of a disposable rapid evaporative ionisation mass spectrometry device. A connector may be provided at the inlet 112 of the ion analyser or mass spectrometer 110. According to an embodiment the connector may be arranged at the inlet 112 to the first vacuum chamber 114. In this manner, the portion of the apparatus that does not form part of the vacuum region of the ion analyser or mass spectrometer 110 may be disposable after each use.

Inlet Setup #3—Matrix in Venturi Gas

FIG. 5A shows an apparatus for introducing an aerosol mixture into a ion analyser or mass spectrometer 180 with a Venturi pump 150. The ion analyser or mass spectrometer 180 may comprise an inlet or inlet portion 182 and a decreased pressure region 184 (e.g., a first vacuum region). A collision surface 186 (e.g., a solid collision surface) and optionally ion optics 188 may be arranged within the decreased pressure region 184. The ion optics 188 may comprise an ion guide, for example a Stepwave® ion guide.

The Venturi pump 150 may comprise an inlet tube 152 that may be connected to a device or probe (e.g., a rapid evaporative ionisation mass spectrometry device or probe as described herein) and may be configured to transport aerosol particles 160 from a sample (e.g., biologic tissue) to the Venturi pump 150.

The Venturi pump 150 may comprise a gas and matrix inlet 154 that may be arranged and adapted to introduce a gas (e.g., nitrogen or standard medical air) and a matrix or matrix compound 162 into the flow path of the aerosol particles 160 being transported into the Venturi pump 150 by the inlet tube 152. The Venturi pump 150 may facilitate the aspiration of aerosol particles 160 or other gaseous sample containing the analyte and may be driven by nitrogen or standard medical air.

The Venturi pump 150 may comprise a sample transfer portion or capillary 156 that may be arranged and adapted to transfer the sample and gas mixture from the tube 152 and direct this mixture past an inlet 158, which may form the entrance of a channel 159 to the ion analyser or mass spectrometer 180. An end 157 of the channel 159 may be located within and fluidly sealed against the inlet or inlet portion 182 of the ion analyser or mass spectrometer 180.

Aerosol particles 160 may be drawn into the channel 159 through the inlet 158 by the pressure difference between the ion analyser or mass spectrometer and the region adjacent the inlet 158 to the channel 159.

Some of (and sometimes a majority of) the matrix and larger aerosol particles 161 may travel past the entrance to the channel 159 and leave the apparatus via an exhaust 151. A filter, for example a high efficiency particulate air ("HEPA") filter may be arranged and adapted to filter gases and other matter passed through the exhaust 151.

The aerosol particles 160 and the matrix 162 may intermix within the sample transfer portion or capillary 156 and channel 159 and matrix molecules 164 may be formed, wherein both the molecular constituents of the aerosol particles 160 and the matrix 162 may be present within the matrix molecules 164.

In order to ensure adequate mixing of the sample, the matrix flow rate, or the flow rate of the Venturi gas and matrix, may be greater than 1 ml/min, 1.5 ml/min, 2 ml/min, 2.5 ml/min or 3 ml/min. This may be higher than the flow rate of the Venturi gas described in relation to the embodiment of FIGS. 2A-2C.

The matrix molecules 164 (in which both the molecular constituents of the aerosol particles 160 and the matrix 162 may be present) may be arranged to enter into the decreased pressure or decreased pressure region 184 whereupon the matrix molecules 164 can gain substantial linear velocity e.g., due to the adiabatic expansion of gas entering the decreased pressure region 184 from the sample transfer portion 156 and/or due to the associated free jet formation.

The accelerated matrix molecules 164 may be arranged to impact upon a collision surface 186 such that the impact event fragments the matrix molecules 164. This can lead to the formation of gas phase ions 190 comprising the molecular constituents of the aerosol sample 160 and may also lead to the formation of matrix molecules 189.

The collision surface 186 may be heated, for example by an inductive or resistive heater, and/or may be controlled and maintained at a temperature that is substantially higher than the ambient temperature.

The matrix molecules 189 may freely diffuse into the vacuum. In contrast, the gas phase ions 190 of the molecular constituents of the aerosol sample 160 may be transferred by ion optics 188 to an analysis region of the ion analyser or mass spectrometer 180. The analyte ions 190 may be guided to the analysis region by applying voltages to the ion optics 188. The analyte ions 190 may then be analysed by the ion analyser or mass spectrometer 180.

According to an embodiment the ion analyser or mass spectrometer 180 may comprise an ion mobility spectrometer. According to another embodiment the ion analyser or mass analyser 180 may comprise a mass spectrometer. According to a yet further embodiment the ion analyser or mass spectrometer 180 may comprise the combination of an ion mobility spectrometer and a mass spectrometer, for example a tandem mass spectrometer and ion mobility spectrometer.

As a result of the analysis, chemical information about the sample 160 may be obtained.

Inlet Setup #4—Matrix Separate to Venturi Gas

Figure 5B:
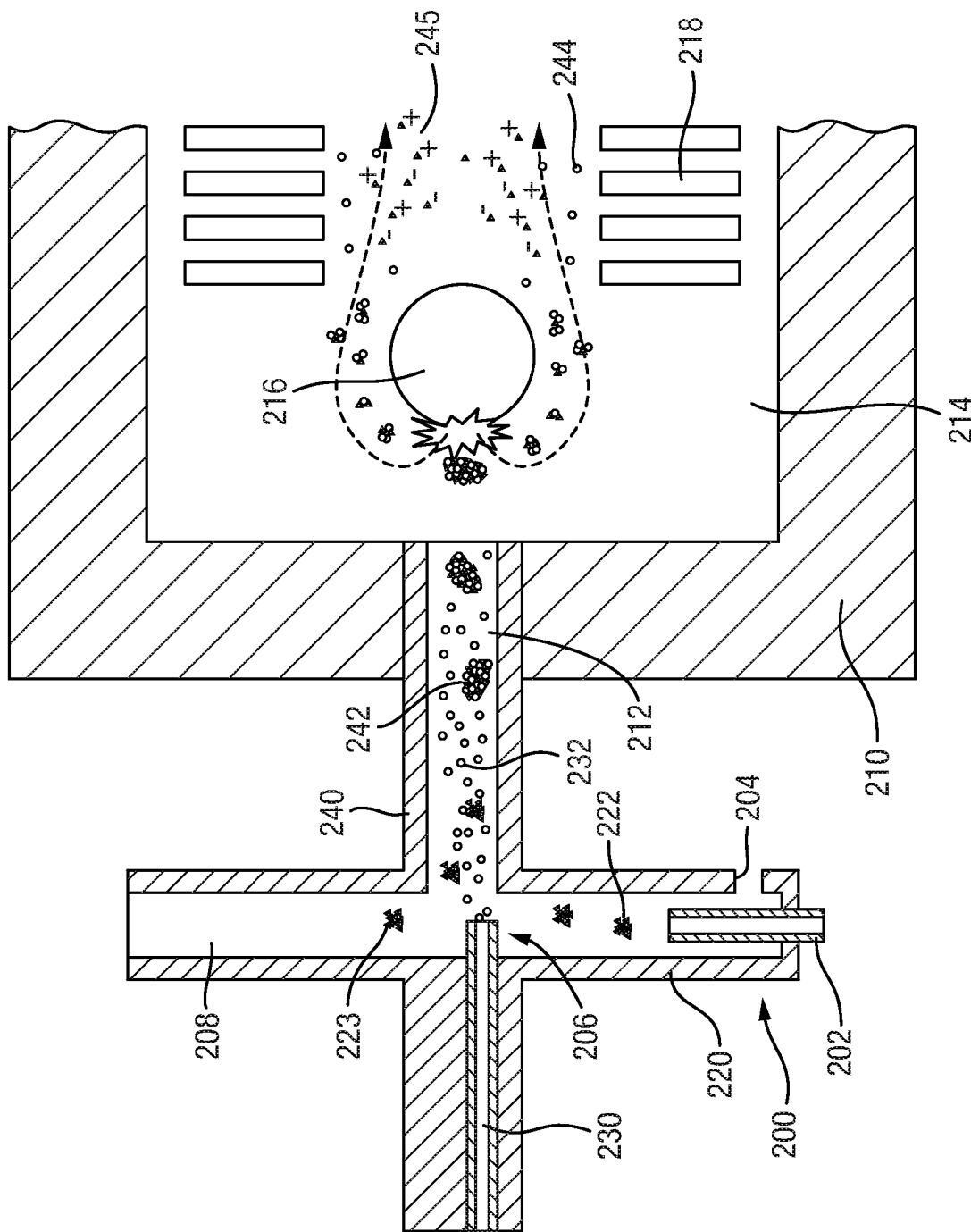

FIG. 5B shows an apparatus similar to FIG. 5A, except the matrix is introduced through a dedicated matrix introduction conduit (more similar to FIGS. 2A-2C) as described below.

The apparatus includes a Venturi pump 200 for introducing an aerosol mixture into an ion analyser or mass spectrometer 210. The ion analyser or mass spectrometer 210 may comprise an inlet or inlet portion 212 and a decreased pressure region 214 (e.g., a first vacuum region). A collision surface 216 (e.g., a solid collision surface) and optionally ion optics 218 may be arranged within the decreased pressure region 214. The ion optics 218 may comprise an ion guide, for example a Stepwave® ion guide.

The Venturi pump 200 may comprise an inlet tube 202 that may be connected to a device or probe (e.g., a rapid evaporative ionisation mass spectrometry device or probe as described herein) and may be configured to transport aerosol particles 222 from a sample (e.g., biologic tissue) to the Venturi pump 200.

The Venturi pump 200 may comprise a gas inlet 204 that may be arranged and adapted to introduce a gas (e.g., nitrogen or standard medical air) into the flow path of the aerosol particles 222 being transported into the Venturi pump 200 by the inlet tube 202.

The Venturi pump 200 may facilitate the aspiration of aerosol particles 222 or other gaseous sample containing the analyte and may be driven by nitrogen or standard medical air.

The Venturi pump 200 may comprise a sample transfer portion or capillary 220 that may be arranged and adapted to direct the sample and gas mixture produced by the Venturi pump 200 towards a junction 206. A matrix introduction conduit 230 is arranged and adapted to introduce matrix or a matrix compound 232 into the junction 206 and direct the flow of the matrix compound 232 towards an inlet tube 240.

The aerosol particles 222 and the matrix 232 may intermix at the junction 206 or as they travel through inlet tube 240. The smaller aerosol particles may have a momentum such that they may be carried by the airflow entering into the inlet tube of the ion analyser or mass spectrometer 210, due to the pressure differential between the region adjacent the Venturi pump 200 (which may be at substantially atmospheric or ambient pressure) and the decreased pressure region 214 of the mass spectrometer 210.

The larger aerosol particles 223 may have a relatively high momentum such that they are not carried by the airflow into the inlet tube 240, but travel past the junction 206 and leave the apparatus via an exhaust 208. A filter, for example a high efficiency particulate air ("HEPA") filter may be arranged and adapted to filter gases and other matter passed through the exhaust 208. Whilst shown as contiguous in FIG. 5B, the sample transfer portion 220 may be a separate component from the junction 206 and inlet tube 240. The junction 206 may comprise a connector or connecting portion (not shown) for connecting to a separate sample transfer portion 220. The connection between the junction 206 and the sample transfer portion 220 may be fluidly sealed, and/or may comprise a ring clamp.

An end 157 of the inlet tube 240 may be located within and fluidly sealed against the inlet or inlet portion 212 of the ion analyser or mass spectrometer 210.

The aerosol particles 222 and the matrix 232 may intermix within the inlet tube 240 and matrix molecules 242 may be formed, wherein both the molecular constituents of the aerosol particles 222 and the matrix 232 may be present within the matrix molecules 242.

The matrix molecules 242 (in which both the molecular constituents of the aerosol particles 222 and the matrix 232 may be present) may be arranged to enter into the decreased pressure or decreased pressure region 214 whereupon the matrix molecules 242 can gain substantial linear velocity e.g., due to the adiabatic expansion of gas entering the decreased pressure region 214 from the inlet tube 240 and/or due to the associated free jet formation.

The accelerated matrix molecules 242 may be arranged to impact upon the collision surface 216 such that the impact event fragments the matrix molecules 242. This can lead to the formation of gas phase ions 245 comprising the molecular constituents of the aerosol sample 222 and may also lead to the formation of matrix molecules 244.

The collision surface 216 may be heated, for example by an inductive or resistive heater, and/or may be controlled and maintained at a temperature that is substantially higher than the ambient temperature.

The matrix molecules 244 may freely diffuse into the vacuum. In contrast, the gas phase ions 245 of the molecular constituents of the aerosol sample 222 may be transferred by ion optics 218 to an analysis region of the ion analyser or mass spectrometer 210. The analyte ions 245 may be guided to the analysis region by applying voltages to the ion optics 218. The analyte ions 245 may then be analysed by the ion analyser or mass spectrometer 210.

According to an embodiment the ion analyser or mass spectrometer 210 may comprise an ion mobility spectrometer. According to another embodiment the ion analyser or mass analyser 210 may comprise a mass spectrometer. According to a yet further embodiment the ion analyser or mass spectrometer 210 may comprise the combination of an ion mobility spectrometer and a mass spectrometer.

As a result of the analysis, chemical information about the sample 222 may be obtained.

In any of the inlet setups disclosed above, the diameter of the matrix introduction conduit 30, 130, 230 may be greater than, less than or substantially equal to 0.2 mm, 0.4 mm, 0.6 mm, 0.8 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm or 5 mm.

The matrix may include polar molecules, water, one or more alcohols, methanol, ethanol, isopropanol, acetone or acetonitrile. Isopropanol has been found to be particularly advantageous. The matrix may comprise a lockmass or calibration compound.

Analysis Using Isopropanol as a Matrix

Isopropyl alcohol was used to aid ionisation when operating an ion analyser or mass spectrometer with the inlet setups disclosed above. As discussed, ionisation is aided due to the isopropyl alcohol partially or fully solvating analyte molecules and thus reducing intermolecular forces which would otherwise negatively affect ionisation and thus reduce sensitivity.

The introduction of isopropyl alcohol was first tested using inlet setup #1 for aerosol transfer to the inlet capillary of the ion analyser or mass spectrometer 7. In comparison to a skimmer-type atmospheric pressure ionisation ("API") ion source, or collision on a cold surface, a heated collision surface according to various embodiments was found to eliminate certain spectral features such as ceramides in *Bacteroides fragilis* experimental data as shown in FIGS. 6A-C.

Figure 6A:
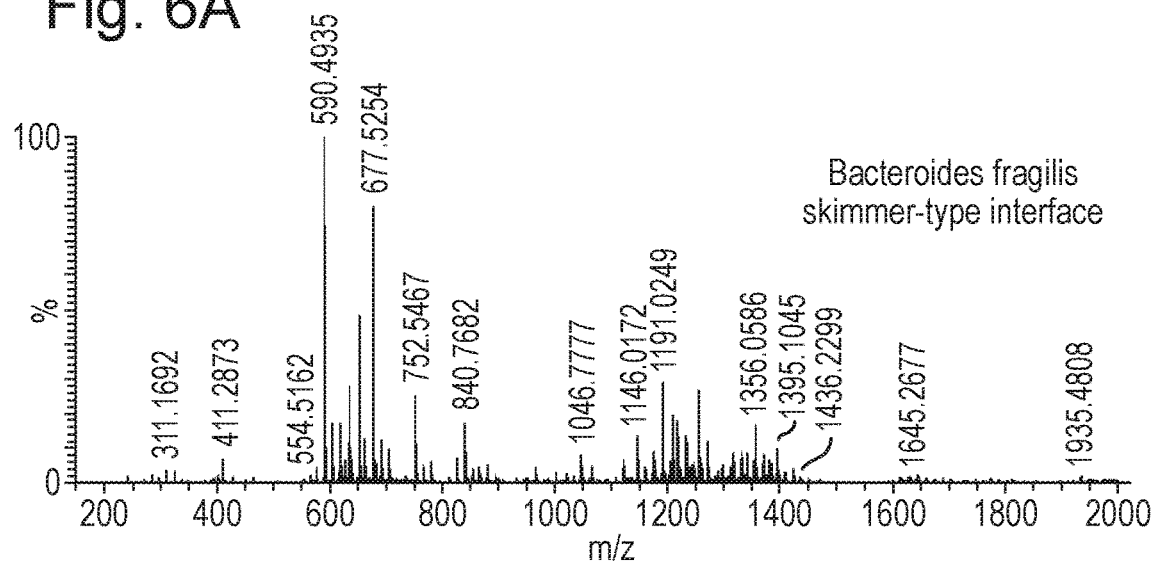
FIG. 6A shows a mass spectrum produced using a skimmer-type atmospheric pressure inlet ("API")
Figure 6B:
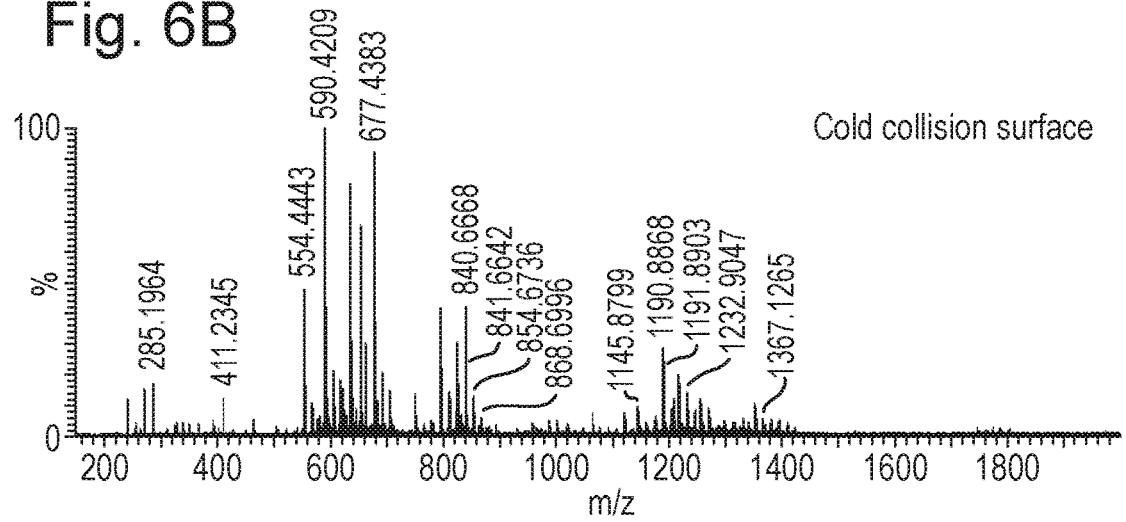
FIG. 6B shows a mass spectrum produced from *Bacteroides fragilis* using a cold collision sphere and FIG. 6C shows a mass spectrum produced from *Bacteroides fragilis* using a heated collision sphere.

FIG. 6A shows a mass spectrum produced from *Bacteroides fragilis* using a skimmer-type atmospheric pressure inlet ("API") involving collision upon a cold surface. FIG. 6B shows a mass spectrum produced from *Bacteroides fragilis* using a cold collision sphere 9 according to the embodiments shown in FIGS. 3 and 4.

Figure 6C:
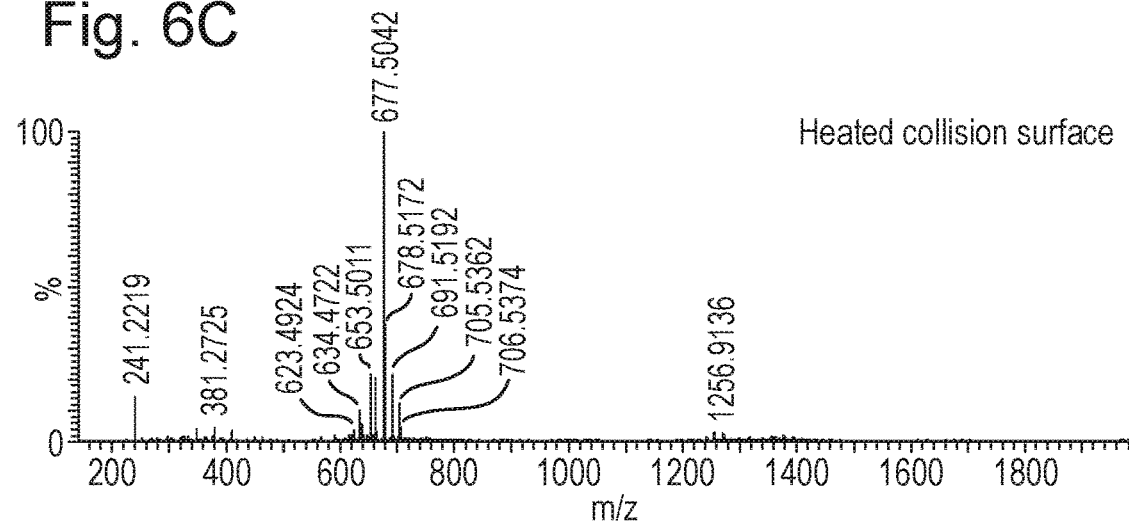

FIG. 6C shows a mass spectrum produced from *Bacteroides fragilis* using a heated collision sphere according to the embodiments shown in FIGS. 3 and 4.

Introduction of isopropanol into the sampled aerosol before introduction into the ion analyser or mass spectrometer 7 was found to restore those spectral features and generate a mass spectral fingerprint similar to that of an atmospheric pressure interface with a non-heated collision surface.

Figure 7A:
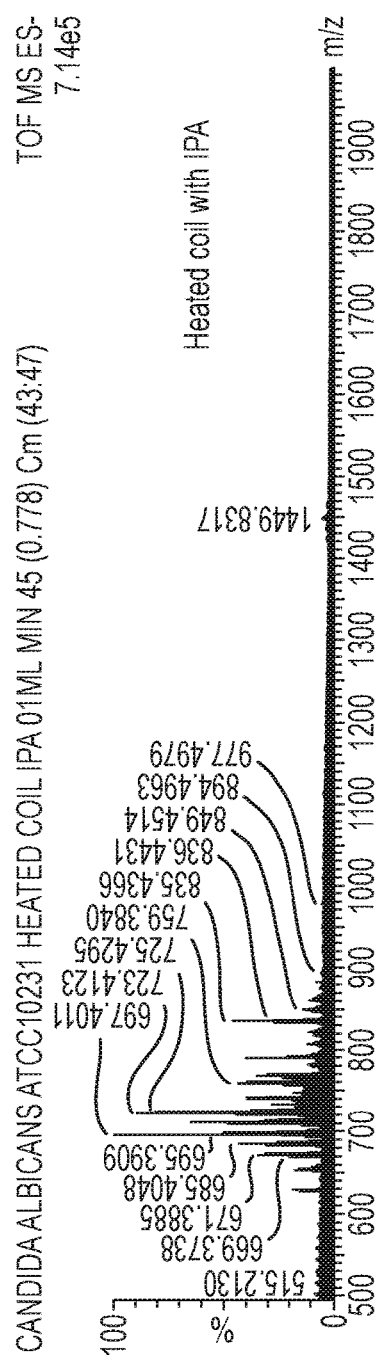
FIG. 7A shows a mass spectrum produced from *Candida albicans* using a heated coil interface with introduction of isopropanol as a matrix.
Figure 7B:
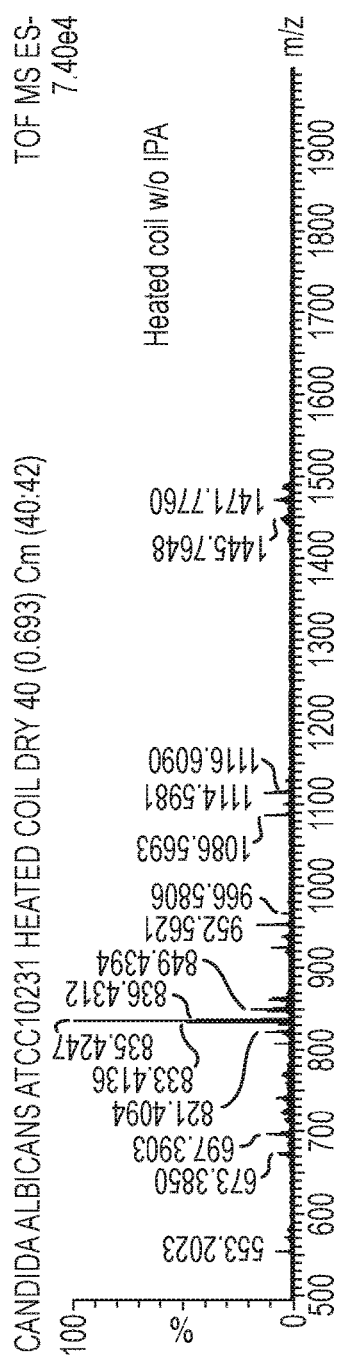
FIG. 7B shows a mass spectrum produced from *Candida albicans* using a heated coil interface without introduction of isopropanol and FIG. 7C shows a mass spectrum produced from *Candida albicans* using a cold sphere collision surface.
Figure 7C:
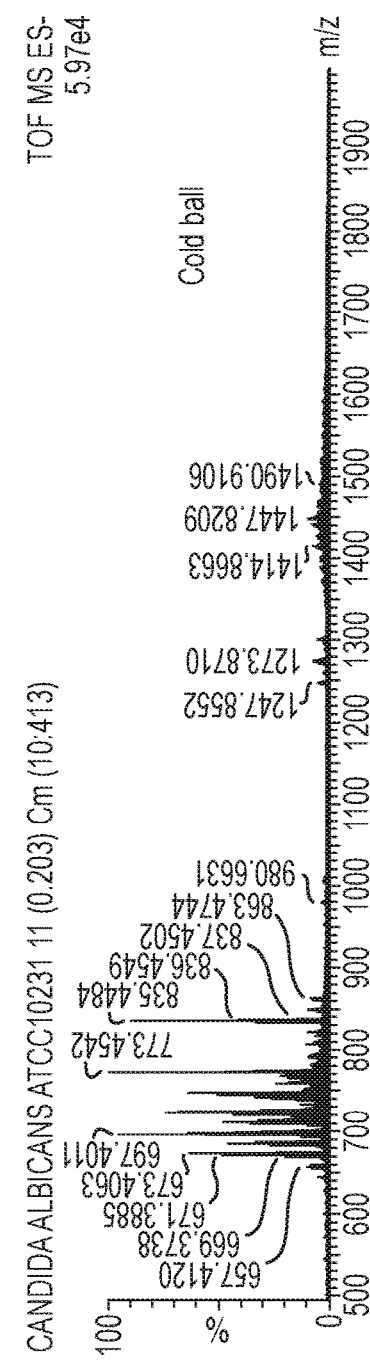
Figure 8A:
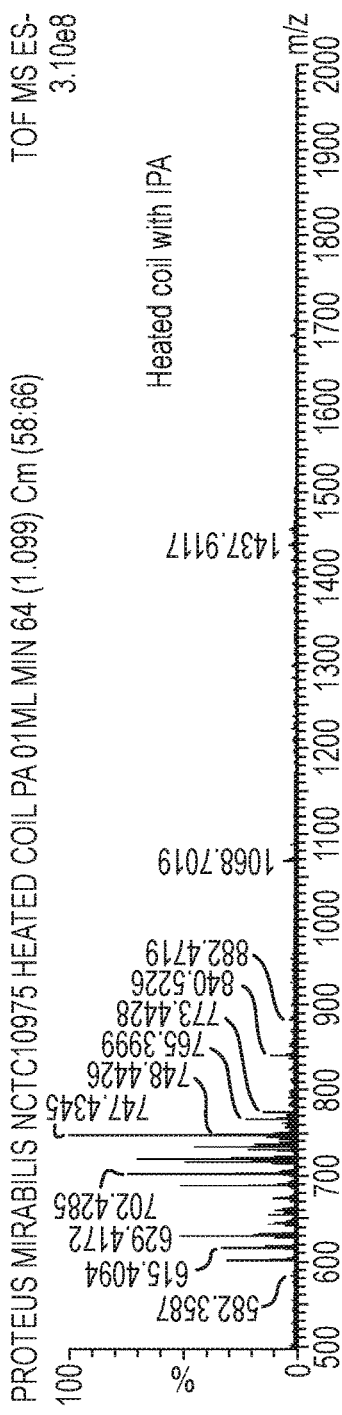
FIG. 8A shows a mass spectrum produced from *Proteus mirabilis* using a heated coil interface with introduction of isopropanol as a matrix.
Figure 8B:
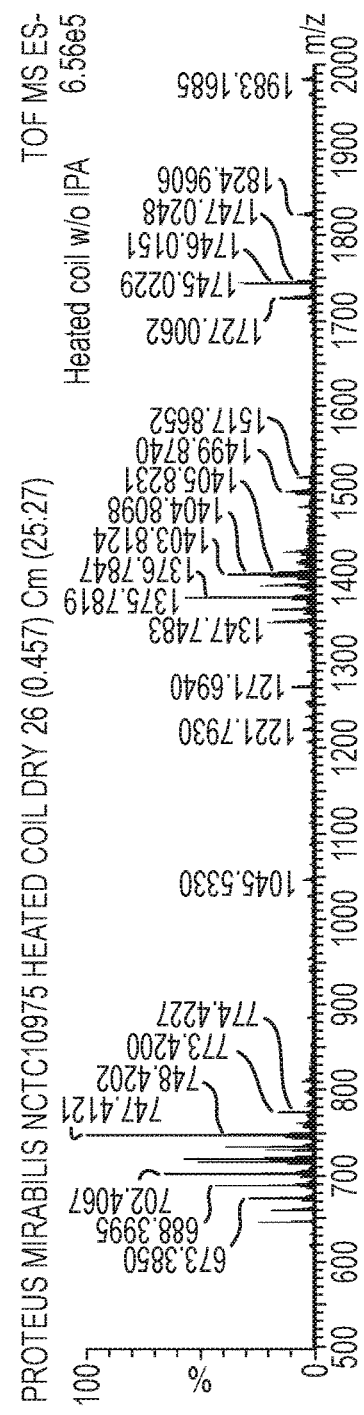
FIG. 8B shows a mass spectrum produced from *Proteus mirabilis* using a heated coil interface without introduction of isopropanol and FIG. 8C shows a mass spectrum produced from *Proteus mirabilis* using a cold sphere collision surface.
Figure 8C:
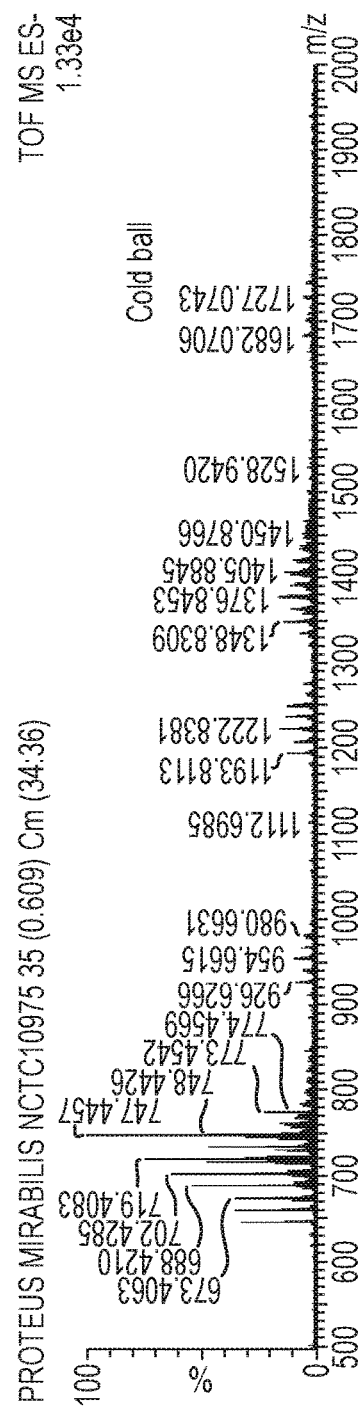

The effect on spectral appearance was also demonstrated for *Candida albicans* as shown in FIGS. 7A-7C and for *Proteus mirabilis* as shown in FIGS. 8A-8C.

As will be discussed in more detail below, it is apparent from the experimental results shown in FIGS. 7A-7C and FIGS. 8A-8C that using a heated impact surface (as opposed to a cold impact surface) results in significant beneficial changes to the spectral appearance.

FIGS. 7A and 8A show mass spectra produced from *Candida albicans* and *Proteus mirabilis* respectively using a heated coil interface with introduction of isopropanol.

FIGS. 7B and 8B show mass spectra produced from *Candida albicans* and *Proteus mirabilis* respectively using a heated coil interface but without introduction of isopropanol.

FIGS. 7C and 8C show mass spectra produced from *Candida albicans* and *Proteus mirabilis* respectively using a cold solid spherical collision surface 9 according to the embodiments described above with reference to FIGS. 4 and 5.

As can be seen from FIGS. 7A-C, many spectral features in *Candida albicans* are significantly reduced in relative intensity or disappear altogether. Introduction of isopropanol alcohol as a matrix helps to circumvent this problem and creates a spectrum more similar to cold collision surface interfaces. However, one observed disadvantage is the observation of a rising baseline towards lower masses effectively reducing signal-to-noise ratio.

The use of isopropanol was observed to result in a loss of mass spectral information above m/z 1000 as is apparent in case of *Proteus mirabilis* (FIGS. 8A-C).

An increase in sensitivity may be achieved by combining the introduction of isopropanol with the direct introduction of aerosol sample (containing the analyte) into the ion analyser or mass spectrometer. For this purpose, an inlet setup similar to inlet setup #2 was tested. The inlet setup included a T-junction as shown in FIGS. 4A and 4B.

A device in the form of a T-piece was provided to connect a sample transfer tube 21 and a matrix introduction conduit 3 with an extended mass spectrometer inlet capillary. Increasing isopropanol flow rates were tested between 0-0.25 mL/min and the optimum flow rate was determined to be 0.1 mL/min.

Figure 10A:
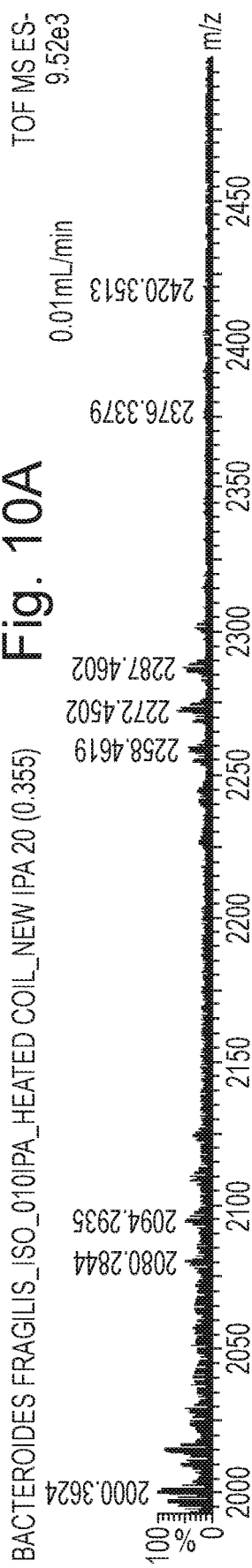
FIG. 10A shows a mass spectrum produced from *Bacteroides fragilis* at an isopropanol flow rate of 0.01 mL/min.

The effect on spectral appearance for different isopropanol flow rates was determined for *Bacteroides fragilis* and is shown in FIGS. 9A-1 and FIGS. 10A-1.

FIG. 9A shows a mass spectrum produced from *Bacteroides fragilis* at an isopropanol flow rate of 0.1 mL/min, FIG. 9B shows a mass spectrum produced from *Bacteroides fragilis* at an isopropanol flow rate of 0.02 mL/min, FIG. 9C shows a mass spectrum produced from *Bacteroides fragilis* at an isopropanol flow rate of 0.05 mL/min, FIG. 9D shows a mass spectrum produced from *Bacteroides fragilis* at an isopropanol flow rate of 0.0.07 mL/min, FIG. 9E shows a mass spectrum produced from *Bacteroides fragilis* at an isopropanol flow rate of 0.1 mL/min, FIG. 9F shows a mass spectrum produced from *Bacteroides fragilis* at an isopropanol flow rate of 0.13 mL/min, FIG. 9G shows a mass spectrum produced from *Bacteroides fragilis* at an isopropanol flow rate of 0.15 mL/min, FIG. 9H shows a mass spectrum produced from *Bacteroides fragilis* at an isopropanol flow rate of 0.2 mL/min, and FIG. 9I shows a mass spectrum produced from *Bacteroides fragilis* at an isopropanol flow rate of 0.25 mL/min.

Figure 10B:
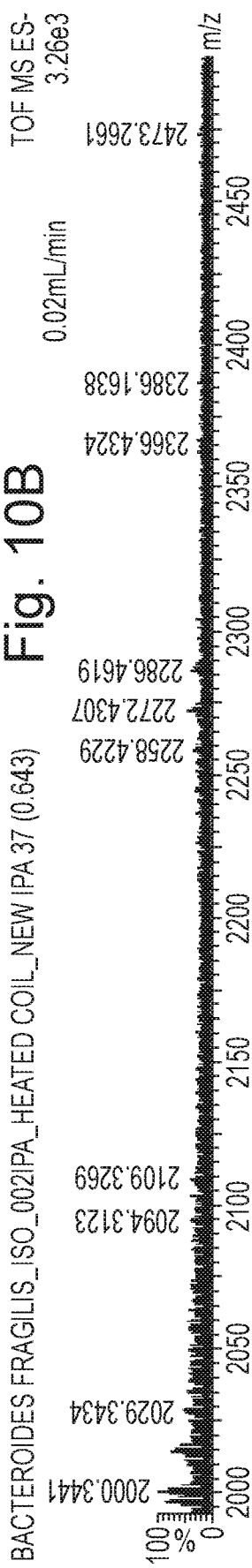
FIG. 10B shows a mass spectrum produced from *Bacteroides fragilis* at an isopropanol flow rate of 0.02 mL/min.
Figure 10C:
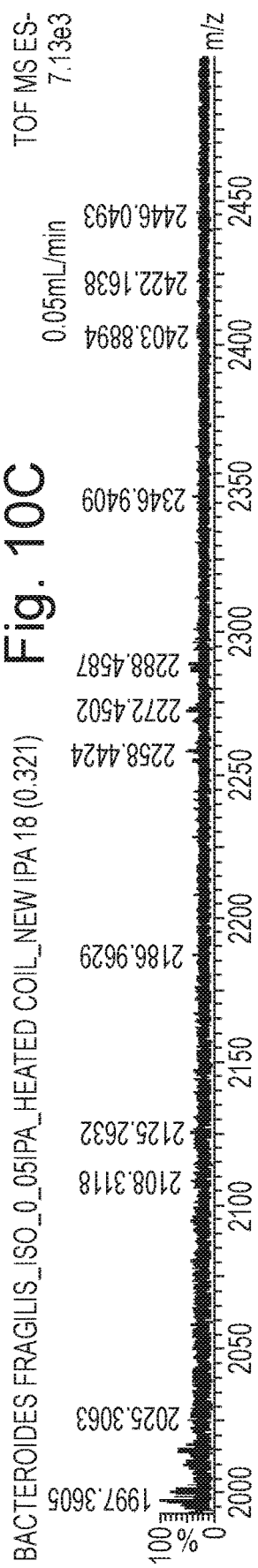
FIG. 10C shows a mass spectrum produced from *Bacteroides fragilis* at an isopropanol flow rate of 0.05 mL/min.
Figure 10D:
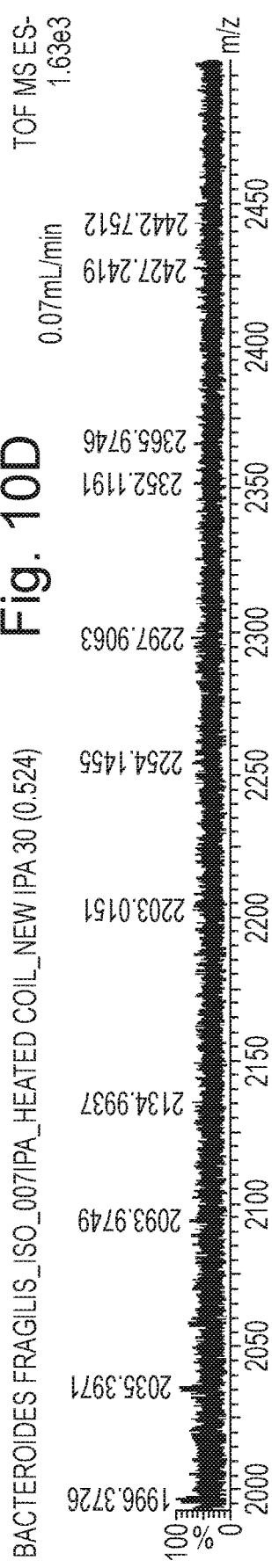
FIG. 10D shows a mass spectrum produced from *Bacteroides fragilis* at an isopropanol flow rate of 0.0.07 mL/min.
Figure 10E:
FIG. 10E shows a mass spectrum produced from *Bacteroides fragilis* at an isopropanol flow rate of 0.1 mL/min.
Figure 10F:
FIG. 10F shows a mass spectrum produced from *Bacteroides fragilis* at an isopropanol flow rate of 0.13 mL/min.
Figure 10G:
FIG. 10G shows a mass spectrum produced from *Bacteroides fragilis* at an isopropanol flow rate of 0.15 mL/min.
Figure 10H:
FIG. 10H shows a mass spectrum produced from *Bacteroides fragilis* at an isopropanol flow rate of 0.2 mL/min.
Figure 10I:
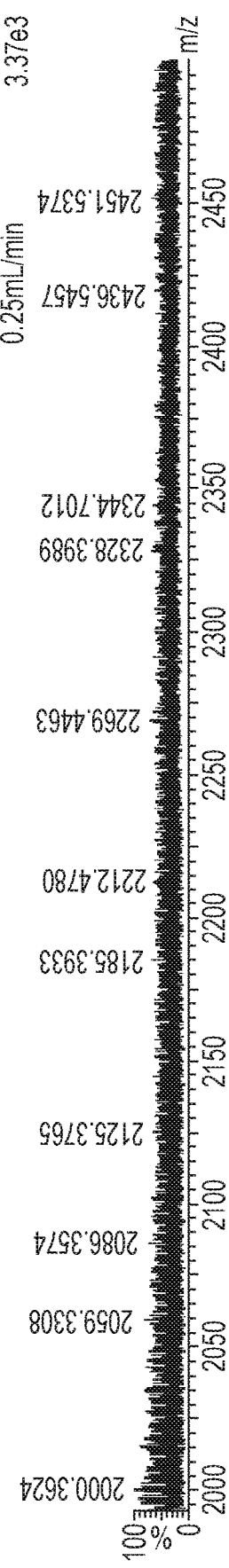
FIG. 10I shows a mass spectrum produced from *Bacteroides fragilis* at an isopropanol flow rate of 0.25 mL/min.

FIG. 10A shows a mass spectrum produced from *Bacteroides fragilis* at an isopropanol flow rate of 0.1 mL/min, FIG. 10B shows a mass spectrum produced from *Bacteroides fragilis* at an isopropanol flow rate of 0.02 mL/min, FIG. 10C shows a mass spectrum produced from *Bacteroides fragilis* at an isopropanol flow rate of 0.05 mL/min, FIG. 10D shows a mass spectrum produced from *Bacteroides fragilis* at an isopropanol flow rate of 0.0.07 mL/min, FIG. 10E shows a mass spectrum produced from *Bacteroides fragilis* at an isopropanol flow rate of 0.1 mL/min, FIG. 10F shows a mass spectrum produced from *Bacteroides fragilis* at an isopropanol flow rate of 0.13 mL/min, FIG. 10G shows a mass spectrum produced from *Bacteroides fragilis* at an isopropanol flow rate of 0.15 mL/min, FIG. 10H shows a mass spectrum produced from *Bacteroides fragilis* at an isopropanol flow rate of 0.2 mL/min, and FIG. 10I shows a mass spectrum produced from *Bacteroides fragilis* at an isopropanol flow rate of 0.25 mL/min.

The effect of the isopropanol being present is detectable from 0.02 mL/min upwards as clearly visible based on the appearance of m/z 590 (ceramide species) and m/z 752 ($\alpha$-Galactosylceramide). These species were found to increase in their relative abundance with further increasing isopropanol flow rates. As soon as the appearance of m/z 590 and 752 sets in, peaks in the very high mass region m/z>2000 were found to disappear (see FIG. 9) and this indicates a negative influence on heavier spectral features.

DESI Sprayer with Heated Transfer Capillary

FIG. 11 shows another embodiment and comprises a Desorption Electrospray Ionisation ("DESI") sprayer 300 in which a solvent capillary 302 may be arranged to direct electrically charged particles 304 of solvent at a sample surface 310. A sample 311 may be located on the sample surface 310, which may comprise analyte particles. The charging of the solvent particles may be achieved through the use of a power supply, for example a high-voltage power supply 306 that contacts the capillary 302. The high-voltage power supply 306 may comprise an electrode 307 which may contact any portion of the capillary 302 so that it is operable to charge the solvent particles as they leave an outlet end 303 of the capillary 302. The outlet end 303 of the capillary may be directed towards the sample surface 310.

A sheath gas 308 (e.g., nitrogen) may be arranged to surround the capillary 302 so as to atomise the solvent as it emerges from the capillary 302 and direct the electrically charged solvent particles 304 towards the surface 310. The sheath gas may be introduced through a tube 312 that may be coaxial to the solvent capillary 302, having an inlet 314 at an end distal to the sample surface 310 and an outlet 316 at an end facing the sample surface 310.

The outlet 316 of the sheath gas tube 312 may be concentric to the outlet end 303 of the capillary, which can facilitate in atomising the solvent as it emerges from the capillary 302. The solvent emerging from the outlet end 303 of the solvent capillary 302 may be atomised by the sheath gas 308. A connector 318 may connect the tube 312 to a source of gas suitable to use as a sheath gas. The sheath gas 308 may comprise nitrogen or standard medical air, and the source of sheath gas may be a source of nitrogen gas or standard medical air.

As the solvent droplets 304 contact the sample, analyte particles on the sample can desorb and the charged droplets and analyte mixture 320 may be transferred into a transfer capillary 330 that may lead to a mass analyser and/or ion mobility analyser and/or mass spectrometer 340. The charged droplet and analyte mixture may be transferred through an inlet 332 of the transfer capillary 330. This may be achieved by placing the opposite end 333 of the transfer capillary 330 in a low pressure region 352, for example a vacuum stage of the ion analyser or mass spectrometer 340.

The charged droplet and analyte mixture (including e.g., analyte ions) may be transferred by ion optics 352 to an analysis region of the ion analyser or mass spectrometer 340. The ion optics 352 may comprise an ion guide, for example a Stepwave® ion guide.

The analyte ions may be guided to the analysis region by applying voltages to the ion optics 352. The analyte ions may then be analysed by the mass analyser and/or ion mobility analyser or mass spectrometer 340.

According to an embodiment the ion analyser or mass spectrometer 340 may comprise an ion mobility spectrometer. According to a yet further embodiment the ion analyser or mass spectrometer 340 may comprise the combination of an ion mobility spectrometer and a mass spectrometer.

As a result of the analysis, chemical information about the sample 311 may be obtained.

One or more heaters may be provided to heat the various parts of the apparatus shown in FIG. 11. For example, a heater may be provided to heat one or more of the solvent capillary 302, the sheath gas tube 312, the sample surface 310 and the transfer or inlet capillary 330.

The one or more heaters may comprise a wire heater (e.g., a tungsten wrap) and/or may be configured to heat the respective part to above ambient temperature, and/or to a temperature of at least 30° C., 50° C., 100° C., 200° C., 300° C., 400° C., 500° C. or greater than 500° C. However, any type of heater may be used that has the function of heating the respective part, for example a blower or an inductive or resistive heater.

FIG. 11 shows a first heater 342 that may be arranged and adapted to heat the transfer or inlet capillary 330, such that the solvent and analyte mixture 320 may be heated before being passed onward, for example to the mass analyser and/or ion mobility analyser or mass spectrometer 340.

The first heater 348 may be located anywhere along the solvent capillary 330, for example adjacent to or at the inlet 341 of the mass analyser and/or ion mobility analyser or mass spectrometer. Alternatively, the first heater 342 may be located adjacent to or at the inlet 332 of the solvent capillary 330. The first heater 342 may comprise a wire heater (e.g., a tungsten wrap) and/or may be configured to heat the inlet capillary to above ambient temperature, and/or to a temperature of at least 30° C., 50° C., 100° C., 200° C., 300° C., 400° C., 500° C. or greater than 500° C.

A second heater 344 may be arranged and adapted to heat the sheath gas tube 312, such that the solvent and/or sheath gas may be heated.

The second heater 344 may be located at the end of the tube 312 nearest the sample surface 310, such that the solvent and/or sheath gas may be heated before being directed at the sample surface 310. The second heater 344 may comprise a wire heater (e.g., a tungsten wrap) and/or may be configured to heat the tube 312 and/or the solvent and/or the sheath gas to above ambient temperature, and/or to a temperature of at least 30° C., 50° C., 100° C., 200° C., 300° C., 400° C., 500° C. or greater than 500° C. A third heater 346 may be arranged and adapted to heat the solvent capillary 302, such that the solvent may be heated.

The third heater 346 may be located anywhere along the solvent capillary 302, for example nearest the end 305 located away from the sample surface 310, such that the solvent may be heated before it is surrounded by the sheath gas tube 312. The third heater 346 may comprise a wire heater (e.g., a tungsten wrap) and/or may be configured to heat the solvent capillary 302 and/or the solvent to above ambient temperature, and/or to a temperature of at least 30° C., 50° C., 100° C., 200° C., 300° C., 400° C., 500° C. or greater than 500° C. A fourth heater 348 may be arranged and adapted to heat the sample surface 310, such that the sample 311 and/or the sample surface 310 may be heated. The fourth heater 348 may be located beneath a portion of the sample surface 310 arranged and adapted to hold or contain the sample 311. The fourth heater 348 may comprise a wire heater (e.g., a tungsten wrap) and/or may be configured to heat the sample 311 and/or sample surface 310 and/or the solvent to above ambient temperature, and/or to a temperature of at least 30° C., 50° C., 100° C., 200° C., 300° C., 400° C., 500° C. or greater than 500° C. The impact of heating an ion inlet transfer capillary (such as a transfer capillary 120 as shown in FIG. 11) was tested on a Xevo G2-XS® quadrupole Time of Flight mass spectrometer and a Synapt G2-Si® quadrupole-ion mobility-Time of Flight mass spectrometer.

The ion transfer capillary was heated using a nickel wire heater in a range from 100 to 490° C. Pork liver sections were used and the intensities for selected fatty acids and phospholipids were compared. Inlet capillary heating was found to have some impact on fatty acid intensities using a Xevo® mass spectrometer and no impact using a Synapt® mass spectrometer. Intensities for the monitored phospholipids, however, could be improved by almost two orders of magnitude.

Figure 12A:
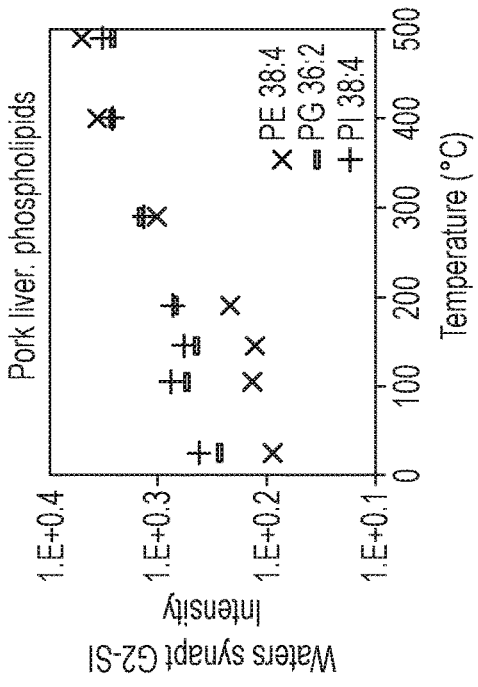
FIG. 12A shows a graph of intensity versus inlet capillary temperature for analysis of fatty acids using a Waters Synapt® mass spectrometer.
Figure 12C:
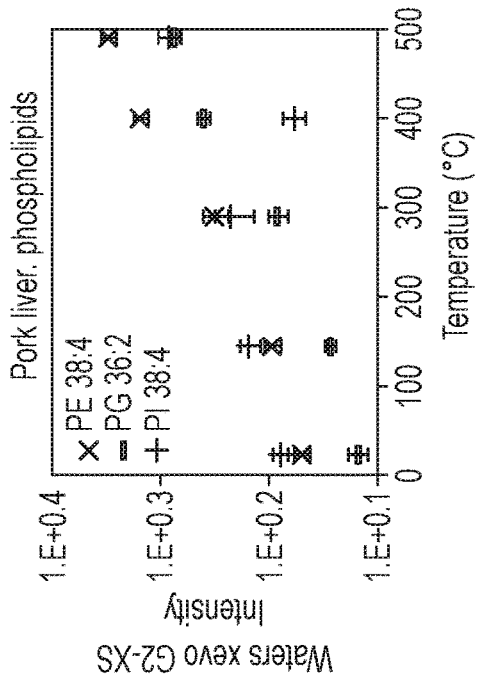
FIG. 12C shows a graph of intensity versus inlet capillary temperature for analysis of phospholipids using a Waters Synapt® mass spectrometer and FIG. 12D shows a graph of intensity versus inlet capillary temperature for analysis of phospholipids using a Waters Xevo® mass spectrometer.
Figure 12B:
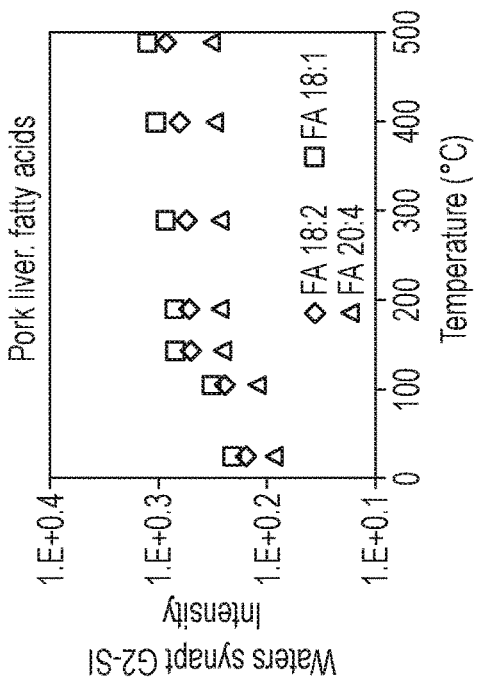
FIG. 12B shows a graph of intensity versus inlet capillary temperature for analysis of fatty acids using a Waters Xevo® mass spectrometer.
Figure 12D:
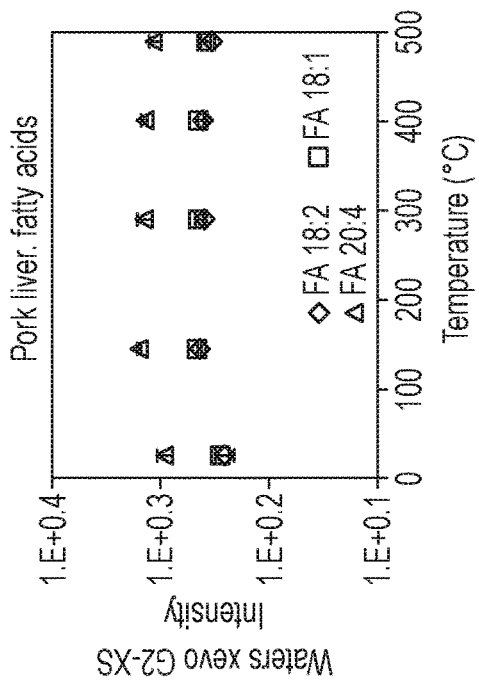

FIGS. 12A-D show the impact of inlet capillary heating on absolute intensity. FIGS. 12A and 12C relate to a Waters Synapt G2-Si® mass spectrometer and FIGS. 12B and 12D relate to a Waters Xevo G2-XS® mass spectrometer. Average intensities for selected fatty acids (FA), phosphatidyl ethanolamines (PE) and the most abundant phosphatidylinositol (PI) from pork liver sections are shown.

It is apparent from FIGS. 12A-D that increasing the temperature of the ion transfer capillary can increase the observed intensity of phospholipids by nearly two orders of magnitude.

The embodiments described in relation to FIG. 11 may be used in applications such as medical swabs, where the sample surface 310 forms the surface of a swab. In such a case, the swab itself may be heated so as to heat the sample 311 that is located on the swab. For example, the fourth heater may be a wire heater that is located within the swab, and may be arranged and adapted to heat the end of the swab configured to hold and/or retain biologic samples for analysis.

Systems for Use in an Operating Theatre

Figure 13B:
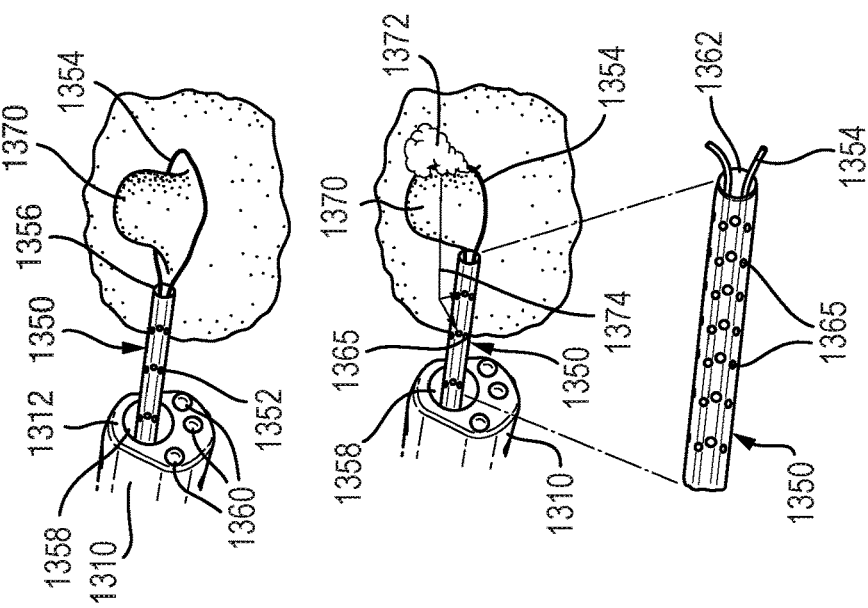
FIG. 13B shows an embodiment of a device that may be used in the apparatus of FIG. 13A
Figure 13A:
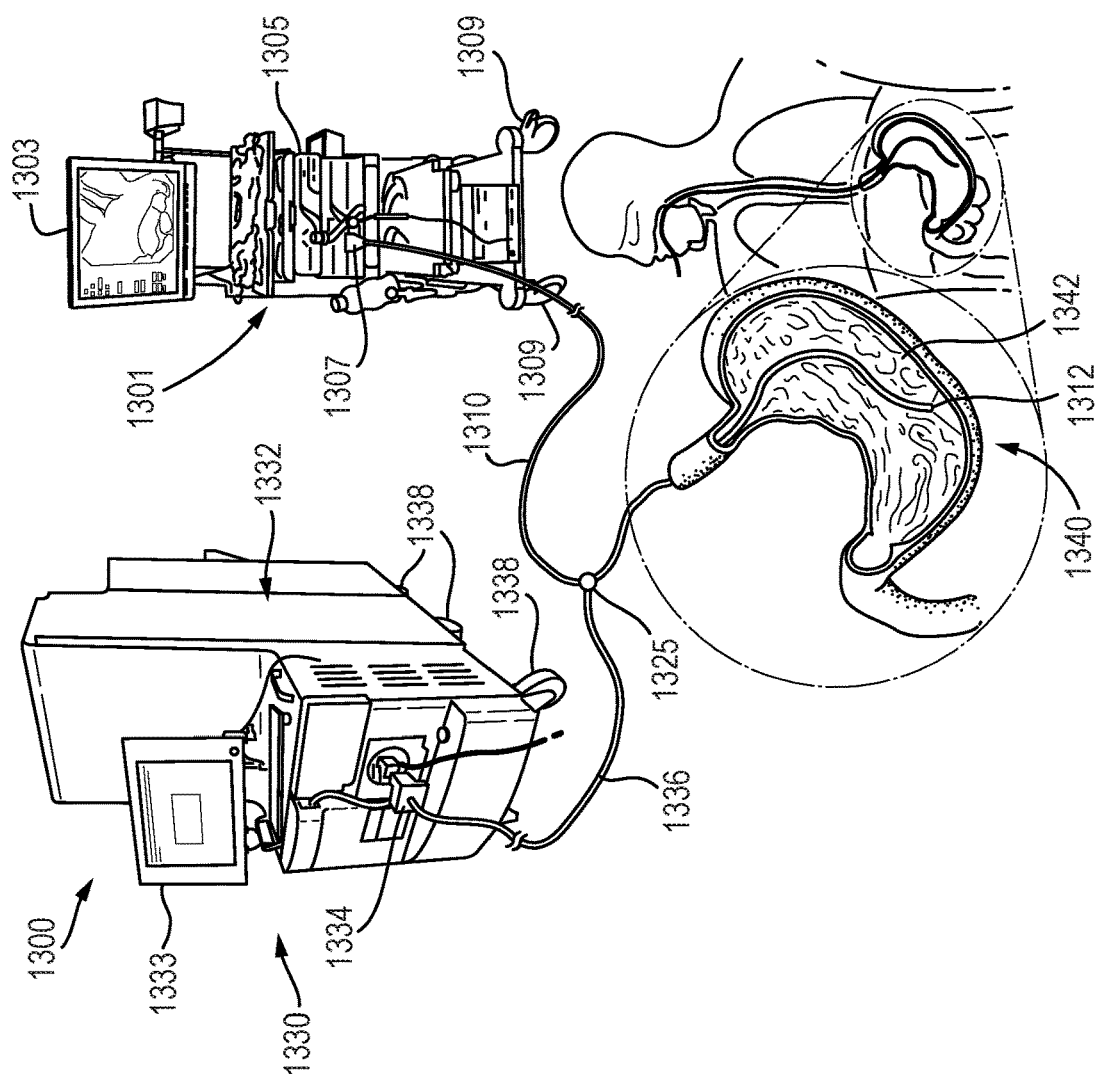
FIG. 13A shows an apparatus for performing surgery.

FIG. 13A shows an apparatus 1300, for example a portable apparatus 1300, that may be provided in accordance with an embodiment.

The apparatus 1300 may comprise a surgical stack 1301 comprising a camera monitor 1303 that is operatively connected to an instrument stack 1305. The instrument stack 1305 may comprise a camera unit 1307 that is operatively connected to an endoscope 1310. The surgical stack 1301 may comprise one or more surgical instruments, for example the endoscope 1310. Embodiments are envisaged wherein the camera monitor 1303 is or forms part of a mobile device, for example a mobile tablet device.

In various embodiments, the endoscope 1310 may be referred to as a laparoscope and comprise the same features and be arranged and adapted in the same manner as described in respect of the endoscope 1310.

The endoscope 1310 may comprise a tubing that houses one or more endoscopic devices, such as one or more optical fibers and/or data cables. The endoscope 1310 may comprise a bundle of optical fibers and/or data cables. The endoscope may take the form of an electrosurgical tool as described in any of the embodiments disclosed herein, for example the endoscope may be a laparoscope as described herein, or comprise a rapid evaporative ionization mass spectrometry device or probe as described below in relation to FIGS. 14A-B.

One of the optical fibers may feed light from a light source in the camera unit 1307 to a distal end 1312 of the endoscope 1310. One of the optical fibers may be arranged and adapted to feed light from the distal end 1312 to a camera or charge-coupled device ("CCD") located in the camera unit 1307. Alternatively, a camera or charge-coupled device ("CCD") may be located at the distal end 1312 of the endoscope 1310 and this may be operatively connected to the camera unit 1307 via one or more data cables.

The instrument stack 1305 may be portable. For example, the instrument stack 1305 may be located on wheels 1309 and/or be located on a track, such that the instrument stack may be moved between different locations, for example different operating theatres. The instrument stack 1301 may weigh less than 500 kg, 400 kg, 300 kg, 200 kg, 150 kg, 100 kg, 50 kg, 40 kg, 30 kg, 20 kg, 10 kg or 5 kg.

The portable apparatus 1300 may comprise an analytical stack 1330. The analytical stack 1330 may comprise one or more ion analysers or mass spectrometers 1332. The ion analyser or mass spectrometer 1332 may comprise an ion inlet device 1334 for introducing ions into the ion analyser for analysis, for example mass analysis and/or ion mobility analysis.

The ion inlet device 1334 may comprise any of the inlet setups #1 to #4 and discussed above in relation to FIGS. 2A-5B. For example, the tissue sampling device 1336 may correspond to (i) the tube 21 referenced in inlet setup #1 and shown in FIGS. 2A and 3, (ii) the sample transfer tube 120 reference in inlet setup #2 and shown in FIGS. 4A and 4B, (iii) the inlet tube 152 referenced in inlet setup #3 and shown in FIG. 5A, and (iv) the inlet tube 202 referenced in inlet setup #4 and shown in FIG. 5B.

The analytical stack 1330 may be portable. For example, the analytical stack 1330 may be located on wheels 1338 and/or be located on a track, such that the instrument stack may be moved between different locations, for example different operating theatres.

The analytical stack 1336 may weigh less than 500 kg, 400 kg, 300 kg, 200 kg, 150 kg, 100 kg, 50 kg, 40 kg, 30 kg, 20 kg, 10 kg or 5 kg.

A tissue sampling device 1336 may be connected to or form part of the endoscope 1310. The tissue sampling device 1336 may join the endoscope 1310 at a junction 1325. At the junction 1325, the endoscope 1310 and the tissue sampling device 1336 may separate, with the endoscope 1310 continuing on to the surgical stack 1301 and the tissue sampling device 1336 continuing on to the analytical stack 1330.

At the junction 1325 the endoscope 1310 and tissue sampling device 1336 may join and may be located within a larger tube. This can aid in inserting the endoscope 1310 and tissue sampling device 1336 into a human or animal body. The distal end 1312 of the endoscope 1310 may also correspond to or form the distal end 1312 of the tissue sampling device 1336.

The tissue sampling device 1336 may comprise one or more tubes and/or cables that may house one or more devices or tools, such as one or more electrodes and/or gas conduits. The tissue sampling device 1336 may comprise a tool, for example an electrosurgical tool such as a rapid evaporative ionization mass spectrometry device or probe, wherein the electrosurgical tool may comprise one or more electrodes, and the analytical stack 1330 may comprise a voltage supply arranged and adapted to apply a voltage to the one or more electrodes.

The tool (and, where included, the electrosurgical tool, rapid evaporative ionization mass spectrometry device or probe, and/or one or more electrodes) may be located at the distal end 1312 of the tissue sampling device 1336. The tool and/or one or more electrodes may be arranged and adapted to protrude from the distal end 1312 of the tissue sampling device 1336 and may be arranged and adapted to contact biologic tissue within the field of view of the camera or charge-coupled device ("CCD") discussed above.

The electrosurgical tool may be a monopolar device, in which case a counter electrode may be provided and may be arranged and adapted to contact a different portion of the biologic tissue that the one or more electrodes located at the distal end 1312 of the tissue sampling device 1336. For example, the counter electrode may comprise a pad or mat upon which the sample of biologic tissue is placed.

The electrosurgical tool may comprise a bipolar device (such as bipolar forceps described herein), in which case at least two electrodes may be provided at the distal end of the tool, such that a potential difference can be created between the two electrodes which can vapourise tissue coming into contact therewith.

The one or more electrodes may be arranged and adapted to contact or surround a portion or sample of biologic tissue and evaporate or vapourise the portion or sample of biologic tissue to form an aerosol, smoke or vapour. One or more gas conduits may be provided to draw the aerosol, smoke or vapour through the tissue sampling device 1336 and introduce the aerosol, smoke or vapour into the ion inlet device 1334.

The portable apparatus 1300 may comprise a filter, for example a high efficiency particulate air ("HEPA") filter that may be arranged and adapted to filter gases and other matter that are exhausted from the tissue sampling device 1336, ion inlet device 1334 or ion analyser or mass spectrometer 1332.

The ion inlet device 1334 may be arranged and adapted to ionise particles within the aerosol, smoke or vapour and transfer the ionised particles to the ion analyser or mass spectrometer 1332.

According to an embodiment the ion analyser or mass spectrometer 1332 may comprise an ion mobility spectrometer. According to another embodiment the ion analyser or mass analyser 1332 may comprise a mass spectrometer. According to a yet further embodiment the ion analyser or mass spectrometer 1332 may comprise the combination of an ion mobility spectrometer and a mass spectrometer.

As a result of the analysis, chemical information about the aerosol, smoke or vapour, and therefore the portion or sample of biologic tissue, may be obtained.

The portable apparatus 1300 may comprise a single stack or unit comprising both the instrument stack 1301 and the analytical stack 1330 and the components thereof. In this manner, the instrument stack 1301 and the analytical stack 1330 may be movable as a single unit.

The single stack or unit may be portable. For example, the single stack or unit may be located on wheels and/or be located on a track, such that the single stack or unit may be moved between different locations, for example different operating theatres. The single stack or unit 1301 may weigh less than 500 kg, 400 kg, 300 kg, 200 kg, 150 kg, 100 kg, 50 kg, 40 kg, 30 kg, 20 kg, 10 kg or 5 kg.

In various embodiments, an operating theatre may be provided comprising the portable apparatus 1300. The operating theatre may comprise a track arranged and adapted such that the portable apparatus 1300 can be moved along the track.

In various embodiments, a set of operating theatres may be provided, wherein the portable apparatus is movable between the operating theatres. A track may be arranged and adapted such that the portable apparatus 1300 can be moved along the track between the different operating theatres.

The camera monitor 1303 may be arranged and adapted to relay images or image data that is output from the camera unit 1307, so as to display the view from the distal end 1312 of the endoscope 1310.

An analysis monitor 1333 may be provided that is operatively connected to the analytical stack 1330. The analysis monitor 1333 may be arranged and adapted to display data that is output from the ion analyser or mass spectrometer 1332, for example mass spectral data or chemical information about the portion or sample of biologic tissue being analysed. Embodiments are envisaged wherein the analysis monitor is or forms part of a mobile device, for example a mobile tablet device.

In some embodiments, the camera monitor 1303 may be linked via an interface to the ion analyser or mass spectrometer. The interface may comprise a serial interface such as an RJ45 connector, an Ethernet connector, an RS232 connector, a USB connector, etc. The interface may also or instead be provided by a wireless interface such as a Wi-Fi connection, a Bluetooth connection, a ZigBee connection etc.

The camera monitor 1303 may be arranged and adapted to display data that is output from the ion analyser or mass spectrometer 1332, for example mass spectral data or chemical information about the portion or sample of biologic tissue being analysed. A processor or other processing unit may be arranged and adapted to superimpose the mass spectral data or chemical information on the image of the sample of biologic tissue shown on the camera monitor 1303.

In some embodiments, the analysis monitor 1333 may be linked via an interface to the camera unit 1307. The interface may comprise a serial interface such as an RJ45 connector, an Ethernet connector, an RS232 connector, a USB connector, etc. The interface may also or instead be provided by a wireless interface such as a Wi-Fi connection, a Bluetooth connection, a ZigBee connection etc.

The analysis monitor 1333 may be arranged and adapted to display images or image data that are output from camera unit 1307, for example mass spectral data or chemical information about the portion or sample of biologic tissue being analysed. A processor or other processing unit may be arranged and adapted to superimpose the images or image data on the mass spectral data or chemical information shown on the analysis monitor 1333.

In various embodiments, the camera monitor 1303 and the analysis monitor 1333 may be the same component, and a processor or other processing unit may be arranged and adapted to display the images or image data on the same screen, for example side-by-side or superimposed on top of each other.

In various embodiments, the analytical stack 1330 may be provided alone, such that the tissue sampling device 1336 may not be connected to an endoscope. The analytical stack 1330 may also comprise one or more surgical instruments, for example a rapid evaporative ionization mass spectrometry device or probe as described herein which may be connected to or form part or all of the tissue sampling device.

In a particular example, gastro-intestinal ("GI") cancers account for 23% of cancer-related deaths globally. Despite an increasing incidence, mortality from cancer has been decreasing over the last four decades. However, it is nonetheless estimated that a further 30-40% of these deaths can potentially be prevented. Accurate disease diagnosis and early treatment are key factors in improving cancer outcomes.

Early stage cancers and pre-malignant conditions can be successfully treated using electrocautery-based endoscopic techniques while the gold standard method for diagnosis remains white light endoscopic investigation of the GI tract with tissue biopsy.

It has been recently reported that GI cancer may be missed at endoscopy in up to 7.8% of patients who are subsequently diagnosed with cancer. A major advantage of current endoscopic procedures is that patients avoid the need for major surgery if their lesions are completely excised. However, re-intervention is necessary in up to 41% of patients due to incomplete excision.

As will become further apparent, a particular advantage of the devices disclosed herein is that they enable accurate real time mass spectral data to be obtained and utilised in order to reduce mis-diagnosis rates and improve complete resection rates.

Enhanced imaging techniques are being developed to improve diagnostic accuracy within the GI tract with particular emphasis upon spectroscopic characterization using elastic scattering spectroscopy, optical coherence tomography, multimodal imaging combining Raman spectroscopy, autofluorescence and narrow band imaging.

However, none of these approaches are currently used in mainstream clinical practice.

Mass spectrometry ("MS") based identification of tissues is known using imaging techniques, sampling probe/electrospray systems and the direct ambient ionization mass spectrometry investigation of tissues.

Rapid evaporative ionization mass spectrometry ("REIMS") has emerged from this latter group as a beneficial technology allowing in-situ real-time analysis by the utilization of electrosurgical tools as a mass spectrometry ion source.

Endoscopy with Snare

According to an aspect of the disclosure there is provided an apparatus comprising an endoscope and an electrosurgical probe, for example a rapid evaporative ionization mass spectrometry probe. The rapid evaporative ionization mass spectrometry probe may comprise a snare arranged and adapted to surround a portion of biologic tissue and evaporate or vapourise the portion of biologic tissue to form an aerosol.

FIG. 13B shows an embodiment of a device 1350 located at the distal end 1312 of the endoscope 1310 of FIG. 13A. The device 1350 may be, or form part of, the tissue sampling device 1336 as shown in FIG. 13A and may take the form of a hollow tube having one or more electrodes running through it, as described in more detail below.

The device 1350 may take the form of a rapid evaporative ionization mass spectrometry device or probe 1350 that may comprise an elongated tube 1352 and an electrode 1354 that may protrude from a distal end 1356 of the tube 1352. The electrode 1354 may take the form of a loop or snare as shown, or may take the form of a pointed or straight member that protrudes from the distal end 1312 of the endoscope 1310. In various embodiments, the electrode 1354 may take the form of bipolar forceps as shown with reference to FIG.

14A, or the electrode 1354 may take the form of a monopolar device as shown with reference to FIG. 14B.

In the embodiment of FIG. 13B, the two strands of the electrode located within the rapid evaporative ionization mass spectrometry device or probe 1350 may not come into contact with one another. For example, the strands could be kept separate by retaining the strands within respective sheaths, or other means.

The rapid evaporative ionization mass spectrometry device or probe 1350 may be retained within the endoscope in a channel 1358, which may be referred to as an instrument channel. The channel 1358 may start at the junction 1325 (see FIG. 13A), if provided, and may be arranged and adapted to house components from the analytical stack 1330, such as the tissue sampling device 1336, which in the illustrated embodiment takes the form of a rapid evaporative ionization mass spectrometry device or probe 1350.

The endoscope 1310 may further comprise one or more optical fibers 1360. As discussed in reference to FIG. 13A above, these may be arranged and adapted to transmit light from a light source to the distal end 1312 of the endoscope 1310. The one or more optical fibers 1360 may be arranged and adapted to transmit light from the distal end 1312 of the endoscope 1310 to a camera or charge-coupled device ("CCD").

Instead of optical fibers, data cables or other tubing may be provided, depending on the application at hand. If it was desired to transfer a gas to the distal end 1312 of the endoscope 1310, then a gas tube may be provided in place of one of the optical fibers, which gas tube may be connected to a gas source, for example a source of insufflation gas. The outlet (or further outlets) of the gas tube may be located anywhere along the endoscope 1310.

The device 1350 may be arranged and adapted to apply a voltage to a portion 1370 of the sample to generate an aerosol (or surgical smoke) 1372. This may then be sucked or otherwise drawn into the device 1350 and may then be transferred to the ion analyser or mass spectrometer 1332 (FIG. 13A) via a gas path 1374. Fenestrations (or holes) 1365 may be provided in the outer surface of the device 1350 so as to provide more opportunity for the aerosol to be transferred into the device 1350.

In some embodiments, the device 1350 may comprise a plurality of channels, wherein a first channel may house the electrode 1354 (or electrodes) and a second channel may be a gas channel arranged and adapted to transfer the aerosol to the ion analyser or mass spectrometer 1332. The second channel may be located coaxially around the first channel.

A tool or electrode deployment opening 1362 is provided at the distal end 1356 of the device 1350 and the electrode (or other tool) may be arranged and adapted such that it can be retracted into and extended out of the opening 1362.

In the illustrated example, the electrode 1354 may be deployed around a growth or "polyp" 1370 and this growth 1370 may be located on the membrane 1342 of a stomach 1340.

A resection may be undertaken using the electrode as shown in FIG. 13B, if desired. In use, the snare 1354 may be extended and deployed over the growth 1370 so as to surround it. The snare 1354 may then be retracted so as to form a tight seal around a lower portion of the growth 1370. In doing so, the growth 1370 may at least partially or totally block the tool deployment opening 1362 of the tube 1352 during resection, as can be seen from FIG. 2B.

Upon a voltage being applied to the electrode 1354, the aerosol 1372 produced by the resection may be aspirated through the fenestrations 1365 which may be provided on the outer surface of the device 1350.

The provision of fenestrations 1365 on the outer surface of the device 1350 and which are spaced apart from the opening 1362 may be beneficial since the fenestrations or aspiration ports 1365 allow surgical smoke and/or aerosol to be aspirated when the tool deployment opening 1362 is at least partially or totally blocked.

The aerosol particles which enter the device 1350 via the fenestrations or aspiration ports 1365 may then be transferred to the ion analyser or mass spectrometer 1332 via tube 1352 and/or tissue sampling device 1336 (which, as discussed above, may also be the same component).

The device 1350 as shown may also be connected to, or form part of, the proximal end 1312 of an endoscope 1310. The tubing 1352 may be connected directly to the ion inlet device 1334 (for example an inlet capillary or ion sampling orifice thereof) of the ion analyser or mass spectrometer 1332. It will be understood that the ion analyser or mass spectrometer may be spaced apart from to the point of evaporation. One or more aerosol or gas channels may be located within the tube or tubing 1352 to transfer aerosol to the ion analyser or mass spectrometer 1332.

Laparoscopy and Laparoscopy Tools

As discussed above the endoscope described in relation to the embodiments of FIGS. 13A and 13B may be used in laparoscopy. In such a situation, the endoscope (or laparoscope), or an end portion thereof may be rigid, for example the endoscope may be constructed of metal or a rigid plastic, and/or may be arranged and adapted to perform a laparoscopy procedure (keyhole surgery).

FIG. 13C shows a laparoscope 1310 that may comprise a rigid end portion 1380 that may be attached to a flexible portion 1382. The distal end 1312 may comprise the same features as discussed above in respect of FIG. 13B, for example a rapid evaporative ionization mass spectrometry device 1350 may be arranged and adapted to protrude from the distal end 1312 in order to generate an aerosol or surgical smoke, which may then be transferred back to an ion analyser or mass spectrometer via fenestrations in the device 1350.

The end portion 1380 of the laparoscope 1310 may comprise an elongated portion 1381 that may have a width 1384 (or thickness, diameter, etc.) and a length 1386. The width 1384 may be uniform or substantially uniform over the length 1386 of the elongated portion 1381. The elongated portion 1381 may be arranged and adapted to be inserted into a small incision in a human or animal body, for example an incision having a length of less than 20 mm, 15 mm, 10 mm or 5 mm.

The width 1384 may be less than 20 mm, 15 mm, 10 mm or 5 mm.

The length may be greater than 5 mm, 10 mm, 15 mm, 20 mm, 25 mm, 30 mm, 35 mm, 40 mm, 50 mm, 60 mm, 70 mm, 80 mm, 90 mm, 100 mm, 150 mm, 200 mm, 300 mm, 400 mm or 500 mm.

The end portion 1380 may comprise a handle to aid in holding and moving the laparoscope 1310. The handle may be located at or adjacent to the junction 1396 between the flexible portion 1382 and the rigid end portion 1380. The handle may be rigid and may form part of the same rigid element as the rigid end portion 1380. The handle may be arranged and adapted to move or guide the rigid end portion 1380 and/or the elongated portion 1381, for example during a surgical procedure such as a laparoscopy.

An apparatus may comprise the various surgical devices disclosed herein, for example a laparoscope as described above in relation to FIGS. 13A, 13B and 13C, a surgical robot as described above in relation to FIGS. 15A and 15B, an electrosurgical probe, for example a rapid evaporative ionization mass spectrometry device or probe, or an electrosurgical tool. The surgery may be a laparoscopy.

According to an aspect of the disclosure there is provided a tool for use in laparoscopy, comprising an endoscope or laparoscope (e.g. the endoscope or laparoscope 1310 described above and with reference to FIG. 13C) and a rapid evaporative ionization mass spectrometry probe (e.g., the rapid evaporative ionization mass spectrometry probe 1350 described above in relation to FIG. 13B).

The rapid evaporative ionization mass spectrometry probe 1350 may be located at a distal end 1312 of the endoscope 1310. The tool, for example an elongated portion 1381 thereof, may be insertable through a small (e.g., less than 5 cm, 4 cm, 3 cm, 2 cm or 1 cm) incision in human or animal tissue. The tool may comprise an elongate tube or tubing, and the endoscope and rapid evaporative ionization mass spectrometry probe may form part of the elongate tube or tubing.

Insufflation (e.g., Using $CO_2$)

According to an embodiment there is provided an apparatus comprising an electrosurgical device, for example a rapid evaporative ionization mass spectrometry device or probe, and an insufflator. The apparatus may comprise a surgical instrument, for example an endoscope or laparoscope as discussed herein with reference to FIG. 13C, which may comprise the rapid evaporative ionization mass spectrometry device or probe.

Referring to FIG. 13C, the surgical instrument (e.g., laparoscope 1310) may comprise a gas channel for transferring gas from the insufflator into a cavity (e.g., a body cavity). The insufflator may comprise a gas source and a means (e.g., a pump) for fluidly transferring the gas source to the gas channel.

An insufflator gas tube 1390 may be provided to transfer the insufflation gas from the gas source to the laparoscope 1310, for example the end portion 1380 thereof. The gas tube 1390 may be in fluid communication with an internal gas passage 1394 of the laparoscope 1310 and may connect thereto via a connector 1391.

The laparoscope 1310 may comprise one or more insufflation gas outlets 1392 located in a portion of the laparoscope that is configured to be inserted into the body cavity.

The internal gas passage 1394 may run at least partially along the length of the laparoscope 1310. The one or more outlets 1392 of the internal gas passage 1394 may be located at the distal end 1312, elongated portion 1381 or end portion 1380 of the laparoscope, for example within 10 mm, 15 mm, 20 mm, 25 mm, 30 mm, 35 mm, 40 mm, 45 mm, 50 mm, 60 mm, 70 mm, 80 mm, 90 mm, 100 mm, 200 mm or 300 mm of the distal end 1312 (i.e., the end configured to be inserted into a human or animal specimen). The internal gas passage 1394 may be next to or connected to an optical fiber that may be connected to a camera at the distal end of the laparoscope, for example the one or more optical fibers 1360 discussed above. The gas source may comprise a carbon dioxide ("$CO_2$") gas source.

The laparoscope may be an endoscope or laparoscope as described above in relation to FIGS. 13A and 13B.

Surgical Instruments and Optimised Probe for Intraoperative Diagnosis

According to an embodiment there is provided a surgical instrument comprising a rapid evaporative ionization mass spectrometry device or probe. The surgical instrument may form part of a surgical stack 1301 as described above in relation to FIG. 13A. The surgical instrument may comprise an endoscope or laparoscope, and the rapid evaporative ionization mass spectrometry device or probe may comprise a surgical diathermy probe. The rapid evaporative ionization mass spectrometry probe may comprise one or more electrodes configured to evaporate or vapourise biologic tissue to form an aerosol comprising particles of the biologic tissue. The rapid evaporative ionization mass spectrometry probe may further comprise a tube or other means for transferring the particles to a mass analyser and/or ion mobility analyser or mass spectrometer.

According to an embodiment there is provided a rapid evaporative ionization mass spectrometry device or probe for use in an intraoperative diagnosis. The rapid evaporative ionization mass spectrometry device or probe may form part of a surgical instrument, for example an endoscope or laparoscope, and the rapid evaporative ionization mass spectrometry device or probe may comprise a surgical diathermy probe.

According to an embodiment there is provided a method of surgery, comprising using a rapid evaporative ionization mass spectrometry device or probe in an intraoperative diagnosis. The method may comprise identifying tissue for analysis, using the rapid evaporative ionization mass spectrometry device or probe to generate an aerosol comprising particles of the identified tissue, and analysing the particles. The analysing may comprise mass analysing and/or ion mobility analysing and/or a combination of mass and ion mobility analysing.

The method may comprise identifying a plurality of tissue samples for analysis, using the rapid evaporative ionization mass spectrometry device or probe to generate an aerosol comprising particles of each identified tissue sample, and analysing and/or ion mobility analysing the particles of each identified tissue sample. The analysing may comprise mass analysing and/or ion mobility analysing and/or a combination of mass and ion mobility analysing. The particles of each identified tissue sample may be mass analysed separately. The method may comprise outputting one or more mass spectra and/or ion mobility data (or data derived from mass spectra and/or ion mobility data) from each tissue sample, and optionally comparing the mass spectra and/or ion mobility data (or data derived from mass spectra and/or ion mobility data) from each tissue sample and optionally identifying differences between the different tissue samples.

The method may comprise using the rapid evaporative ionization mass spectrometry device or probe to search for a particular compound or compounds in the tissue, and may comprise searching or identifying the compound or compounds in mass spectra produced from the tissue or tissue samples.

Each tissue sample may be taken from the same part of the body or the same organ. Alternatively, each tissue sample may be taken from a different part of the body or a different organ.

The rapid evaporative ionization mass spectrometry device or probe may be optimised for surgical use. For example, the rapid evaporative ionization mass spectrometry device or probe, or the one or more electrodes thereof, may be miniaturised and/or one or more of the largest dimension, length, width and depth of the rapid evaporative ionization mass spectrometry device or probe may be less than 5 cm, 2 cm, 1 cm or 5 mm. The one or more electrodes may have a surface area, for example an exposed surface area less than 200 $mm^2$, 100 $mm^2$, 50 $mm^2$, 40 $mm^2$, 30 $mm^2$, 20 $mm^2$ or 10 $mm^2$, 2 $mm^2$, 1 $mm^2$, 0.5 $mm^2$, 0.4 $mm^2$, 0.3 $mm^2$, 0.2 $mm^2$ or 0.1 $mm^2$.

The rapid evaporative ionization mass spectrometry device or probe may be shaped such that it can be surgically inserted into a human or animal body. For example, the rapid evaporative ionization mass spectrometry device or probe may be elongated, or form part of an elongated tube or tubing, and/or form part of a surgical instrument such as an endoscope or laparoscope.

FIG. 14A shows an embodiment of a probe 1400 that may be optimised for surgical use. The probe may be a rapid evaporative ionization mass spectrometry device or probe and/or may be operatively connected to a surgical instrument such as those described above. The probe 1400 is similar to (or the same as) the bipolar forceps described above in relation to FIG. 1, and may comprise a small tip portion 1402 to aid in surgical procedures.

The probe as illustrated comprises a bipolar device, and may comprise two electrodes 1404 at the tip portion 1402. The tip portion 1402 may comprise two arms or pincers 1410, which may be flexible and/or hinged such that the electrodes 1404 at the tip portion 1402 may be brought closer together (or into contact) with one another.

One or more holes 1406 may be located at the tip portion 1402, for example at one of the electrodes 1404, so as to transfer aerosol particles generated by the probe to an ion analyser or mass spectrometer 8 via an internal passage 1408 and tubing 6 (see also FIG. 1). The one or more holes 1406 may, alternatively or additionally, be located anywhere on the probe, and may be arranged and adapted to transfer aerosol particles as described above. For example, the one or more holes 1406 may be located along the arms 1410 and/or outside of the tip portion 1402.

The electrodes 1404 located at the tip portion 1402 may be sharpened and may have a contact area (e.g., surface area) less than 2 $mm^2$, 1 $mm^2$, 0.5 $mm^2$, 0.4 $mm^2$, 0.3 $mm^2$, 0.2 $mm^2$ or 0.1 $mm^2$. The contact area may be defined as the area of the tip portion 1402, for example the external or exposed surface area of the tip portion of the electrodes 1404.

Alternatively (or additionally), the contact area of the tip portion 1402 may be defined as the area of the tip portion that is within a distance d from the end of the tip portion, wherein d may be 10 mm, 5 mm, 4 mm, 3 mm, 2 mm, 1 mm, 0.8 mm, 0.6 mm, 0.5 mm, 0.4 mm, 0.3 mm, 0.2 mm or 0.1 mm.

A smaller contact area (or increased sharpness) can assist in minimally-invasive or non-invasive surgery, since the electrical contact area is minimised. A lower voltage may also be used in addition to (or alternatively to) providing a relatively small contact area.

The surgical instrument may comprise a voltage supply arranged and adapted to apply a voltage to the electrodes 1404 located at the tip portion 1402. The applied voltage may be less than 3 kV, 2.5 kV, 2 kV, 1.5 kV, 1 kV, 500 V, 400 V, 350 V, 300 V, 250 V, 200 V, 150 V, 100 V, 50 V, 20 V or 10 V. One or more electrical wires 9 may be provided in order to apply the voltage and these may connect to the probe 1400 at a connecting portion thereof. One or more internal conductive wires 1412 or other means may be provided to apply the voltage to the electrodes 1404.

This may be different from invasive surgery using an electrosurgical tool, which typically can involve applied voltages of 1 kV, and contact areas of greater than 10 $mm^2$. As such, the probe 1400 described in relation to FIG. 14 can be considered to be optimised for minimally-invasive or non-invasive surgery. When operating the probe 1400, for example, it may not have a high enough voltage or surface area to cut or score tissue.

A voltage or current limiter may be provided, for example in the surgical instrument, voltage supply or probe 1400 that may be arranged and adapted to limit the current passed through or voltage applied to the electrodes 1404. The voltage or current limiter may be arranged and adapted to limit the voltage applied to the electrodes 1404 to 3 kV, 2.5 kV, 2 kV, 1.5 kV, 1 kV, 500 V, 400 V, 350 V, 300 V, 250 V, 200 V, 150 V, 100 V, 50 V, 20 V or 10 V peak or RMS. The voltage or current limiter may be arranged and adapted to limit the current supplied to the electrodes 1404 to 0.02 mA, 0.04 mA, 0.06 mA, 0.08 mA, 0.1 mA, 0.2 mA, 0.3 mA, 0.4 mA, 0.5 mA, 0.6 mA, 0.7 mA, 0.8 mA, 0.9 mA or 1 mA peak or RMS.

The voltage or current limiter may alternatively or additionally be arranged and adapted to limit the power supplied to the electrodes 1404. The voltage or current limiter may be arranged and adapted to limit the power supplied to the electrodes 1404 to 1 W, 5 W, 10 W, 20 W, 30 W, 40 W, 50 W, 60 W, 70 W, 80 W, 90 W, 100 W, 120 W, 140 W, 160 W, 180 W or 200 W peak or RMS.

The probe 1400 may be operatively connected to an ion analyser or mass spectrometer, for example an ion analyser or mass spectrometer forming part of an analytical stack 1330 as described above in relation to FIG. 13A. The probe 1400 may be connected to the ion analyser or mass spectrometer via an tissue sampling device or tubing, for example the tissue sampling device 1336 as described above in relation to FIG. 13A, or the tubing 6 shown in FIG. 1.

The tissue sampling device or tubing, or other connecting means connecting the probe 1400 to the ion analyser or mass spectrometer, for example a first vacuum stage thereof, may have a maximum diameter of less than 1 mm, 0.9 mm, 0.8 mm, 0.7 mm, 0.6 mm, 0.5 mm, 0.4 mm, 0.3 mm, 250 µm, 200 µm, 150 µm, 100 µm, 50 µm, 40 µm, 30 µm, 20 µm or 10 µm. A small diameter tubing can assist in transferring the aerosol generated by the probe 1400 to the ion analyser or mass spectrometer quickly. The tissue sampling device or tubing may connect the probe 1400 to an ion inlet device, or first vacuum stage of the ion analyser or mass spectrometer.

An alternative probe to that shown in FIG. 14A is shown in FIG. 14B. The probe 1450 of FIG. 14B has the same features as the probe of FIG. 14A but, instead of two arms 1410 a single arm 1460 is provided with a single electrode 1454 located at the tip portion 1452. In such "monopolar" embodiments, instead of a potential difference being created between electrodes of the probe (and tissue located therebetween), a potential difference may be created between the point of contact of the electrode and a counter electrode placed into contact with the sample being analysed.

The features described above in respect of the probe 1400 of FIG. 14A and its respective features and arrangements apply equally to the probe 1450 shown in FIG. 14B. Similar features have been provided with reference numerals with an additional "50" added to them, so that e.g., the tip portion of the probe in FIG. 14B is indicated by reference numeral 1452, and these features can be interchanged with those described above in reference to FIG. 14A.

Rapid Evaporative Ionisation Mass Spectrometry Device as a "Point Probe" and Real-Time Beam Diagnostics According to an aspect there is provided an apparatus comprising a surgical instrument comprising an electrosurgical tool, for example a rapid evaporative ionization mass spectrometry device or probe, an ion analyser or mass spectrometer and a control system. The surgical instrument may form part of an analytical stack 1301 and/or apparatus 1300 as described above in relation to FIG. 13A, for example comprising a camera monitor 1303 and/or an analysis monitor 1333 (which may also be the same component). The rapid evaporative ionization mass spectrometry device or probe may form part of an endoscope or laparoscope as described herein.

The electrosurgical tool or rapid evaporative ionization mass spectrometry probe may be a rapid evaporative ionization mass spectrometry probe as described herein with reference to FIGS. 14A-B, or a bipolar forceps probe as described herein with reference to FIG. 1.

The electrosurgical tool or rapid evaporative ionization mass spectrometry probe may comprise one or more electrodes configured to evaporate or vapourise biologic tissue to form an aerosol comprising particles of the biologic tissue, and the ion analyser or mass spectrometer may be arranged and adapted to mass analyse or ion mobility analyse the particles, and the data may comprise mass spectra produced from the mass analysis.

The control system may be arranged and adapted to process data from the ion analyser or mass spectrometer and output analyte information for use in surgery. The analyte information may comprise mass spectral or chemical data associated with specific parts of the biologic tissue or other sample being analysed.

The control system may be arranged and adapted to display the analyte information on a monitor (e.g., the camera monitor 1303 or analysis monitor 1333 or a mobile device, for example a mobile tablet device). The analyte information may be displayed or recorded as a function of another variable, for example location (e.g., distance, or coordinates for example in a 3-dimensional environment), time, etc. In this manner, the analyte information (e.g., mass spectral data and/or ion mobility data, or data derived from the mass spectral and/or ion mobility data, or chemical data) may be displayed or recorded with the other variable and this can improve surgical procedures.

For example, during surgery a surgeon may use the information provided by the control system and/or displayed on the monitor to help guide a surgical procedure. If cancer tissue is found using the probe, then the voltage may be increased so as to remove or vapourise this cancer tissue. Having vapourised the cancer tissue, the control system may alert the surgeon that the tissue is not cancerous, and the voltage may be lowered.

It is envisaged that this functionality may happen automatically. For example, the control system may be arranged and adapted to monitor the information output from the ion analyser or mass spectrometer and alter, adjust or vary an operating parameter in response.

For example, the control system may be arranged and adapted to alter, adjust or vary a voltage applied to the electrosurgical tool (e.g., by a voltage supply) in response to the information output from the ion analyser or mass spectrometer. If cancer tissue is found using the probe, then the voltage applied to the electrosurgical tool may be automatically increased so as to remove or vapourise this cancer tissue. Having vapourised the cancer tissue, the control system may automatically lower the voltage applied to the electrosurgical tool.

This kind of surgery may be known as chemically-guided surgery, in which real-time information about the tissue that is in contact with the probe may be provided to the surgeon, for example via a monitor as described above.

According to an embodiment there is provided a method, for example a method of chemically-guided surgery, comprising using a rapid evaporative ionization mass spectrometry probe to analyse a sample (e.g., biological tissue, biologic matter, a bacterial colony or a fungal colony), and using an ion analyser or mass spectrometer to provide real-time analysis (e.g., mass spectral or ion mobility analysis) of the sample.

The rapid evaporative ionization mass spectrometry probe may be a rapid evaporative ionization mass spectrometry probe as described herein with reference to FIG. 14A-B, or a bipolar forceps probe as described herein with reference to FIG. 1.

The method may comprise guiding or scanning the rapid evaporative ionization mass spectrometry probe over a sample (e.g., using a robot, for example a surgical robot as described below) and optionally using the real-time analysis to aid or provide guidance of the rapid evaporative ionization mass spectrometry probe.

The method may comprise using the rapid evaporative ionization mass spectrometry probe to search, identify or scan for a particular compound or compounds. The method may comprise changing the direction of the rapid evaporative ionization mass spectrometry probe based on the real-time analysis.

If the compound or compounds are identified then the method may comprise continuing to guide or scan the rapid evaporative ionization mass spectrometry probe in the same direction. If the compound or compounds are not identified the method may comprise changing the direction of the rapid evaporative ionization mass spectrometry probe. The method may comprise performing a different type of guiding or scan pattern if the particular compound or compounds are identified.

For example, once the particular compound or compounds are identified, the method may comprise transferring from a first scan pattern to a second, different scan pattern. The first scan pattern may be linear, for example performing a scan at points in a line, wherein the points are separated by a distance. The second scan pattern may comprise a spiral scan pattern. In this manner, if a compound or compounds of interest are identified at a linear scan point, the method may comprise switching to a spiral scan pattern centered around the scan point of interest.

The methods described above may be performed by a control system, for example the rapid evaporative ionization mass spectrometry probe may form part of a robotic instrument (e.g., a surgical robotic instrument or an apparatus for performing surgery comprising a handheld manipulator as described below). The rapid evaporative ionization mass spectrometry probe or control system or a processing unit thereof may be programmed to perform the guiding or scanning procedures described above.

Alternatively, or additionally the rapid evaporative ionization mass spectrometry probe may be controlled or controllable using a user interface.

Remotely Operated Instrumentation for Surgical Use

Figure 15A:
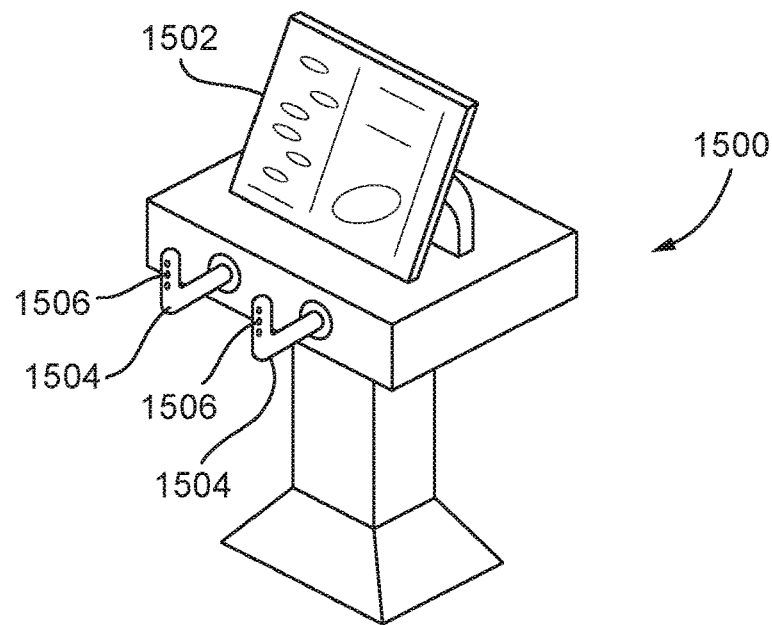
FIG. 15A shows part of an apparatus for performing surgery, wherein a surgeon may use a handheld manipulator to control a robotic device remote to the handheld manipulator

According to various embodiments robotic surgery methods are disclosed wherein a control device, for example a handheld manipulator, may be used to remotely control a surgical robot. An apparatus is shown in FIGS. 15A and 15B and comprises a handheld manipulator 1500 (FIG. 15A) as well as a surgical robot or robotic probe 1550 (FIG. 15B).

Robotic surgical techniques have been developed in which the handheld manipulator 1500 may be used to remotely control a surgical robot 1550. Typically, during such a procedure a surgeon's hand movements may be translated by a computer into smaller, precise movements of robotic instruments inside a patient's body, described in more detail below.

Other procedures are envisaged outside of a hospital environment. For example, on a battlefield it can sometimes be difficult or impossible for a human to attend to an injured soldier. It is envisaged that the surgical robot may form part of a battlefield medical unit (e.g., part of a larger robot that can move across battlefield terrain) and be arranged and adapted to perform surgical procedures (e.g., amputations) on the battlefield.

Figure 15B:
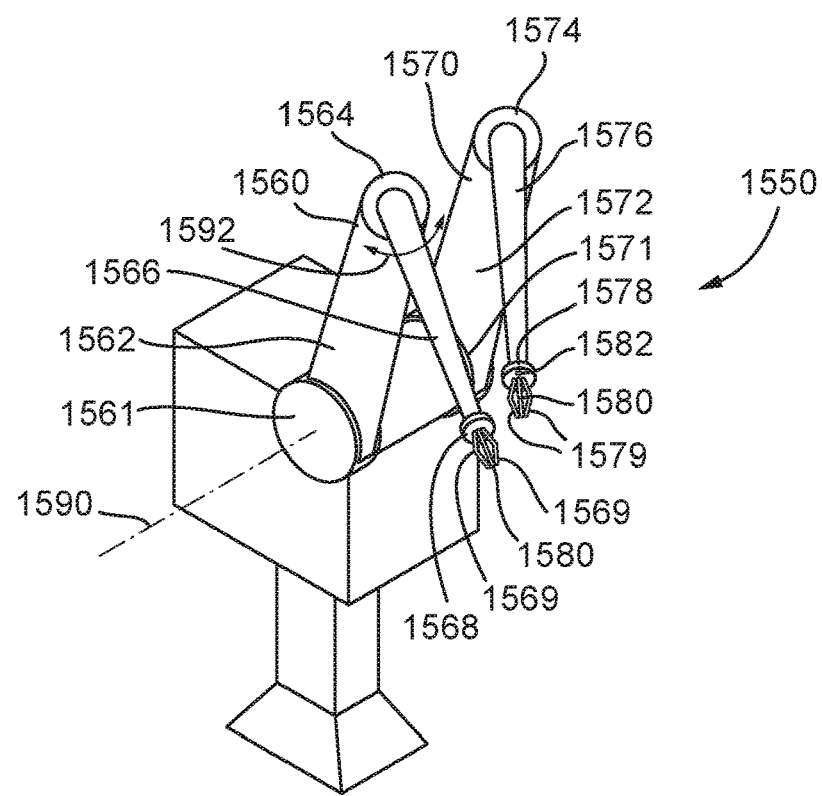
FIG. 15B shows an embodiment of such a robotic device.

The surgical robot 1550 may comprise one or more arms, such as a right arm 1570 and a left arm 1560 as shown in FIG. 15B. Each arm may comprise one or more joints and sub-portions to allow movement of the arm in various directions.

In the illustrated example, the right arm 1560 comprises a first rotating member 1561 that may be arranged and adapted to rotate around a first axis of rotation 1591. The first rotating member 1561 may be connected to a first arm portion 1562 that may be in the form of an elongate member.

At a distal end of the first arm portion 1562 may be a rotating cup 1564 that is operatively connected to the first arm portion 1562. The rotating cup 1564 may be arranged and adapted to rotate independently of the first arm portion 1562 in the direction shown at arrow 1592. The rotating cup 1564 may be connected to a second arm portion 1566 and the second arm portion 1566 may be arranged and adapted to rotate with the rotating cup 1564 in the directions shown by arrow 1592.

Located at the distal end of the second arm portion 1566 may be a hand unit 1568. The hand unit may be operatively connected to one or more actuators or instruments 1569, and may be arranged and adapted to control movement of the one or more instruments 1555 and/or surgical device 1580.

It should be noted that the left arm 1570 comprises the same components as the right arm. These are indicated in FIG. 15B with reference numerals having an additional "10", for example the rotating cup of the left arm is indicated by reference numeral 1574.

FIG. 15B shows the instruments schematically, for example in the form of fingers or pincers 1569 and 1579. These simple instruments are given for example purposes only, and the instruments may (alternatively or additionally) include fingers, pincers, grabbers, knives, scalpels, drills or any other tools that may be useful during a surgical procedure.

The one or more instruments 1569,1579 may be movable in any direction through use of appropriate bearings and motors. The one or more instruments 1569,1579 may be rotatable about any axis of rotation, and may be translatable towards and away from their respective hand unit 1568. It is possible that the instruments 1569,1579 may themselves comprise further instruments located at their distal ends. For example, a pincer 1569 may itself comprise a drill at its distal end, meaning that the instrument could be additionally used to drill into a sample held between the pincers.

The size of the one or more instruments 1569,1579 may be varied and adapted for any particular surgical procedure. For example, the instruments may have a largest dimension of less than or greater than 10 cm, 5 cm, 4 cm, 3 cm, 2 cm, 10 mm, 5 mm, 4 mm, 3 mm, 2 mm, 1 mm, 0.8 mm, 0.6 mm, 0.5 mm, 0.4 mm, 0.3 mm, 0.2 mm or 0.1 mm. The largest dimension may be defined as the largest straight-line distance between any two points located on the instrument. For example, in the case of a simple elongated rod, the largest distance would be equal to the length of the rod.

It will be appreciated that more or fewer arms may be provided on the surgical robot, and the arms themselves may comprise more or fewer components as required for a particular surgical procedure. More complex procedures will typically require a plurality of arms, each arranged and adapted to carry out a specific procedure or provided for a specific purpose. Alternatively, the surgical robot may be used to carry out a relatively simple procedure (e.g., an amputation), in which case a single arm may be provided.

The hand units 1568,1578 may comprise one or more cameras 1582 (only one is shown in the illustrated embodiment, but more could be provided as necessary). The cameras 1582 may be arranged and adapted to capture images or image data of the sample that is being manipulated by the surgical robot 1550.

One or more electrosurgical devices 1580, for example a rapid evaporative ionization mass spectrometry device or probe may be located on one or both of the hand units 1568, 1578. The one or more electrosurgical devices 1508 may be arranged and adapted to apply a voltage, for example via one or more electrodes located at a distal end thereof, to a sample that is being held or manipulated by the surgical robot 1550.

The one or more electrosurgical devices 1580 may be arranged and adapted to generate an aerosol, for example the electrodes may be arranged and adapted to generate analyte, smoke, fumes, liquid, gas, surgical smoke, aerosol or vapour when the probe is in contact with a sample being manipulated by the surgical robot 1550.

The one or more electrosurgical devices 1580 may be or comprise a rapid evaporative ionization mass spectrometry probe as described herein with reference to FIG. 14A-B, or a bipolar forceps probe as described herein with reference to FIG. 1.

The apparatus may include a handheld manipulator 1500 as shown in FIG. 15A.

The handheld manipulator 1500 may be operatively linked to the surgical robot via an interface (or communication means). The interface may comprise a serial interface such as an RJ45 connector, an Ethernet connector, an RS232 connector, a USB connector, etc. The interface may also or instead be provided by a wireless interface such as a Wi-Fi connection, a Bluetooth connection, a ZigBee connection etc. The interface may be via a satellite or other long-range wireless connection.

The handheld manipulator 1500 may be arranged and adapted to control the movement of the various parts of the surgical robot. A control system may be provided within the surgical robot that may be arranged and adapted to relay instructions sent it by the handheld manipulator into movement of the various parts of the surgical robot.

The handheld manipulator may comprise a monitor 1502, which may be in the form of a mobile device, for example a mobile tablet device, that may be arranged and adapted to display information concerning the surgical procedure and/or other information. One or more control devices, for example joysticks 1504 may be provided and the handheld manipulator may be configured such that movement of the control devices 1504 in a particular direction (or other type of activation of the control devices) causes a corresponding movement of the surgical robot 1550, or a particular component thereof, in a corresponding direction.

In the illustrated example, the type of movement caused by the joysticks 1504 may be changed or altered. For example, one or more buttons 1506 may be located on each joystick 1504 and activation or depression of these buttons 1506 may change the component being controlled, or the direction of movement of the component being controlled.

The control devices 1504 may be arranged and adapted to operate the one or more electrosurgical devices 1580. For example, the control devices 1504 may be arranged and adapted to send a signal to a voltage supply such that the voltage supply applied a voltage to the electrodes to generate an aerosol.

The actuators or instruments 1569,1579 may be configured to move according to commands from a user (e.g., a surgeon) of the handheld manipulator. Similarly, as discussed above the electrode may be controlled by the handheld manipulator, such that generation of the analyte, smoke fumes, liquid, gas, surgical smoke, aerosol or vapour can be controlled by the user.

Various embodiments may provide a rapid evaporative ionization mass spectrometry probe that is part of a robotically-controlled device. Movement and/or actuation of the device may be caused by movement of the handheld manipulator.

The surgical robot may take other forms than that shown in FIG. 15B. For example, the surgical robot may comprise an endoscopic or laparoscopic device, wherein an endoscope or laparoscope is provided in place of the arms. One or more actuators or instruments may be located at the distal end of the laparoscope or endoscope, which may be controlled by movement of the handheld manipulator.

The endoscopic or laparoscopic device may comprise a camera, for example a charge-coupled device ("CCD"), at a distal end of the endoscope. The camera may be configured to transmit images or image data to a video monitor or mobile device, for example a mobile tablet device (e.g., monitor 1502 shown in FIG. 15A) via a transmission cable and/or by wireless transmission.

The endoscopic device may comprise one or more instrument channels that travel at least partially along the endoscope. One or more electrosurgical devices, for example a rapid evaporative ionization mass spectrometry device or probe may be located at the distal end of the endoscope or laparoscope.

The probe and/or endoscopic or laparoscopic device may be part of a robotically-controlled laparoscopic device. The endoscopic or laparoscopic device may comprise one or more arms that are moveable in response to movement of the handheld manipulator.

The probe or endoscopic or laparoscopic device may comprise a rapid evaporative ionisation mass spectrometry ("REIMS") electrosurgical tool comprising one or more electrodes. The apparatus may comprise a device arranged and adapted to aspirate the analyte, smoke, fumes, liquid, gas, surgical smoke, aerosol or vapour.

The apparatus may comprise a mass spectrometer comprising: (i) a substantially cylindrical collision assembly having a first longitudinal axis; (ii) a heater for heating the collision assembly; (iii) a first device arranged and adapted to direct the analyte, smoke, fumes, liquid, gas, surgical smoke, aerosol or vapour onto said heated collision assembly along a second axis which is substantially orthogonal to said first axis in order to form analyte ions; and (iv) a mass analyser and/or ion mobility analyser for analysing and/or ion mobility analysing said analyte ions. The analysing may comprise mass analysing and/or ion mobility analysing and/or a combination of mass and ion mobility analysing.

According to various embodiments the control device (used to remotely control the surgical robot described above) may not be in the form of a handheld manipulator. Certain surgical techniques could instead be loaded into a memory on the surgical robot in the form of a set of movement instructions. This may be appropriate for simple medical procedures such as an amputation, and may be referred to as an automated method.

The rapid evaporative ionization mass spectrometry device or probe that may be incorporated into the surgical robot may be used to guide surgical procedures, whether these are automated using a set of instructions loaded on to the surgical robot, or using a handheld manipulator as described above.

For example, the rapid evaporative ionization mass spectrometry device or probe may be used to locate a particular tissue, for example bone or muscle tissue. Further steps in the surgical procedure may be conditional on the rapid evaporative ionization mass spectrometry device or probe locating a particular tissue in this manner.

This may be used especially in the case of automated methods. Information from the rapid evaporative ionization mass spectrometry device or probe may be used to decide where to perform a particular procedure that has been loaded into the memory of the surgical robot. The set of movement instructions that may be loaded onto the memory of the surgical robot may be a set of conditional instructions, wherein the conditions may relate to the data or information produced using the rapid evaporative ionization mass spectrometry device or probe.

Alternatively, or additionally, an alert system could be incorporated into the surgical robot and/or the handheld manipulator, wherein the alert system is arranged and adapted to output an alert based on data or information produced using the rapid evaporative ionization mass spectrometry device or probe. For example, an alert could sound on the surgical robot, or an alert message could pop up on a monitor if a certain compound was found in the aerosol analysed by the rapid evaporative ionization mass spectrometry device or probe device.

Miniature Rapid Evaporative Ionization Mass Spectrometry Device

According to an aspect of the disclosure there is provided an apparatus comprising a rapid evaporative ionization mass spectrometry device or probe, wherein the apparatus is miniaturised. For example, the apparatus, including the rapid evaporative ionization mass spectrometry device or probe may be sized such that it cannot be controlled or manipulated by a human.

The apparatus may comprise a robot arranged and adapted to control the miniaturised rapid evaporative ionization mass spectrometry device or probe. The largest dimension of the apparatus, rapid evaporative ionization mass spectrometry device or probe, or the one or more electrodes thereof, may be less than 5 cm, 2 cm, 1 cm, 5 mm, 2 mm, 1 mm, 0.5 mm or 0.1 mm.

The device or probe may be substantially the same as the probes shown in any of FIG. 14A, 14B, 16 or 17, but with the respective dimensions reduced. The miniaturised probe may be incorporated into a laparoscope or endoscope as described herein, for example the laparoscope or endoscope as described in relation to FIGS. 13A and 13B.

The miniaturised probe may form part of a surgical robot as described herein, for example the surgical robot and other apparatus as described in relation to FIGS. 15A and 15B. For example, the handheld manipulator may be operatively coupled to the miniaturised probe via one or more actuators.

The surgical robot may be arranged and adapted to perform small-scale surgery, such as brain surgery. Small-scale surgery may be defined as surgery that involves manipulation or destruction of tissue on a scale less than 10 mm, 5 mm, 4 mm, 3 mm, 2 mm, 1 mm, 0.5 mm, 0.4 mm, 0.3 mm, 0.2 mm or 0.1 mm.

The surgical robot may be arranged and adapted to move the probe in a stepped manner, wherein each step corresponds to a movement of less than 10 mm, 5 mm, 4 mm, 3 mm, 2 mm, 1 mm, 0.5 mm, 0.4 mm, 0.3 mm, 0.2 mm or 0.1 mm, for example in 3-dimensional space.

Alternatively, the surgical robot may be arranged and adapted to move the probe in a continuous manner. The surgical robot may be arranged and adapted to move the probe in single movements that are less than 10 mm, 5 mm, 4 mm, 3 mm, 2 mm, 1 mm, 0.5 mm, 0.4 mm, 0.3 mm, 0.2 mm or 0.1 mm in length, for example in 3-dimensional space and/or in one direction in 3-dimensional space.

Use of such a miniaturised device may aid surgical situations that require movement of a tool, for example the rapid evaporative ionization mass spectrometry device or probe, over very small distances, such as during brain surgery.

Ion Optics

According to an embodiment there is provided a method comprising analysing a sample using a rapid evaporative ionization mass spectrometry probe, analysing the sample, and adjusting ion optics based on the mass analysis. The analysing may comprise mass analysing and/or ion mobility analysing and/or a combination of mass and ion mobility analysing. The analysis may be carried out using any of the apparatus disclosed herein comprising an ion analyser or mass spectrometer, which may comprise the ion optics discussed in respect of these embodiments. For example, the analysis could be carried out using the mass spectrometers disclosed in respect of FIGS. 1, 2A-2C, 3, 4, 5A-5B, 11 or FIG. 13A-13B.

The method may comprise adjusting an electrostatic lens in response to the analysis, for example if a particular compound or compounds exceed or fall below a defined intensity limit, or if the overall intensity exceeds or falls below a defined intensity limit. The method may be carried out in real-time, for example during an intraoperative diagnosis. The method may comprise adjusting ion optics (e.g., electrostatic lens) based on a particular compound or compounds being located in a tissue sample that is being analysed. Adjustment of the ion optics (e.g., an electrostatic lens) may comprise adjusting the transmission of ions through the ion optics.

Alternative Energy Sources—Ultrasonic Probe

Embodiments are envisaged in which the electrosurgical tools disclosed herein, for example the rapid evaporative ionisation mass spectrometry device or probe, may be replaced or combined with other forms of energy generation. One example of this is ultrasound, which as described below may be used in surgical methods in addition to, or as a replacement for electrosurgery or rapid evaporative ionisation mass spectrometry technologies.

According to an embodiment there is provided a surgical instrument comprising an ultrasonic device, probe, aspirator, vapouriser or dissector. The ultrasonic device may be referred to as an ultrasonic ablation instrument or ion source, and may correspond to the ultrasonic ablation ion source discussed above. The surgical instrument may form part of a surgical stack 1301 as described above in relation to FIG. 13A. The surgical instrument may comprise an endoscope or laparoscope. The ultrasonic device may be configured to aspirate or fragment biologic tissue and form a sampling fluid comprising particles of the biologic tissue. The rapid evaporative ionization mass spectrometry probe may further comprise a tube or other means for transferring the particles to a mass analyser and/or ion mobility analyser and/or mass spectrometer.

According to an embodiment there is provided a method of surgery, comprising using an ultrasonic device, probe, aspirator or dissector in an intraoperative diagnosis. The method may comprise identifying tissue for analysis, using the ultrasonic device, probe, aspirator or dissector to generate a sampling fluid comprising particles of the identified tissue, and analysing the particles. The analysing may comprise mass analysing and/or ion mobility analysing and/or a combination of mass and ion mobility analysing.

The method may comprise identifying a plurality of tissue samples for analysis, using the ultrasonic device, probe, aspirator or dissector to generate a sampling fluid comprising particles of each identified tissue sample, and analysing the particles of each identified tissue sample. The analysing may comprise mass analysing and/or ion mobility analysing and/or a combination of mass and ion mobility analysing. The particles of each identified tissue sample may be mass analysed or ion mobility analysed separately. The method may comprise outputting one or more mass spectra from each tissue sample, and optionally comparing the mass spectra from each tissue sample and optionally identifying differences between the different tissue samples.

The method may comprise using the ultrasonic device, probe, aspirator or dissector to search for a particular compound or compounds in the tissue, and may comprise searching or identifying the compound or compounds in mass spectra produced from the tissue or tissue samples.

Each tissue sample may be taken from the same part of the body or the same organ. Alternatively, each tissue sample may be taken from a different part of the body or a different organ.

The ultrasonic device, probe, aspirator or dissector may be optimised for surgical use. For example, the ultrasonic device, probe, aspirator or dissector may be miniaturised and/or one or more of the largest dimension, length, width and depth of the ultrasonic device, probe, aspirator or dissector may be less than 5 cm, 2 cm, 1 cm or 5 mm. The ultrasonic device, probe, aspirator or dissector may be shaped such that it can be surgically inserted into a human or animal body. For example, the ultrasonic device, probe, aspirator or dissector may be elongated, or form part of an elongated tube or tubing, and/or form part of a surgical instrument such as an endoscope or laparoscope. The ultrasonic device, probe, aspirator or dissector may be passed through a port or instrument channel of an endoscope or laparoscope, for example.

According to an aspect of the disclosure there is provided an apparatus comprising a rapid evaporative ionization mass spectrometry probe and a scalpel, wherein movement of the scalpel is assisted or caused by ultrasound. The apparatus may comprise an endoscope comprising the rapid evaporative ionization mass spectrometry probe and scalpel at a distal end thereof.

FIG. 16 shows an embodiment of a probe 1600 that may be optimised for surgical use. The probe may be a ultrasonic device, probe, aspirator or dissector and/or may be operatively connected to a surgical instrument such as those described above. The probe 1600 may comprise a tip portion 1602 to aid in surgical procedures.

Located at the tip portion 1602 of the probe 1600 is an ultrasonic piece 1604 that may be arranged and adapted to move and generate pulses of ultrasound. The ultrasonic piece 1604 may be located at the distal end of an arm 1610, which arm 1610 may be elongated for ease of use.

The movement may be directed towards and away from the probe as indicated at arrow 1620. This can direct pulses of ultrasound at tissue that is in close proximity to the probe 1600, which in turn can aspirate, dissect or fragment such tissue.

The frequency and/or amplitude of the ultrasound can be varied to suit different tissue and/or surgical techniques. For example, relatively low amplitude and/or frequency of pulses can be applied to dissect or fragment tissue having low intracellular bonds, such as fat, and relatively high amplitude pulses can be used to dissect or fragment tissue having high intracellular bonds, such as tendon.

One or more holes 1606 may be located at the tip portion 1602, for example within the ultrasonic piece 1604, so as to transfer tissue particles aspirated by the probe to an ion analyser or mass spectrometer 8 via an internal passage 1608 and tubing 6 (see also FIG. 1). The one or more holes 1606 may, alternatively or additionally, be located anywhere on the probe, and may be arranged and adapted to transfer particles as described above. For example, the one or more holes 1606 may be located along the arm 1610 and/or outside of the tip portion 1602.

The end surface 1605 of the ultrasonic piece 1604 (facing away from the probe 1600 and towards the sample) may have a surface area less than 2 mm$^2$, 1 mm$^2$, 0.5 mm$^2$, 0.4 mm$^2$, 0.3 mm$^2$, 0.2 mm$^2$ or 0.1 mm$^2$. The end surface may be concave (or convex).

The length of the ultrasonic piece 1604 that protrudes from the arm 1610 varies in use as the ultrasonic piece 1604 moves in and out of the arm 1610. However, the length of the ultrasonic piece 1604 that protrudes from the arm 1610 may not exceed 1 mm, 800 μm, 600 μm, 500 μm, 400 μm, 300 μm, 200 μm, 100 μm or 50 μm.

A smaller surface area 1605 of the ultrasound piece 1604 (or lower amplitude and/or frequency of the pulses) can assist in minimally-invasive or non-invasive surgery, since the pulse energy is minimised.

The surgical instrument may comprise a voltage supply arranged and adapted to power the movement of the ultrasonic piece 1604. The applied voltage may be less than 3 kV, 2.5 kV, 2 kV, 1.5 kV, 1 kV, 500 V, 400 V, 350 V, 300 V, 250 V, 200 V, 150 V, 100 V, 50 V, 20 V, 10 V, 5 V or 2 V. One or more electrical wires 9 may be provided in order to apply the voltage, and these may connect to the probe 1600 at a connecting portion thereof. One or more internal conductive wires or other means may be provided to apply the voltage to a transducer located within the probe 1600. The transducer may be arranged and adapted to convert the voltage to movement of the ultrasonic tip 1604.

The power supply may be arranged and adapted to apply a varying amount of voltage to the probe 1600, and the varying voltage may be used to vary the amplitude and/or frequency of the ultrasound produced by the ultrasonic tip 1604.

The probe 1600 may be operatively connected to an ion analyser or mass spectrometer, for example an ion analyser or mass spectrometer forming part of an analytical stack 1330 as described above in relation to FIG. 13A. The probe 1600 may be connected to the ion analyser or mass spectrometer via an tissue sampling device or tubing, for example the tissue sampling device 1336 as described above in relation to FIG. 13A, or the tubing 6 shown in FIG. 1.

The tissue sampling device or tubing, or other connecting means connecting the probe 1600 to the ion analyser or mass spectrometer, for example a first vacuum stage thereof, may have a maximum diameter of less than 1 mm, 0.9 mm, 0.8 mm, 0.7 mm, 0.6 mm, 0.5 mm, 0.4 mm, 0.3 mm, 250 μm, 200 μm, 150 μm, 100 μm, 50 μm, 40 μm, 30 μm, 20 μm or 10 μm. A small diameter tubing can assist in transferring the sampling fluid generated by the probe 1600 to the ion analyser or mass spectrometer quickly. The tissue sampling device or tubing may connect the probe 1600 to an ion inlet device, or first vacuum stage of the ion analyser or mass spectrometer.

The ultrasonic probe 1600 may be used to liquefy or otherwise disrupt tissue coming into contact with the ultrasonic piece 1604. This produces a liquid that can then be transferred to a mass spectrometer.

Embodiments are envisaged wherein the ultrasonic probe 1600 forms part of a laparoscope or endoscope. In such a situation, the arm 1610 of the probe may be located within the laparoscope or endoscope and may be longer than is depicted schematically in FIG. 16. The ultrasonic piece 1604 may be located at the distal end of the laparoscope or endoscope and may be arranged and adapted to aspirate or dissect tissue coming into contact with the distal end of the laparoscope or endoscope.

In various embodiments, a rapid evaporative ionization mass spectrometry device or probe may be used in conjunction with the ultrasonic probe 1600. For example, the probe 1600 may comprise an electrode, or the ultrasonic piece 1604 may also be an electrode, such that electrosurgical techniques can be combined with those of ultrasound.

In such embodiments, the ultrasonic probe 1600 may be arranged and adapted to vapourise the sampling fluid that is produced by the contact of the ultrasonic piece 1604 with tissue. The ultrasonic piece 1604 may be arranged and adapted to fragment and/or liquefy tissue to produce a sampling fluid in liquid form as described above.

The rapid evaporative ionization mass spectrometry device or probe may be arranged and adapted to vapourise the sampling fluid so as to produce an aerosol that can then be transferred to an ion analyser or mass spectrometer for analysis as described herein. Methods may involve providing a surgical instrument comprising an ultrasonic probe 1600 as described above, as well as a rapid evaporative ionization mass spectrometry device or probe (e.g., a rapid evaporative ionization mass spectrometry device or probe as described in relation to FIGS. 14A and 14B).

The method may comprise identifying a tissue sample for analysis, using the ultrasonic device, probe, aspirator or dissector to generate a sampling fluid comprising particles of the tissue sample (or portion of tissue sample), and analysing the particles of the tissue sample contained in the sampling fluid. The analysing may comprise mass analysing and/or ion mobility analysing and/or a combination of mass and ion mobility analysing.

The method may further comprise using the rapid evaporative ionization mass spectrometry device or probe to generate an aerosol comprising particles of the same tissue sample (or portion of tissue sample), and analysing the particles contained in the aerosol. The analysing may comprise mass analysing and/or ion mobility analysing and/or a combination of mass and ion mobility analysing.

The method may comprise outputting one or more mass spectra from each tissue sample, and optionally comparing or combining the mass spectra produced using the rapid evaporative ionization mass spectrometry device or probe with that produced using the ultrasonic device, probe, aspirator or dissector.

Alternative Energy Sources—Laser Probe

Further embodiments are envisaged in which the electrosurgical tools disclosed herein, for example the rapid evaporative ionisation mass spectrometry device or probe, may be replaced or combined with laser technology.

According to an embodiment there is provided a surgical instrument comprising a laser device, probe, aspirator or dissector. The laser device may be or comprise a laser ablation ion source as described above. The surgical instrument may form part of a surgical stack 1301 as described above in relation to FIG. 13A. The surgical instrument may comprise an endoscope or laparoscope. The laser device may be configured to aspirate or fragment biologic tissue and form an aerosol comprising particles of the biologic tissue. The laser probe may further comprise a tube or other means for transferring the particles to a mass analyser and/or ion mobility analyser and/or mass spectrometer.

According to an embodiment there is provided a method of surgery, comprising using a laser device, probe, aspirator or dissector in an intraoperative diagnosis. The method may comprise identifying tissue for analysis, using the laser device, probe, aspirator or dissector to generate an aerosol comprising particles of the identified tissue, and analysing the particles. The analysing may comprise mass analysing and/or ion mobility analysing and/or a combination of mass and ion mobility analysing.

The method may comprise identifying a plurality of tissue samples for analysis, using the laser device, probe, aspirator or dissector to generate a sampling fluid comprising particles of each identified tissue sample, and analysing the particles of each identified tissue sample. The analysing may comprise mass analysing and/or ion mobility analysing and/or a combination of mass and ion mobility analysing. The particles of each identified tissue sample may be mass analysed or ion mobility analysed separately. The method may comprise outputting one or more mass spectra from each tissue sample, and optionally comparing the mass spectra from each tissue sample and optionally identifying differences between the different tissue samples.

The method may comprise using the laser device, probe, aspirator or dissector to search for a particular compound or compounds in the tissue, and may comprise searching or identifying the compound or compounds in mass spectra produced from the tissue or tissue samples.

Each tissue sample may be taken from the same part of the body or the same organ. Alternatively, each tissue sample may be taken from a different part of the body or a different organ.

The laser device, probe, aspirator or dissector may be optimised for surgical use. For example, the laser device, probe, aspirator or dissector may be miniaturised and/or one or more of the largest dimension, length, width and depth of the laser device, probe, aspirator or dissector may be less than 5 cm, 2 cm, 1 cm or 5 mm. The laser device, probe, aspirator or dissector may be shaped such that it can be surgically inserted into a human or animal body. For example, the laser device, probe, aspirator or dissector may be elongated, or form part of an elongated tube or tubing, and/or form part of a surgical instrument such as an endoscope or laparoscope. The laser device, probe, aspirator or dissector may be passed through a port or instrument channel of an endoscope or laparoscope, for example.

FIG. 17 shows an embodiment of a probe 1700 that may be optimised for surgical use. The probe may be a laser device, probe, aspirator or dissector and/or may be operatively connected to a surgical instrument such as those described above. The probe 1700 may comprise a tip 1702 to aid in surgical procedures.

Located at the tip 1702 of the probe 1700 is an aperture 1704 that may be arranged and adapted to output a laser beam. The aperture 1704 may be located at the distal end of an arm 1710, which arm 1710 may be elongated for ease of use.

The laser beam may be directed away from the probe as indicated at arrow 1720. This can direct laser pulses at tissue that is in close proximity to the probe 1700, which in turn can aspirate, dissect or fragment such tissue.

The frequency and/or amplitude and/or wavelength and/or pulse duration of the laser can be varied to suit different tissue and/or surgical techniques. For example, a relatively low energy laser pulse can be applied to dissect or fragment tissue having low intracellular bonds, such as skin or fat, and relatively high energy pulses can be used to dissect or fragment tissue having high intracellular bonds, such as bone or tendon.

One or more holes 1706 may be located at the tip 1702, so as to transfer tissue particles aspirated by the laser to an ion analyser or mass spectrometer 8 via an internal passage 1708 and tubing 6 (see also FIG. 1). The one or more holes 1706 may, alternatively or additionally, be located anywhere on the probe, and may be arranged and adapted to transfer particles as described above. For example, the one or more holes 1706 may be located along the arm 1710 and/or outside of the tip 1702.

The tip 1702 may have a surface area less than 2 mm$^2$, 1 mm$^2$, 0.5 mm$^2$, 0.4 mm$^2$, 0.3 mm$^2$, 0.2 mm$^2$ or 0.1 mm$^2$. The end surface may be concave (or convex).

A smaller energy of the laser beam (or lower amplitude and/or frequency of the pulses) can assist in minimally-invasive or non-invasive surgery.

The surgical instrument may comprise a voltage supply arranged and adapted to power a laser source 1715. The laser source 1715 may be located within the probe 1700, or may be located external to the probe and connected thereto via one or more fiber optics or fiber optic cables. One or more electrical wires 9 may be provided in order to apply the voltage, and these may connect to the probe 1700 at a connecting portion thereof. If the laser source is external to the probe 1700, then the electrical wires 9 would be replaced by fiber optics.

The power supply may be arranged and adapted to apply a varying amount of voltage to the laser source 1715, and the varying voltage may be used to vary the applied energy of the laser pulse.

The probe 1700 may be operatively connected to an ion analyser or mass spectrometer, for example an ion analyser or mass spectrometer forming part of an analytical stack 1330 as described above in relation to FIG. 13A. The probe 1700 may be connected to the ion analyser or mass spectrometer via a tissue sampling device or tubing, for example the tissue sampling device 1336 as described above in relation to FIG. 13A, or the tubing 6 shown in FIG. 1.

The tissue sampling device or tubing, or other connecting means connecting the probe 1700 to the ion analyser or mass spectrometer, for example a first vacuum stage thereof, may have a maximum diameter of less than 1 mm, 0.9 mm, 0.8 mm, 0.7 mm, 0.6 mm, 0.5 mm, 0.4 mm, 0.3 mm, 250 µm, 200 µm, 150 µm, 100 µm, 50 µm, 40 µm, 30 µm, 20 µm or 10 µm. A small diameter tubing can assist in transferring the sampling fluid generated by the probe 1700 to the ion analyser or mass spectrometer quickly. The tissue sampling device or tubing may connect the probe 1700 to an ion inlet device, or first vacuum stage of the ion analyser or mass spectrometer.

The laser probe 1700 may be used to fragment or otherwise disrupt tissue coming into contact with the laser beam. This may produces an aerosol that can then be transferred to a mass spectrometer.

Embodiments are envisaged wherein the laser probe 1700 forms part of a laparoscope or endoscope. In such a situation, the arm 1710 of the probe may be located within the laparoscope or endoscope and may be longer than is depicted schematically in FIG. 17. The laser aperture 1704 may be located at the distal end of the laparoscope or endoscope and may be arranged and adapted to fragment or otherwise disrupt tissue located adjacent to the distal end of the laparoscope or endoscope.

In various embodiments, a rapid evaporative ionization mass spectrometry device or probe may be used in conjunction with the laser probe. For example, the probe 1700 may comprise an electrode such that electrosurgical techniques can be combined with the laser beam.

The rapid evaporative ionization mass spectrometry device or probe may be arranged and adapted to vapourise the same portion of tissue that is in contact with the laser beam, so as to produce an aerosol that can then be transferred to an ion analyser or mass spectrometer for analysis as described herein.

Methods may involve providing a surgical instrument comprising a laser probe 1700 as described above, as well as a rapid evaporative ionization mass spectrometry device or probe (e.g., a rapid evaporative ionization mass spectrometry device or probe as described in relation to FIGS. 14A and 14B).

The method may comprise identifying a tissue sample for analysis, using the laser device, probe aspirator or dissector to generate an aerosol comprising particles of the tissue sample (or portion of tissue sample), and analysing the particles of the tissue sample contained in the sampling fluid. The analysing may comprise mass analysing and/or ion mobility analysing and/or a combination of mass and ion mobility analysing.

The method may further comprise using the rapid evaporative ionization mass spectrometry device or probe to generate an aerosol comprising particles of the same tissue sample (or portion of tissue sample), and analysing the particles contained in the aerosol. The analysing may comprise mass analysing and/or ion mobility analysing and/or a combination of mass and ion mobility analysing.

The method may comprise outputting one or more mass spectra from each tissue sample, and optionally comparing or combining the mass spectra produced using the rapid evaporative ionization mass spectrometry device or probe with that produced using the laser device, probe aspirator or dissector.

The laser or laser source may be a surgical laser or laser source and/or may be arranged and adapted to break up, vapourise or cut a sample, for example biologic tissue. The apparatus may comprise an instrument, for example a surgical instrument, comprising the laser probe. The laser source may be or comprise a carbon dioxide laser source, argon laser source, neodymium-doped yttrium aluminium garnet ("Nd:YAG") laser source, erbium-doped yttrium aluminium garnet ("Er:YAG") laser source or potassium titanyl phosphate laser source.

Alternative Energy Sources—Hydrosurgery

Further embodiments are envisaged in which the electrosurgical tools disclosed herein, for example the rapid evaporative ionisation mass spectrometry device or probe, may be replaced or combined with hydrosurgery technology.

According to an embodiment there is provided a surgical instrument comprising a hydrosurgical device. The hydrosurgical device may be or comprise a fluid source and a nozzle for directing a fluid (e.g., from said fluid source) at a target at a high pressure (e.g., greater than 10,000 psi or 0.69 MegaPascals), for example a sample such as a biologic sample. The surgical instrument may form part of a surgical stack 1301 as described above in relation to FIG. 13A. The surgical instrument may comprise an endoscope or laparoscope. The hydrosurgical device may be configured to aspirate or fragment biologic tissue and form an aerosol comprising particles of the biologic tissue. The hydrosurgical probe may further comprise a tube or other means for transferring the particles to a mass analyser and/or ion mobility analyser and/or mass spectrometer.

According to an embodiment there is provided a method of surgery, comprising using a hydrosurgical device, probe, aspirator or dissector, for example in an intraoperative diagnosis. The method may comprise identifying tissue for analysis, using the hydrosurgical device, probe, aspirator or dissector to generate an aerosol comprising particles of the identified tissue, and analysing the particles. The analysing may comprise mass analysing and/or ion mobility analysing and/or a combination of mass and ion mobility analysing.

The method may comprise identifying a plurality of tissue samples for analysis, using the hydrosurgical device, probe, aspirator or dissector to generate a sampling fluid comprising particles of each identified tissue sample, and analysing the particles of each identified tissue sample. The analysing may comprise mass analysing and/or ion mobility analysing and/or a combination of mass and ion mobility analysing.

The particles of each identified tissue sample may be mass analysed and/or ion mobility analysed separately. The method may comprise outputting one or more mass spectra from each tissue sample, and optionally comparing the mass spectra from each tissue sample and optionally identifying differences between the different tissue samples.

The method may comprise using the hydrosurgical device, probe, aspirator or dissector to search for a particular compound or compounds in the tissue, and may comprise searching or identifying the compound or compounds in mass spectra produced from the tissue or tissue samples.

Each tissue sample may be taken from the same part of the body or the same organ. Alternatively, each tissue sample may be taken from a different part of the body or a different organ.

The hydrosurgical device, probe, aspirator or dissector may be optimised for surgical use. For example, the hydrosurgical device, probe, aspirator or dissector may be miniaturised and/or one or more of the largest dimension, length, width and depth of the hydrosurgical device, probe, aspirator or dissector may be less than 5 cm, 2 cm, 1 cm or 5 mm. The hydrosurgical device, probe, aspirator or dissector may be shaped such that it can be surgically inserted into a human or animal body. For example, the hydrosurgical device, probe, aspirator or dissector may be elongated, or form part of an elongated tube or tubing, and/or form part of a surgical instrument such as an endoscope or laparoscope. The hydrosurgical device may be passed through a port or instrument channel of an endoscope or laparoscope, for example.

In an embodiment, a probe may be optimised for surgical use. The probe may be a hydrosurgical device, probe, aspirator or dissector and/or may be operatively connected to a surgical instrument such as those described above. The probe may comprise a tip to aid in surgical procedures.

Located at the tip of the probe is a nozzle that may be arranged and adapted to output a fluid, for example a liquid such as water or a saline solution. The nozzle may be arranged and adapted to output a thin stream of the fluid.

The aperture or nozzle may have an output end or exit hole having a diameter or largest dimension in the range of about 0.05 mm to about 1 mm, 0.06 mm to about 0.8 mm, 0.07 to about 0.7 mm, about 0.08 to about 0.6 mm, about 0.09 to about 0.5 mm, about 0.1 mm to about 0.4 mm, about 0.1 mm to about 0.3 mm, about 0.1 mm to about 0.2 mm, about 0.1 mm to about 0.15 mm.

The aperture or nozzle may have an output end or exit hole having a cross-sectional area of about 50 mm² to about 150 mm², 60 mm² to about 140 mm², 70 mm² to about 130 mm², 80 mm² to about 120 mm², 90 mm² to about 110 mm², and 95 mm² to about 105 mm².

The size of the output end or exit hole can affect how aggressive the treatment is. The larger the hole, the less aggressive the treatment and vice-versa.

The nozzle may be located at the distal end of an arm, which arm may be elongated for ease of use.

The fluid jet may be directed away from the probe as indicated at arrow. This can direct the fluid at tissue that is in close proximity to the probe, which in turn can aspirate, dissect or fragment such tissue. Embodiments are contemplated wherein the fluid jet is directed across tissue, such as parallel to the tissue. The nozzle could be located at a point along the arm a distance from the tip, and be arranged and adapted to direct a stream of fluid from the outlet end or exit hole substantially parallel to the arm. In this manner the arm could be used like a knife.

The pressure and/or flow rate and/or pulse duration of the fluid can be varied to suit different tissue and/or surgical techniques. For example, a relatively low energy flow rate and/or pressure can be applied to dissect or fragment tissue having low intracellular bonds, such as skin or fat, and relatively high energy flow rate and/or pressure can be used to dissect or fragment tissue having high intracellular bonds, such as bone or tendon.

One or more holes may be located at the tip, so as to transfer tissue particles aspirated by the laser to an ion analyser or mass spectrometer 8 via an internal passage and tubing 6 (see also FIG. 1). The one or more holes may, alternatively or additionally, be located anywhere on the probe, and may be arranged and adapted to transfer particles as described above. For example, the one or more holes may be located along the arm and/or outside of the tip.

The tip may have a surface area less than 2 mm², 1 mm², 0.5 mm², 0.4 mm², 0.3 mm², 0.2 mm² or 0.1 mm².

A smaller energy of the fluid flow (or lower pressure and/or flow rate of the fluid) can assist in minimally-invasive or non-invasive surgery.

The surgical instrument may comprise a pump 1765 arranged and adapted to supply and/or pump the fluid. A tubing 9 may be provided in order to supply the fluid to the surgical instrument. The pump may be located within the probe, or may be located external to the probe and connected thereto via the tubing 9.

The pump may be arranged and adapted to apply a varying flow rate and/or pressure of the fluid to the nozzle, and the varying flow rate and/or pressure may be used to vary the applied energy of the fluid.

The pump and/or nozzle may be arranged and adapted to output fluid from the nozzle at a pressure between about 0.5 to about 1.5 MPa, about 0.6 to about 1.4 MPa, about 0.7 to about 1.3 MPa, about 0.8 to about 1.2 MPa, about 0.9 to about 1.1 MPa, or about 0.95 to about 1.05 MPa. The pump and/or nozzle may be arranged and adapted to output fluid from the nozzle at a pressure greater than 2 MPa or even 3 MPa in some applications.

The pump may be arranged and adapted to pump fluid at a flow rate of less than or greater than about 50 µl/min, or a flow rate selected from the group consisting of: (i) 50-100 µl/min; (ii) about 100-200 µl/min; (iii) about 200-500 µl/min; (iv) about 500-1000 µl/min; (v) about 1-2 ml/min; (vi) about 2-3 ml/min; (vii) about 3-4 ml/min; (viii) about 4-5 ml/min; (ix) about 5-10 ml/min; (x) about 10-50 ml/min; (xi) about 50-100 ml/min; (xii) about 100-200 ml/min; (xiii) about 200-300 ml/min; (xiv) about 300-400 ml/min; (xv) about 500-600 ml/min; (xvi) about 600-700 ml/min; (xvii) about 700-800 ml/min; (xviii) about 800-900 ml/min; (xix) about 900-1000 ml/min or greater than about 1000 ml/min.

The probe may be operatively connected to an ion analyser or mass spectrometer, for example an ion analyser or mass spectrometer forming part of an analytical stack 1330 as described above in relation to FIG. 13A. The probe may be connected to the ion analyser or mass spectrometer via a tissue sampling device or tubing, for example the tissue sampling device 1336 as described above in relation to FIG. 13A, or the tubing 6 shown in FIG. 1.

The tissue sampling device or tubing, or other connecting means connecting the probe to the ion analyser or mass spectrometer, for example a first vacuum stage thereof, may have a maximum diameter of less than 1 mm, 0.9 mm, 0.8 mm, 0.7 mm, 0.6 mm, 0.5 mm, 0.4 mm, 0.3 mm, 250 µm, 200 µm, 150 µm, 100 µm, 50 µm, 40 µm, 30 µm, 20 µm or 10 µm. A small diameter tubing can assist in transferring the sampling fluid generated by the probe to the ion analyser or mass spectrometer quickly. The tissue sampling device or tubing may connect the probe to an ion inlet device, or first vacuum stage of the ion analyser or mass spectrometer.

The hydrosurgical probe may be used to fragment or otherwise disrupt tissue coming into contact with the fluid. This may produce an aerosol or particles of tissue that can then be transferred to an ion analyser or mass spectrometer, for example via tubing 6.

Embodiments are envisaged wherein the hydrosurgical probe forms part of a laparoscope or endoscope. In such a situation, the arm of the probe may be located within the laparoscope or endoscope and may be longer. The nozzle may be located at the distal end of the laparoscope or endoscope and may be arranged and adapted to fragment or otherwise disrupt tissue located adjacent to the distal end of the laparoscope or endoscope.

In various embodiments, a rapid evaporative ionization mass spectrometry device or probe (or other electrosurgical device described herein) may be used in conjunction with the hydrosurgical probe. For example, the probe may comprise an electrode such that electrosurgical techniques can be combined with the hydrosurgical fluid jet.

The rapid evaporative ionization mass spectrometry device or probe may be arranged and adapted to vapourise the same portion of tissue that is in contact with the hydrosurgical fluid jet, so as to produce an aerosol that can then be transferred to an ion analyser or mass spectrometer for analysis as described herein.

Methods may involve providing a surgical instrument comprising a hydrosurgical probe as described above, as well as a rapid evaporative ionization mass spectrometry device or probe (e.g., a rapid evaporative ionization mass spectrometry device or probe as described in relation to FIGS. 14A and 14B).

The method may comprise identifying a tissue sample for analysis, using the hydrosurgical device, probe aspirator or dissector to generate an aerosol comprising particles of the tissue sample (or portion of tissue sample), and analysing the particles of the tissue sample contained in the sampling fluid. The analysing may comprise mass analysing and/or ion mobility analysing and/or a combination of mass and ion mobility analysing.

The method may further comprise using the rapid evaporative ionization mass spectrometry device or probe to generate an aerosol comprising particles of the same tissue sample (or portion of tissue sample), and analysing the particles contained in the aerosol. The analysing may comprise mass analysing and/or ion mobility analysing and/or a combination of mass and ion mobility analysing.

The method may comprise outputting one or more mass spectra from each tissue sample, and optionally comparing or combining the mass spectra produced using the rapid evaporative ionization mass spectrometry device or probe with that produced using the hydrosurgical device, probe aspirator or dissector.

The hydrosurgical probe may be arranged and adapted to break up, vapourise or cut a sample, for example biologic tissue. The apparatus may comprise an instrument, for example a surgical instrument, comprising the hydrosurgical probe.

Alternative Energy Sources—Argon Plasma Coagulation

Further embodiments are envisaged in which the electrosurgical tools disclosed herein, for example the rapid evaporative ionisation mass spectrometry device or probe, may be replaced or combined with argon plasma coagulation ("APC") technology.

According to an embodiment there is provided a surgical instrument comprising an argon plasma coagulation ("APC") device. Instead of e.g. water or a saline solution, a jet of argon gas may be directed or pumped through the supply tube 9 and may be sprayed out of the nozzle. Gases other than argon may be used. For example, the jet of argon may instead be a jet of non-flammable gas.

The tip may be modified, and may comprise an electrode arranged and adapted to apply a high voltage spark or discharge (e.g., above about 1 kV, 1.5 kV, 2 kV, 2.5 kV, 3 kV, 4 kV or 5 kV) to the argon gas, for example adjacent to or at the nozzle. The high-voltage spark or discharge may ionise the argon gas as it is sprayed from the nozzle. The voltage spark or discharge may be applied by an electrode (e.g., a tungsten wire) connected to a power supply (e.g., forming part of an analytical stack 1330 as described above in relation to FIG. 13A).

Once the argon gas is ionised, then it may then seek a ground, and this may be found in tissue located adjacent the end of the device. Thermal energy may be delivered with a depth of penetration of, typically, about 2 to 3 mm. The probe may be placed apart from the tissue to be aspirated or disrupted. As discussed above, the argon gas may be emitted and then ionized by the high voltage discharge. The electric current may then be conducted through the jet of gas, resulting in coagulation of the tissue located at the other end of the jet. As the device may not make physical contact with the tissue, the procedure may be seen as relatively safe and can be used to treat delicate tissue having low intracellular bonds, such as skin or fat. The depth of coagulation is typically only a few millimetres.

The argon plasma coagulation device may comprise a gas source and a nozzle for directing a gas (e.g., from said gas source) at high pressure (e.g., greater than 6, 7, 8, 9 or 10 kiloPascals) at a target, for example a sample such as a biologic sample. The surgical instrument may form part of a surgical stack 1301 as described above in relation to FIG. 13A. The surgical instrument may comprise an endoscope or laparoscope. The argon plasma coagulation device may be passed through a port or instrument channel of an endoscope or laparoscope, for example.

The argon plasma coagulation device may be configured to aspirate or fragment biologic tissue and form an aerosol comprising particles of the biologic tissue. The argon plasma coagulation device may further comprise a tube or other means for transferring the particles to a mass analyser and/or ion mobility analyser and/or mass spectrometer.

According to an embodiment there is provided a method of surgery, comprising using a argon plasma coagulation device, probe, aspirator or dissector, for example in an intraoperative diagnosis. The method may comprise identifying tissue for analysis, using the argon plasma coagulation device, probe, aspirator or dissector to generate an aerosol comprising particles of the identified tissue, and analysing the particles. The analysing may comprise mass analysing and/or ion mobility analysing and/or a combination of mass and ion mobility analysing.

The method may comprise identifying a plurality of tissue samples for analysis, using the argon plasma coagulation device, probe, aspirator or dissector to generate a sampling fluid comprising particles of each identified tissue sample, and analysing the particles of each identified tissue sample. The analysing may comprise mass analysing and/or ion mobility analysing and/or a combination of mass and ion mobility analysing.

The particles of each identified tissue sample may be mass analysed and/or ion mobility analysed separately. The method may comprise outputting one or more mass spectra from each tissue sample, and optionally comparing the mass spectra from each tissue sample and optionally identifying differences between the different tissue samples.

The method may comprise using the argon plasma coagulation device, probe, aspirator or dissector to search for a particular compound or compounds in the tissue, and may comprise searching or identifying the compound or compounds in mass spectra produced from the tissue or tissue samples.

Each tissue sample may be taken from the same part of the body or the same organ. Alternatively, each tissue sample may be taken from a different part of the body or a different organ.

The argon plasma coagulation device, probe, aspirator or dissector may be optimised for surgical use. For example, the argon plasma coagulation device, probe, aspirator or dissector may be miniaturised and/or one or more of the largest dimension, length, width and depth of the argon plasma coagulation device, probe, aspirator or dissector may be less than 5 cm, 2 cm, 1 cm or 5 mm. The argon plasma coagulation device, probe, aspirator or dissector may be shaped such that it can be surgically inserted into a human or animal body. For example, the argon plasma coagulation device, probe, aspirator or dissector may be elongated, or form part of an elongated tube or tubing, and/or form part of a surgical instrument such as an endoscope or laparoscope.

The argon plasma coagulation device may comprise the structural features described above in relation to the hydrosurgical device.

As discussed above, the aperture or nozzle may have an output end or exit hole having a diameter or largest dimension in the range of about 0.05 mm to about 1 mm, 0.06 mm to about 0.8 mm, 0.07 to about 0.7 mm, about 0.08 to about 0.6 mm, about 0.09 to about 0.5 mm, about 0.1 mm to about 0.4 mm, about 0.1 mm to about 0.3 mm, about 0.1 mm to about 0.2 mm, about 0.1 mm to about 0.15 mm.

The aperture or nozzle may have an output end or exit hole having a cross-sectional area of about 50 mm$^2$ to about 150 mm$^2$, 60 mm$^2$ to about 140 mm$^2$, 70 mm$^2$ to about 130 mm$^2$, 80 mm$^2$ to about 120 mm$^2$, 90 mm$^2$ to about 110 mm$^2$, and 95 mm$^2$ to about 105 mm$^2$.

The gas jet may be directed away from the probe as indicated at arrow. This can direct the gas or plasma at tissue that is in close proximity to the probe, which in turn can aspirate, dissect, fragment or otherwise disrupt such tissue. Embodiments are contemplated wherein the gas or plasma is directed across tissue, such as parallel to the tissue. The nozzle could be located at a point along the arm a distance from the tip, and be arranged and adapted to direct a stream of gas or plasma from the outlet end or exit hole substantially parallel to the arm.

The flow rate of the gas and/or voltage of the high voltage spark or discharge can be varied to suit different tissue and/or surgical techniques. For example, a relatively low energy flow rate and/or voltage can be applied to dissect or fragment tissue having low intracellular bonds, such as skin or fat, and relatively high energy flow rate and/or voltage can be used to dissect or fragment tissue having high intracellular bonds, such as bone or tendon.

One or more holes may be located at the tip, so as to transfer tissue particles aspirated by the argon plasma coagulation device to an ion analyser or mass spectrometer 8 via an internal passage and tubing 6 (see also FIG. 1). The one or more holes may, alternatively or additionally, be located anywhere on the probe, and may be arranged and adapted to transfer particles as described above. For example, the one or more holes may be located along the arm and/or outside of the tip.

The tip may have a surface area less than 2 mm$^2$, 1 mm$^2$, 0.5 mm$^2$, 0.4 mm$^2$, 0.3 mm$^2$, 0.2 mm$^2$ or 0.1 mm$^2$.

A lower voltage or gas flow can assist in minimally-invasive or non-invasive surgery.

The surgical instrument may comprise a pump arranged and adapted to supply and/or pump the gas. A tubing 9 may be provided in order to supply the gas to the surgical instrument. The pump may be located within the probe, or may be located external to the probe and connected thereto via the tubing 9.

The pump may be arranged and adapted to apply a varying flow rate and/or pressure of the gas to the nozzle, and the varying flow rate and/or pressure may be used to vary the applied energy of the fluid.

The pump and/or nozzle may be arranged and adapted to output gas from the nozzle at a pressure greater than about 0.01 MPa, for example between about 0.01 to about 1.5 MPa, about 0.05 to about 1.4 MPa, about 0.1 to about 1.3 MPa, about 0.8 to about 1.2 MPa, about 0.9 to about 1.1 MPa, or about 0.95 to about 1.05 MPa.

The probe may be operatively connected to an ion analyser or mass spectrometer, for example an ion analyser or mass spectrometer forming part of an analytical stack 1330 as described above in relation to FIG. 13A. The probe may be connected to the ion analyser or mass spectrometer via a tissue sampling device or tubing, for example the tissue sampling device 1336 as described above in relation to FIG. 13A, or the tubing 6 shown in FIG. 1.

The tissue sampling device or tubing, or other connecting means connecting the probe to the ion analyser or mass spectrometer, for example a first vacuum stage thereof, may have a maximum diameter of less than 1 mm, 0.9 mm, 0.8 mm, 0.7 mm, 0.6 mm, 0.5 mm, 0.4 mm, 0.3 mm, 250 μm, 200 μm, 150 μm, 100 μm, 50 μm, 40 μm, 30 μm, 20 μm or 10 μm. A small diameter tubing can assist in transferring the sampling fluid generated by the probe to the ion analyser or mass spectrometer quickly. The tissue sampling device or tubing may connect the probe to an ion inlet device, or first vacuum stage of the ion analyser or mass spectrometer.

The argon plasma coagulation device may be used to fragment or otherwise disrupt tissue coming into contact with the fluid. This may produce an aerosol or particles of tissue that can then be transferred to an ion analyser or mass spectrometer, for example via tubing 6.

Embodiments are envisaged wherein the hydrosurgical probe forms part of a laparoscope or endoscope. In such a situation, the arm of the probe may be located within the laparoscope or endoscope and may be longer. The nozzle may be located at the distal end of the laparoscope or endoscope and may be arranged and adapted to fragment or otherwise disrupt tissue located adjacent to the distal end of the laparoscope or endoscope.

In various embodiments, a rapid evaporative ionization mass spectrometry device or probe (or other electrosurgical device described herein) may be used in conjunction with the argon plasma coagulation device. For example, the probe 1700 may comprise a further electrode arranged and adapted to contact tissue adjacent to the argon plasma coagulation device, such that electrosurgical techniques can be combined with the hydrosurgical fluid jet.

The rapid evaporative ionization mass spectrometry device or probe may be arranged and adapted to vapourise the same portion of tissue that is located adjacent to the argon plasma coagulation device, so as to produce an aerosol (or more aerosol) that can then be transferred to an ion analyser or mass spectrometer for analysis as described herein.

Methods may involve providing a surgical instrument comprising a argon plasma coagulation device as described above, as well as a rapid evaporative ionization mass spectrometry device or probe (e.g., a rapid evaporative ionization mass spectrometry device or probe as described in relation to FIGS. 14A and 14B).

The method may comprise identifying a tissue sample for analysis, using the argon plasma coagulation device, probe aspirator or dissector to generate an aerosol comprising particles of the tissue sample (or portion of tissue sample), and analysing the particles of the tissue sample contained in the sampling fluid. The analysing may comprise mass analysing and/or ion mobility analysing and/or a combination of mass and ion mobility analysing.

The method may further comprise using the rapid evaporative ionization mass spectrometry device or probe to generate an aerosol comprising particles of the same tissue sample (or portion of tissue sample), and analysing the particles contained in the aerosol. The analysing may comprise mass analysing and/or ion mobility analysing and/or a combination of mass and ion mobility analysing.

The method may comprise outputting one or more mass spectra from each tissue sample, and optionally comparing or combining the mass spectra produced using the rapid evaporative ionization mass spectrometry device or probe with that produced using the argon plasma coagulation device, probe aspirator or dissector.

The argon plasma coagulation device may be arranged and adapted to break up, vapourise or cut a sample, for example biologic tissue. The apparatus may comprise an instrument, for example a surgical instrument, comprising the argon plasma coagulation device.

Dermatology

According to an embodiment there is provided a method of treating a biologic sample, comprising identifying a portion of the sample to be analysed, vapourising or otherwise creating an aerosol from the sample portion, analysing the aerosol, and determining whether any compounds of interest are contained in the aerosol. The analysing may comprise mass analysing and/or ion mobility analysing and/or a combination of mass and ion mobility analysing.

The biologic sample and/or the sample portion may comprise skin. Any of the methods for vapourising or creating an aerosol from a biologic sample disclosed herein may be used. For example, a laser or ultrasound probe may be used as discussed above. The method of treating a biologic sample may include any of the methods disclosed herein to the extent that they are compatible.

A surgical instrument may be used to carry out part of the method, and the surgical instrument may comprise an electrosurgical tool, for example a rapid evaporative ionization mass spectrometry device or probe, an ion analyser or mass spectrometer and a control system.

The disclosure extends to an apparatus arranged and adapted to perform the methods disclosed herein, and the apparatus may comprise a control system arranged and adapted to carry out any method steps.

The surgical instrument may form part of an analytical stack 1301 and/or apparatus 1300 as described above in relation to FIG. 13A, for example comprising a camera monitor 1303 and/or an analysis monitor 1333 (which may also be the same component).

The electrosurgical tool or rapid evaporative ionization mass spectrometry probe may be a rapid evaporative ionization mass spectrometry probe as described herein with reference to FIG. 14, or a bipolar forceps probe as described herein with reference to FIG. 1.

Non-invasive or minimally-invasive methods may be used that do not penetrate deep into the tissue.

For example, the step of vapourising or otherwise creating an aerosol from the sample portion may include not penetrating more than (and/or penetrating less than) 1 μm, 2 μm, 3 μm, 4 μm, 5 μm, 10 μm, 20 μm, 25 μm, 30 μm, 35 μm, 50 μm, 100 μm, 200 μm or 250 μm into the sample.

The method may further comprise making dermatological decisions based on the compounds. For example, if compounds of interest are located within the sample portion then the method may comprise the step of removing said sample portion, or removing part of the sample portion.

The method may then comprise checking to see if the compounds of interest are still present (by vapourising or otherwise creating an aerosol from the sample portion and analysing the aerosol) and removing additional matter if this is the case. The analysing may comprise mass analysing and/or ion mobility analysing and/or a combination of mass and ion mobility analysing.

If compounds of interest are no longer present the method may comprise ceasing, or immediately ceasing to remove matter from the sample portion.

If compounds of interest are not located in the sample portion then the method may comprise the step of moving to a different portion of the sample and carrying out the method again.

For example, cancerous tissue could be located on a portion of skin, and the cancerous tissue then fragmented or otherwise removed using a suitable probe (e.g., a laser probe).

The aerosol generated during this process could be aspirated through the tissue sample device or tubing and can be used as a guide to stop the removal of tissue once the cancerous tissue has been removed.

Electrosurgical Tips/Coatings

According to an embodiment there is provided an electrosurgical tool or probe, for example comprising a rapid evaporative ionization mass spectrometry probe. The electrosurgical tool or probe may be arranged and adapted to apply an electric current to a sample (e.g., biologic tissue) to cut, coagulate, desiccate or fulgurate the sample or a portion of the sample. The tool or probe may be arranged and adapted to capture particles from the portion of the sample that has been vapourised by the electrosurgical tool. An apparatus may comprise the electrosurgical tool and a mass analyser and/or ion mobility analyser and/or mass spectrometer, and the mass analyser and/or ion mobility analyser and/or mass spectrometer may be arranged and adapted to mass analyse and/or ion mobility analyse the vapourised particles.

The electrosurgical tool may comprise an electrode arranged and adapted to evaporate or vapourise the sample. The electrosurgical tool may further comprise a counter or return electrode arranged and adapted to contact the sample. The counter or return electrode may be grounded.

Any of the embodiments disclosed herein that involve an electrosurgical tool may operate in this manner, and the electrosurgical tool disclosed in those embodiments may be arranged and adapted in the manner described above.

Rapid Evaporative Ionization Mass Spectrometry Technology Consumables

Referring back to FIG. 1, this shows an apparatus comprising an electrosurgical tool 1 (e.g., bipolar forceps) that may be connected to an ion analyser or mass spectrometer 8 via a tube 6. The electrosurgical tool 1 may be connected to a power supply 4 via a wire 9. As discussed herein, the tool may comprise one or more electrodes or other means (e.g., laser or ultrasound), which electrodes or other means may be configured to evaporate, vapourise or fragment biologic tissue 3 to form an aerosol.

Figure 18:
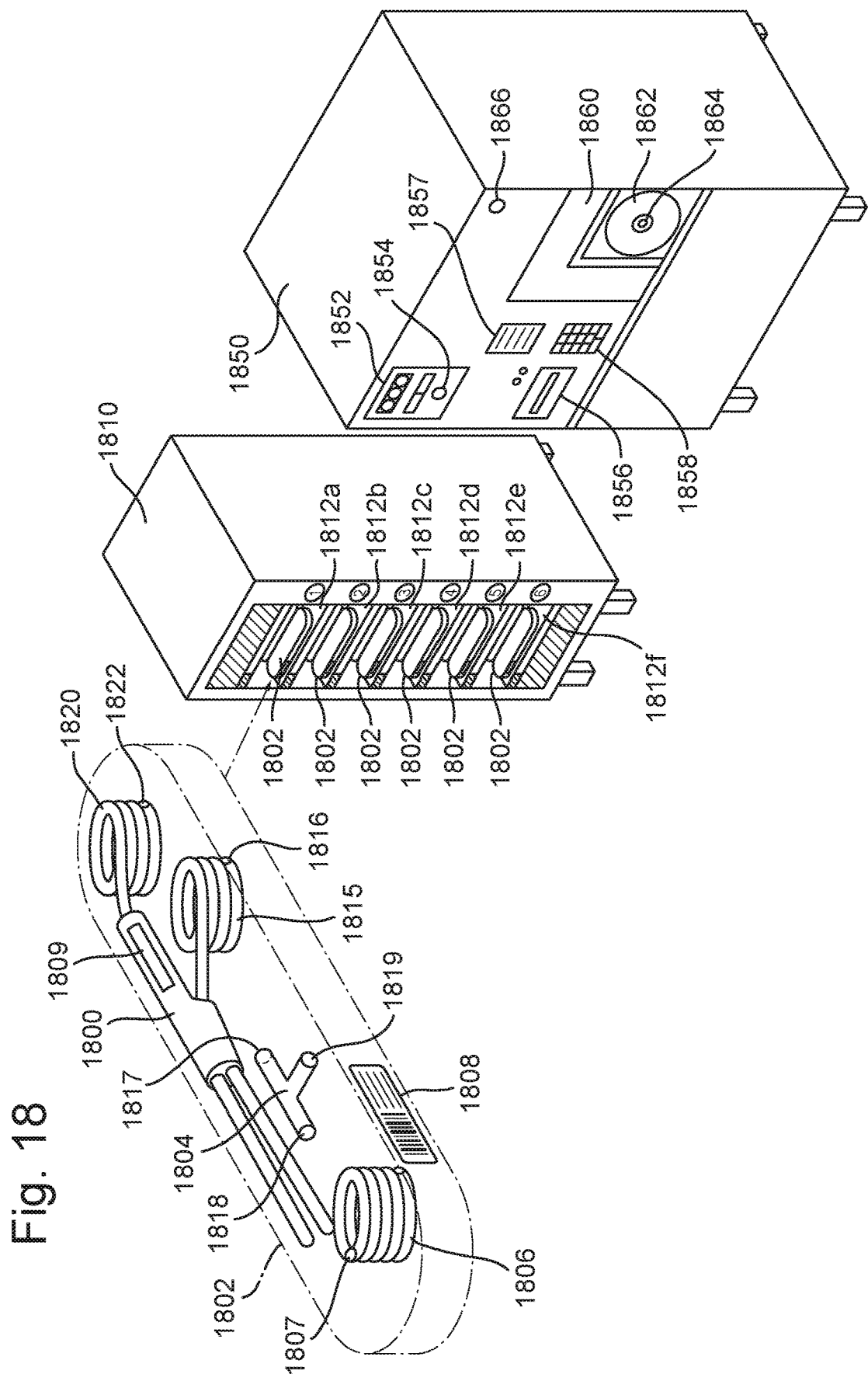
FIG. 18 shows an apparatus that may be used in an operating theatre to control the use and distribution of the surgical tools disclosed herein.

Now referring to FIG. 18, a surgical tool 1800 is shown in a packaged configuration. The surgical tool 1800 may be an electrosurgical tool, for example a rapid evaporative ionization mass spectrometry probe as described herein with reference to FIGS. 14A-B, a bipolar forceps probe as described herein with reference to FIG. 1, or the surgical tool 1800 may be an ultrasound probe 1600 as described herein with reference to FIG. 16, or a laser probe 1700 as described herein with reference to FIG. 17.

The surgical tool 1800 may be packaged within a pouch or packet 1802, which may be transparent or translucent. The package may further contain supplementary items, such as a mixing device 1804 and/or further tubing 1806. Alternatively, the supplementary items may be contained within a separate packet.

The packet 1802 may be one of a plurality of packets 1802 that may be contained within a packet holder 1810. The packet holder 1810 may comprise a number of compartments 1812*a-f* arranged and adapted to house or contain packets containing surgical tools or other equipment for use in relation to such tools, such as the packet 1802. Each compartment 1812*a-f* of the packet holder 1810 may comprise a different type of surgical tool or other equipment, which may relate to a different surgical procedure.

For example, compartment 1812*b* may hold a plurality of packets 1802 that each contain bipolar forceps as shown with reference to FIGS. 1 and 14A, and a different compartment (e.g., 1812*a*) may hold a plurality of packets 1802 that each contain monopolar forceps as shown with reference to FIG. 14B.

An identification device 1808,1809 (e.g., a barcode) may be provided on the packet 1802 and/or the tool 1800. This may contain data or information relating to the type of tool or equipment that is in the packet 1802, or contain a code that can be read by a scanner or reading means (e.g., a barcode reader).

An apparatus 1850 may be provided that houses an analyser 1860, which may comprise an inlet device 1862. The analyser could be an ion analyser or mass spectrometer as described herein, such as the ion analyser or mass spectrometer 8 disclosed with reference to FIG. 1, and the inlet device 1862 may be an ion inlet device. The apparatus 1850 may form part of a surgical and/or analytical stack as disclosed with reference to FIGS. 13A and 13B.

The analyser 1860 may comprise a connector 1864 that may form the entrance to a first vacuum stage of the analyser 1860. The tool 1800 may comprise a corresponding connector 1816 that may be connected to the tool 1800 via tubing 1815. Alternatively, the mixing device 1804 may comprise a connector 1817 configured to connect to the connector 1834 located on the analyser 1860. Alternatively, the further tubing 1806 may comprise a connector 1807 configured to connect to the connector 1834 located on the analyser 1860.

The apparatus 1850 may further comprise a voltage supply 1852 that may be arranged and adapted to supply a voltage to the tool via a socket 1854. A wire 1820 may be provided on the tool 1800 and may comprise a plug 1822 configured to plug into the socket 1854 so as to power the tool 1800. In some embodiments, the voltage supply 1852 may instead be a different energy source, such as a laser source.

The apparatus 1850 may comprise a scanner, reader, detector or other means 1856 arranged and adapted to scan, read or detect the identification device 1808, 1809 located on the packet 1802 and/or the tool 1800. The apparatus may comprise a memory that contains data or a database linking the code or other data contained on the identification device 1808, 1809 to a particular type of surgical procedure.

The memory may contain a statistical model or an identification or other algorithm, and the code or other data contained on the identification device 1808, 1809 may form or comprise part of a parameter or input for the statistical model or algorithm. Other inputs (e.g., type of patient, condition of patient, etc.) could be used in the statistical model or algorithm. The outcome of the model or algorithm may be used to determine operational parameters of the tool 1800, or instrument parameters of the analyser 1860.

The apparatus 1850 may comprise a display 1857 for displaying information, for example regarding the type of device that has just been scanned, or the type of surgical procedure that is about to be performed. The display may be in the form of a mobile device, for example a mobile tablet device.

The apparatus 1850 may comprise a fluid outlet port 1866 that may be in fluid communication with a source of fluid, for example a matrix as discussed herein. A tube may be connected to the fluid outlet port 1866 and the tube may be connectable to a corresponding port 1819 on the mixing device 1804.

An input device 1858 (e.g., a keypad) may be provided on the apparatus 1850 and may be linked to the memory and display 1857 via a processor or other processing means. It is envisaged that a user (e.g., a surgeon or other person) could enter a code into the input device 1858, and the processor or other processing means may be configured to search the memory for this code and find a corresponding "correct" surgical procedure. The correct surgical procedure may then be displayed on the display 1857, together with a list of required equipment. The list of equipment may include the type of surgical tool required.

Upon noting the type of surgical tool required, the user may retrieve the required tool from the packet holder 1810. The display 1857 may show which of the compartments 1812*a-f* the tool is located, for example. Once the packet 1802 is retrieved from the packet holder 1810 the identification device 1808,1809 can then be scanned, read or detected by the scanner, reader or detector 1856. If the correct (or incorrect) tool has been retrieved, then the display 1857 may indicate this.

It is envisaged that a control means for the apparatus 1850 may be arranged and adapted to control activation of the voltage supply 1852 and/or analyser 1860. The control means may be arranged and adapted to activate the voltage supply 1852 and/or analyser 1860 only once the packet 1802 or tool 1800 corresponding to (or associated with) the correct surgical procedure has been scanned, read or detected by the scanner, reader or detector 1856.

This may help to protect against a surgeon using an incorrect tool. In the case of rapid evaporative ionization mass spectrometry devices or probes, this may be important, since the bipolar forceps (see FIG. 14A) can operate quite differently to the monopolar device (FIG. 14B) and it can be important to choose the correct tool, depending on the type of surgery required.

Alternatively, or additionally, the packet holder 1810 may comprise preventative screens or other means configured to prevent access to each of the compartments 1812*a-f* (and the tools within). The screens may be moveable such that in a first position access to the respective compartment is prevented or restricted, and in a second, different position access to the compartment is permissible. Movement of the screen between the first and second positions may be controlled by the control means of the apparatus 1850.

The control means may be arranged and adapted such that access to a particular compartment is permissible (e.g., the screen is moved between first and second positions) only if the code corresponding to that compartment or tool within has been entered into the input device 1858. This may provide an alternative or additional method of preventing the incorrect tool being chosen for a particular surgical procedure.

In order to prevent contamination between tools, the package 1802 and its contents may be replaceable and/or disposable.

According to an embodiment, there is provided a kit comprising the apparatus 1850, packet holder 1810 and a plurality of packets 1802. Within each of the plurality of packets may be a surgical tool (e.g., bipolar forceps 1800) and optionally one or more supplementary items (e.g., 1804,1806).

The items and tools in the packets may correspond to any of the tools, devices, probes and related equipment disclosed herein.

For example, and referring to FIG. 1, the surgical tool may be the bipolar forceps 1, and the tubing 1815 may be the inlet tube 6. The bipolar forceps 1 and the inlet tube 6 may be replaceable and/or disposable. The bipolar forceps 1 and the inlet tube 6 may be made from plastic, polyethylene, polycarbonate, polyvinyl chloride ("PVC") or polytetrafluoroethylene ("PTFE").

Referring to the embodiment of FIGS. 2A-2C, the surgical tool may be a device or probe, for example a rapid evaporative ionization mass spectrometry device or probe as disclosed with reference to FIGS. 14A and 14B, and the supplementary items may include the tube 21, the sample transfer tube 15 and the whistle 12. The surgical tool 1800, tube 21, the sample transfer tube 15 and the whistle 12 may be replaceable and/or disposable.

Any one of the surgical tool 1800, tube 21, the sample transfer tube 15 and the whistle 12 may be made from plastic, polyethylene, polycarbonate, polyvinyl chloride ("PVC") or polytetrafluoroethylene ("PTFE"). Having these components replaceable can mean that all of the components before the matrix (see matrix introduction conduit 30 in FIG. 2A) are replaceable and/or disposable.

Referring to the embodiment of FIGS. 4A and 4B, the surgical tool may be a device or probe, for example a rapid evaporative ionization mass spectrometry device or probe as disclosed with reference to FIGS. 14A and 14B, and the supplementary items may include the T-piece 100 and sample transfer tube 120 (which may be the same component as the tubing 1815/inlet tube 6). The matrix introduction conduit 130 may be included in the supplementary items for convenience, but as this does not come into contact with the flow of aerosol particles 122, it may be less susceptible to contamination.

In some embodiments, as described above, the inlet tube 140 (FIGS. 4A and 4B) may be removable from the ion analyser or mass spectrometer, and this may be included in the supplementary items as well. Any one of the surgical tool 1800, T-piece 100, matrix introduction conduit 130, inlet tube 140 and sample transfer tube 120 may be replaceable and/or disposable. Any one of the surgical tool 1800, T-piece 100, matrix introduction conduit 130, inlet tube 140 and sample transfer tube 120 may be made from plastic, polyethylene, polycarbonate, polyvinyl chloride ("PVC") or polytetrafluoroethylene ("PTFE").

Referring to the embodiment of FIG. 5A, the surgical tool may be a device or probe, for example a rapid evaporative ionization mass spectrometry device or probe as disclosed with reference to FIGS. 14A and 14B, and the supplementary items may include the inlet tube 152 (which may be the same component as the tubing 1815/inlet tube 6). The sample transfer portion 156 may be included in the supplementary items for convenience.

Any one of the device or probe, inlet tube 152 and sample transfer portion 156 may be replaceable and/or disposable. Any one of the device or probe, inlet tube 152 and sample transfer portion 156 may be made from plastic, polyethylene, polycarbonate, polyvinyl chloride ("PVC") or polytetrafluoroethylene ("PTFE").

Referring to the embodiment of FIG. 5B, the surgical tool may be a device or probe, for example a rapid evaporative ionization mass spectrometry device or probe as disclosed with reference to FIGS. 14A and 14B, and the supplementary items may include the inlet tube 202 (which may be the same component as the tubing 1815/inlet tube 6). Any of the sample transfer portion 220, matrix introduction conduit 230 and inlet tube 240 may be included in the supplementary items for convenience.

Any one of the device or probe, inlet tube 202, sample transfer portion 220, matrix introduction conduit 230 and inlet tube 240 may be replaceable and/or disposable. Any one of the device or probe, inlet tube 202, sample transfer portion 220, matrix introduction conduit 230 and inlet tube 240 may be made from plastic, polyethylene, polycarbonate, polyvinyl chloride ("PVC") or polytetrafluoroethylene ("PTFE").

Referring to the embodiment of FIG. 11, the surgical tool may be the Desorption Electrospray Ionisation ("DESI") sprayer 300, for example the solvent capillary 302 and sheath gas tube 312 thereof (wherein the remaining components may not be part of the items contained in the packet) and/or the transfer or inlet capillary 330, and the supplementary items may include the sample surface 310.

Any one of the Desorption Electrospray Ionisation ("DESI") sprayer 300, solvent capillary 302 and sheath gas tube 312 and/or the transfer or inlet capillary 330 may be replaceable and/or disposable. Any one of the Desorption Electrospray Ionisation ("DESI") sprayer 300, solvent capillary 302 and sheath gas tube 312 and/or the transfer or inlet capillary 330 may be made from plastic, polyethylene, polycarbonate, polyvinyl chloride ("PVC") or polytetrafluoroethylene ("PTFE").

Referring to the embodiment of FIGS. 13A-13C, the surgical tool may comprise the ion sampling device 1336 and/or endoscope (or laparoscope) 1310. The ion analyser or mass spectrometer 1332 of FIG. 13A may be the same component as the analyser 1850 of FIG. 18. The ion inlet device 1334 of FIG. 13A may be the same component as the inlet device 1862 of FIG. 18.

Any one of the ion sampling device 1336 and/or endoscope (or laparoscope) 1310 may be replaceable and/or disposable. Any one of the ion sampling device 1336 and/or endoscope (or laparoscope) 1310 may be made from plastic, polyethylene, polycarbonate, polyvinyl chloride ("PVC") or polytetrafluoroethylene ("PTFE").

The surgical tool may comprise (or be) one of the electrosurgical probes 1400, 1450 disclosed with reference to FIGS. 14A and 14B. In such a case the tubing 1815 may correspond to the inlet tube 6 and this may be included as part of the surgical tool or as a supplementary item (e.g., unattached to the probe). The wire 9 may be included as a supplementary item, or may simply be attached to the voltage supply 1852 separately.

Any one of the electrosurgical probes 1400, inlet tube 6 or wire 9 may be replaceable and/or disposable.

The surgical tool may comprise (or be) one of the ultrasound or laser probes 1600, 1700, disclosed with reference to FIGS. 16 and 17 respectively. In such a case the tubing 1815 may correspond to the inlet tube 6 and this may be included as part of the surgical tool or as a supplementary item (e.g., unattached to the probe). The wire 9 may be included as a supplementary item, or may simply be attached to the voltage supply 1852 separately.

Any one of the ultrasound or laser probes 1600, inlet tube 6 or wire 9 may be replaceable and/or disposable.

The surgical tool may comprise (or be) one of the hydrosurgical or argon plasma coagulation ("APC") devices. In such a case the tubing 1815 may correspond to the inlet tube 6 and this may be included as part of the surgical tool or as a supplementary item (e.g., unattached to the probe). The wire 9 may be included as a supplementary item, or may simply be attached to the voltage supply 1852 separately.

Any one of the hydrosurgical or argon plasma coagulation ("APC") devices, inlet tube 6 or wire 9 may be replaceable and/or disposable.

According to an embodiment there is provided a replaceable and/or disposable rapid evaporative ionization mass spectrometry ("REIMS") device or probe comprising one or more electrodes arranged and adapted to evaporate or vapourise biologic tissue to form an aerosol, and transfer means for transferring the aerosol into a mass spectrometer, for example a first vacuum stage thereof.

The transfer means may comprise one or more tubes, which may be made of plastic, polyethylene, polycarbonate, polyvinyl chloride ("PVC") or polytetrafluoroethylene ("PTFE").

According to an embodiment there is provided an apparatus comprising a mass spectrometer and the replaceable and/or disposable rapid evaporative ionization mass spectrometry ("REIMS") device or probe. The mass spectrometer may comprise a fixed or non-disposable connecting portion, which may be configured to mate with a connecting portion located on said replaceable and/or disposable rapid evaporative ionization mass spectrometry ("REIMS") device or probe.

The fixed or non-disposable connecting portion may be located at the entrance to a first vacuum chamber of the mass spectrometer.

The apparatus may comprise a conduit arranged and adapted to introduce a matrix or solvent to the flow of aerosol into the mass spectrometer. The fixed or non-disposable connecting portion may be located at the point at which the matrix or solvent mixes with the flow of aerosol.

Identification Devices (e.g., Radio Frequency Identification ("RFID") Tags)

According to various embodiments the surgical tool 1800 (and/or packet 1802) described with reference to FIG. 18 may be provided which includes an identification device 1808, 1809. The identification device 1808,1809 may comprise an RFID tag.

A controller or the control system may interrogate or scan the RFID tag in order to identify or ascertain the intended use of the surgical tool 1800 (e.g., a rapid evaporative ionization mass spectrometry device or probe).

For example, the surgical tool 1800 may be intended to be used only for a specific surgical procedure and/or regulatory approval may have only been obtained for a specific surgical procedure. In such circumstances, the controller or control system may set various operational parameters in response to interrogating or scanning the identification device 1808, 1809 (e.g., RFID tag).

For example, it may be desired that the surgical tool 1800 can only be used for safety reasons to perform a single surgical procedure in which case the controller or control system may block or otherwise prevent second and subsequent attempted uses of the surgical tool 1800. In various embodiments, the memory may comprise data relating to the number of surgical procedures that are permitted for a particular type of surgical tool 1800. The control system may be arranged and adapted to control the voltage supply 1852 (or other energy source), for example, such that only the permitted number of surgical procedures can be carried out using a given surgical tool 1800. Before each surgical procedure, the surgeon (or other user) may scan the identification device 1808,1809 for a given surgical tool 1800, and the control system may be arranged and adapted to switch on the voltage supply 1852 (or other energy source) only if the surgical tool 1800 has been used for a number of surgical procedures equal to or less than the permitted number stored in memory.

The surgical tool 1800 (e.g., rapid evaporative ionization mass spectrometry device or probe) may be intended to be used for a specific surgical procedure e.g. resecting cancerous lung tissue as described in relation to FIGS. 13A and 13B. In these circumstances the controller or control system may be arranged and adapted to load a specific database and display such data on the display 1857 (or another type of display, such as monitors 1303 and 1333 described in relation to FIGS. 13A and 13B). The data may include, for example, identification data relating to normal and cancerous lung tissue, to help the surgeon in distinguishing between these types of tissue.

Furthermore, according to various embodiments subsequent multi-dimensional analysis of mass spectral data by, for example, PCA analysis may be customized according to the intended use of the surgical tool 1800, as dictated by the identification device.

Embodiments are also contemplated wherein in an emergency situation restrictions imposed by the identification device and the controller or control device may be overridden. For example, in a medical emergency or battlefield situation restrictions which would normally otherwise be imposed upon the intended use of the surgical tool 1800 may be overridden. According to an embodiment an override code may be obtained which may unlock certain restrictions which would otherwise be imposed upon the intended use of the surgical tool 1800.

Analysing Sample Spectra

A list of analysis techniques which are intended to fall within the scope of the present invention are given in the following table:

| Analysis Techniques |
|---|
| Univariate Analysis |
| Multivariate Analysis |
| Principal Component Analysis (PCA) |
| Linear Discriminant Analysis (LDA) |
| Maximum Margin Criteria (MMC) |
| Library Based Analysis |
| Soft Independent Modelling Of Class Analogy (SIMCA) |
| Factor Analysis (FA) |
| Recursive Partitioning (Decision Trees) |
| Random Forests |
| Independent Component Analysis (ICA) |
| Partial Least Squares Discriminant Analysis (PLS-DA) |
| Orthogonal (Partial Least Squares) Projections To Latent Structures (OPLS) |
| OPLS Discriminant Analysis (OPLS-DA) |
| Support Vector Machines (SVM) |
| (Artificial) Neural Networks |
| Multilayer Perceptron |
| Radial Basis Function (RBF) Networks |
| Bayesian Analysis |
| Cluster Analysis |
| Kernelized Methods |
| Subspace Discriminant Analysis |
| K-Nearest Neighbours (KNN) |
| Quadratic Discriminant Analysis (QDA) |
| Probabilistic Principal Component Analysis (PPCA) |
| Non negative matirix factorisation |
| K-means factorisation |
| Fuzzy c-means factorisation |
| Discriminant Analysis (DA) |

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 19:
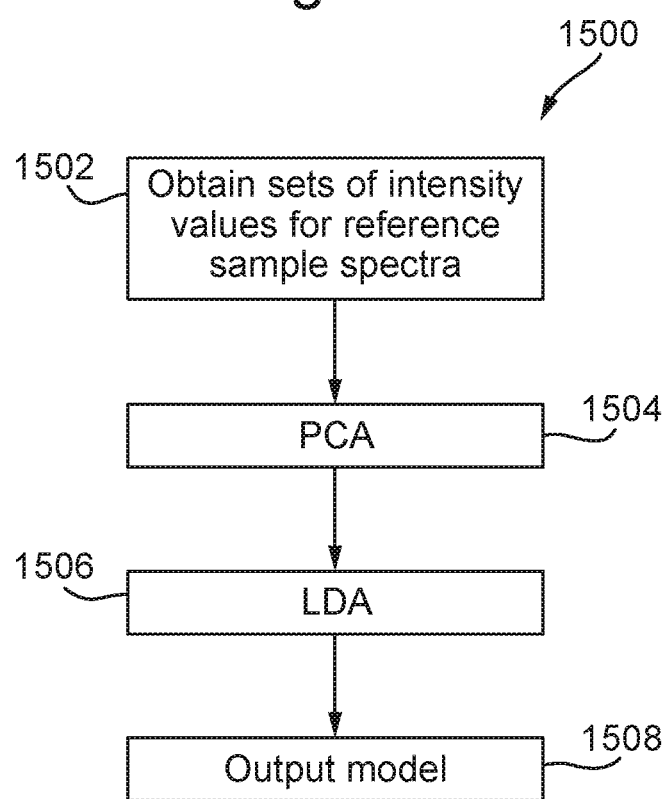
FIG. 19 shows a method of analysis that comprises building a classification model according to various embodiments.

FIG. 19 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 20:
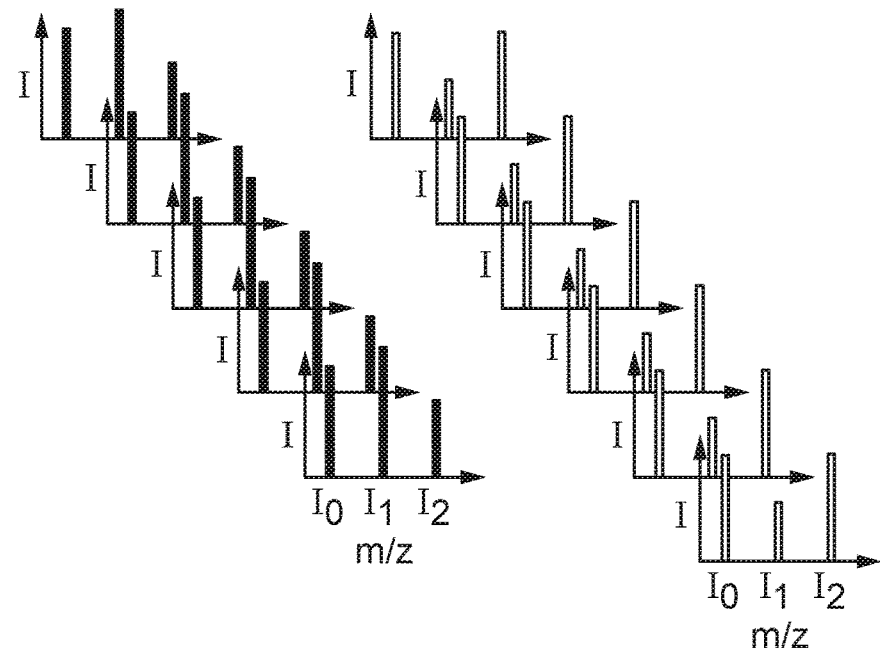
FIG. 20 shows a set of reference sample spectra obtained from two classes of known reference samples.

FIG. 20 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 21:
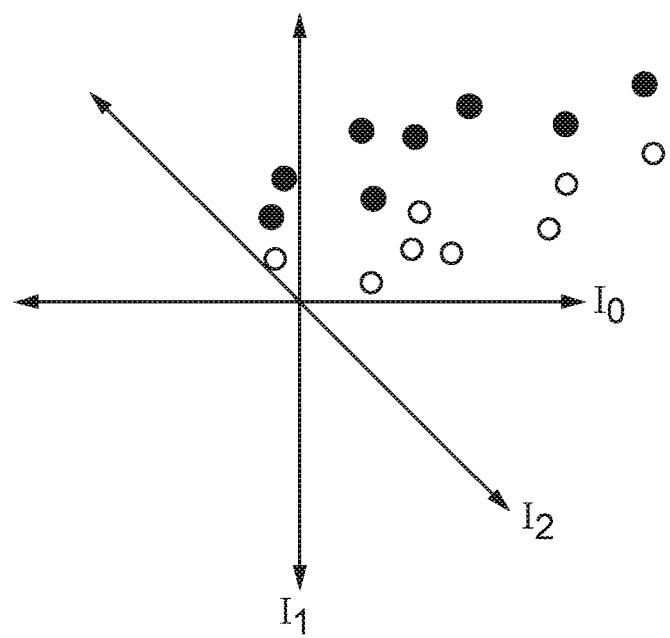
FIG. 21 shows a multivariate space having three dimensions defined by intensity axes, wherein the multivariate space comprises plural reference points, each reference point corresponding to a set of three peak intensity values derived from a reference sample spectrum.

FIG. 21 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 22:
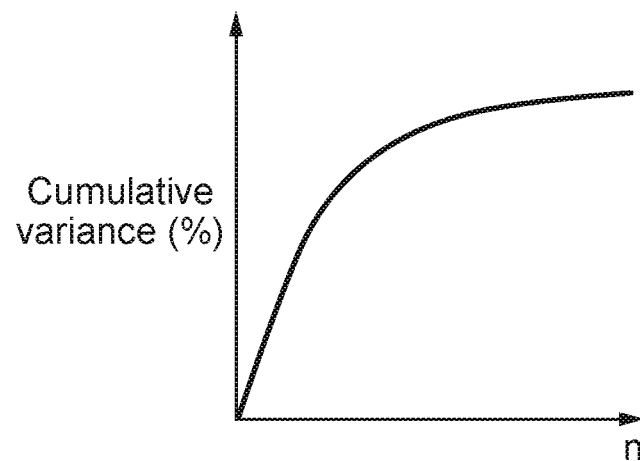
FIG. 22 shows a general relationship between cumulative variance and number of components of a PCA model.

FIG. 22 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \tag{1}$$

Figure 23:
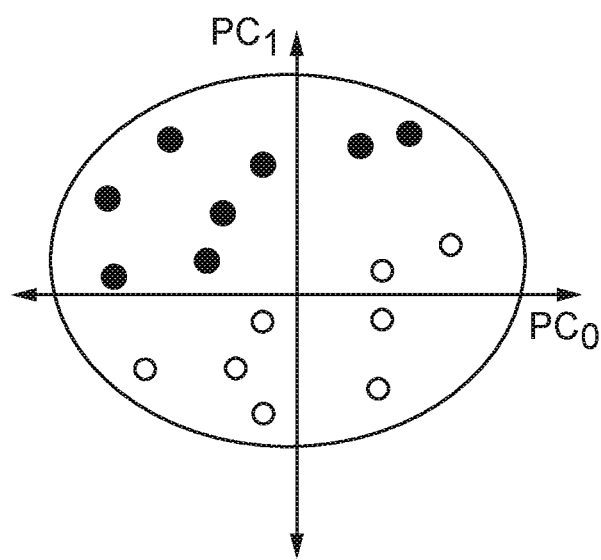
FIG. 23 shows a PCA space having two dimensions defined by principal component axes, wherein the PCA space comprises plural transformed reference points or scores, each transformed reference point or score corresponding to a reference point of FIG. 21.

FIG. 23 shows the resultant PCA space for the reference sample spectra of FIGS. 20 and 21. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 20 and therefore to a reference point of FIG. 21.

As is shown in FIG. 23, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \tag{2}$$

where the matrix Z contains the scores transformed into the LDA space.

Figure 24:
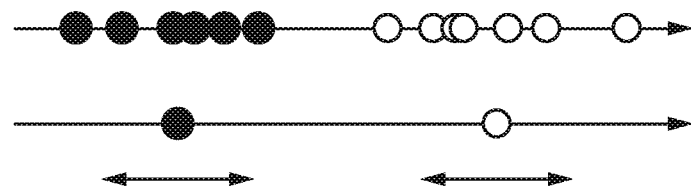
FIG. 24 shows a PCA-LDA space having a single dimension or axis, wherein the LDA is performed based on the PCA space of FIG. 23, the PCA-LDA space comprising plural further transformed reference points or class scores, each further transformed reference point or class score corresponding to a transformed reference point or score of FIG. 23.

FIG. 24 shows a PCA-LDA space having a single dimension or axis, wherein the LDA is performed in the PCA space of FIG. 23. As is shown in FIG. 24, the LDA space comprises plural further transformed reference points or PCA-LDA scores, with each further transformed reference point corresponding to a transformed reference point or PCA score of FIG. 23.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \tag{3}$$

where $V_g$ are the class covariance matrices in the PCA space.

The transformed class average position $z_g$ for class g may be given by $$s_g U = z_g \tag{4}$$

where $s_g$ is the class average position in the PCA space.

Multivariate Analysis—Using a Model for Classification

By way of example, a method of using a classification model to classify an aerosol, smoke or vapour sample will now be described.

Figure 25:
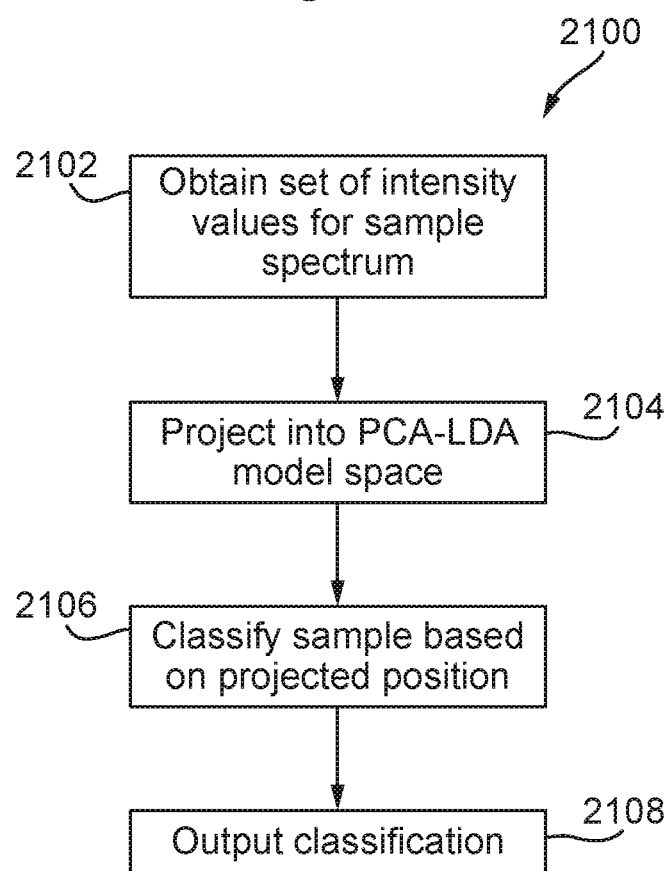
FIG. 25 shows a method of analysis that comprises using a classification model according to various embodiments.

FIG. 25 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 26:
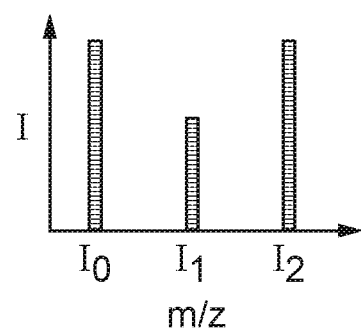
FIG. 26 shows a sample spectrum obtained from an unknown sample.

FIG. 26 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (5)$$

Then, a transformed PCA-LDA vector $z_x$ for the sample spectrum can be obtained as follows:

$$s_x U = z_x \quad (6)$$

Figure 27:
FIG. 27 shows the PCA-LDA space of FIG. 24, wherein the PCA-LDA space further comprises a PCA-LDA projected sample point derived from the peak intensity values of the sample spectrum of FIG. 26.

FIG. 27 again shows the PCA-LDA space of FIG. 24. However, the PCA-LDA space of FIG. 27 further comprises the projected sample point, corresponding to the transformed PCA-LDA vector $z_x$, derived from the peak intensity values of the sample spectrum of FIG. 26.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \quad (8)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

Figure 28:
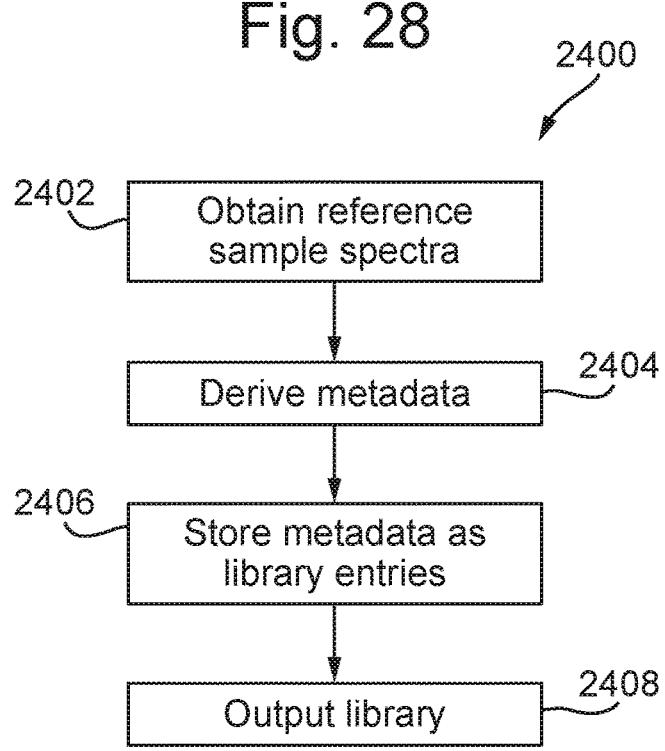
FIG. 28 shows a method of analysis that comprises building a classification library according to various embodiments.

FIG. 28 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} \Big/ \log \frac{M_{max}}{M_{min}} \right\rfloor$$

where $N_{chan}$ is a selected value and denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i \mid \mu_i D_i) = \frac{1}{D_i} \frac{C^{C-1/2} \Gamma(C)}{\sqrt{\pi} \Gamma(C - 1/2)} \frac{1}{\left(C + \frac{(y_i - \mu_i)^2}{D_i^2}\right)^C}$$

where $1/2 < C < \infty$ and where $\Gamma(C)$ is the gamma function.

The above equation is a generalised Cauchy distribution which reduces to a standard Cauchy distribution for C=1 and becomes a Gaussian (normal) distribution as $C \to \infty$. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i \mid \mu_i D_i) = \frac{3}{4} \frac{1}{D_i} \frac{1}{(3/2 + (y_i - \mu_i)^2 / D_i^2)^{3/2}}$$

For each library entry, the parameters $\mu_i$ are set to the median of the list of values in the i'th channel of the input reference sample spectra while the deviation $D_i$ is taken to be the interquartile range of these values divided by √2. This choice can ensure that the likelihood for the i'th channel has the same interquartile range as the input data, with the use of quantiles providing some protection against outlying data.

Library-Based Analysis—Using a Library for Classification

By way of example, a method of using a classification library to classify an aerosol, smoke or vapour sample will now be described.

Figure 29:
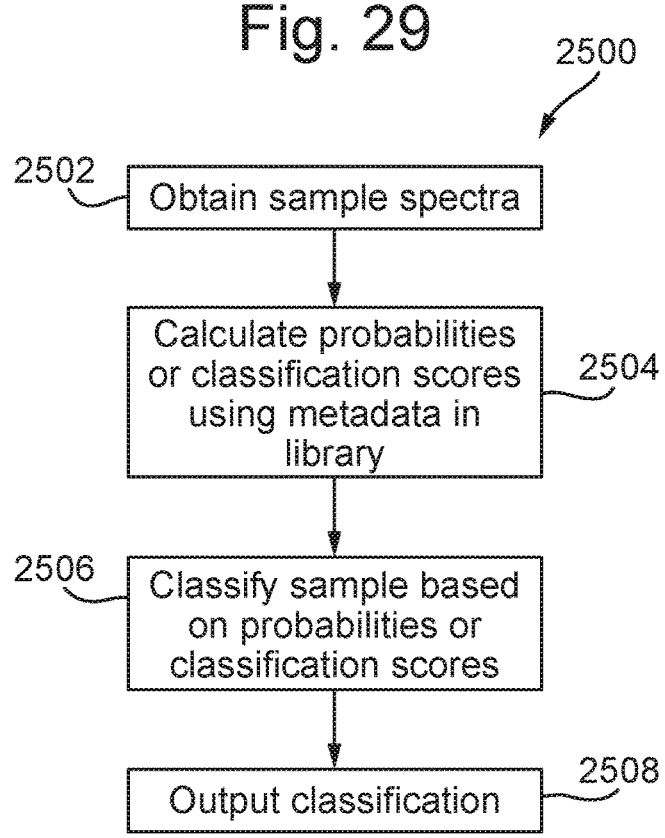
FIG. 29 shows a method of analysis that comprises using a classification library according to various embodiments.

FIG. 29 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y \mid \mu, D) = \prod_{i=1}^{N_{chan}} Pr(y_i \mid \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class $\tilde{s}$ is given by:

$$Pr(\tilde{s} \mid y) = \frac{L_{\tilde{s}}^{(1/F)}}{\sum_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Methods of Medical Treatment, Surgery and Diagnosis and Non-Medical Methods

Various different embodiments are contemplated. According to some embodiments the methods disclosed above may be performed on in vivo, ex vivo or in vitro tissue. The tissue may comprise human or non-human animal tissue. Embodiments are contemplated wherein the target may comprise biological tissue, a bacterial or fungal colony or more generally an organic target such as a plastic).

Various embodiments are contemplated wherein analyte ions generated by an ambient ionisation ion source are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers, ion analysers, mass analysing, mass spectrometric data, mass spectrometers and other related terms referring to apparatus and methods for determining the mass or mass to charge of ions e.g. analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometry-ion mobility (MS-IMS) embodiments are contemplated wherein both the ion mobility and mass to charge ratio of analyte ions generated e.g. by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

In any of the aspects or embodiments disclosed herein, the ion analyser or mass spectrometer (and/or ion mobility spectrometer) disclosed may obtain data in negative ion mode only, positive ion mode only, or in both positive and negative ion modes. Positive ion mode spectrometric data may be combined with negative ion mode spectrometric data. Ion mobility spectrometric data may be obtained using different ion mobility drift gases. This data may then be combined.

Various surgical, therapeutic, medical treatment and diagnostic methods are contemplated.

However, other embodiments are contemplated which relate to non-surgical and non-therapeutic methods of mass spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

Although the present invention has been described with reference to preferred embodiments, it will be understood by those skilled in the art that various changes in form and detail may be made without departing from the scope of the invention as set forth in the accompanying claims.

The invention claimed is:

1. An apparatus comprising:
a first device for generating aerosol, smoke or vapour from one or more regions of a target;
an inlet conduit to an ion analyser or mass spectrometer, said inlet conduit having an inlet through which said aerosol, smoke or vapour passes;
a Venturi pump arrangement arranged and adapted to direct said aerosol, smoke or vapour towards said inlet, wherein said Venturi pump arrangement is arranged and adapted to direct said aerosol, smoke or vapour onto a deflection device or surface prior to said aerosol, smoke or vapour passing through said inlet, wherein said deflection device comprises a hollow member having a first side and a second side, wherein the first side is solid and the second side comprises one or more apertures arranged and adapted to allow said aerosol, smoke or vapour to pass therethrough and wherein said Venturi pump arrangement is arranged and adapted to direct said aerosol, smoke or vapour onto the first surface of said deflection device;
a matrix conduit for introducing and mixing a matrix with said aerosol, smoke or vapour prior to said aerosol, smoke or vapour passing through the inlet; and
a collision surface located within a vacuum chamber and arranged and adapted such that said aerosol, smoke or vapour is caused to impact upon said collision surface so as to generate a plurality of analyte ions.

2. The apparatus as claimed in claim 1, wherein said one or more apertures are in fluid communication with a cavity or passage within said hollow member, and said inlet is in fluid communication with said cavity or passage.

3. The apparatus as claimed in claim 1, wherein said matrix conduit is in fluid communication with said cavity or passage.

4. The apparatus as claimed in claim 1, wherein said matrix conduit and/or said inlet conduit and/or said cavity or passage are aligned substantially co-axially with one another.

5. The apparatus as claimed in claim 1, wherein said Venturi pump arrangement comprises an elongated portion having an outlet through which said aerosol, smoke or vapour passes, and said elongated portion has a longitudinal axis that is perpendicular, or substantially perpendicular to a longitudinal axis of said cavity or passage and/or said inlet conduit and/or said matrix conduit.

6. The apparatus as claimed in claim 1, wherein said first device comprises an ambient ion source.

7. The apparatus as claimed in claim 1, wherein said first device comprises an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) probe electrospray ionisation ("PESI") ion source; (xix) a solid-probe assisted electrospray ionisation ("SPA-ESI") ion source; (xx) a cavitron ultrasonic surgical aspirator ("CUSA") ion source; (xxi) a focussed or unfocussed ultrasonic ablation ion source; (xxii) a microwave resonance ion source; and (xxiii) a pulsed plasma RF dissection device.

8. The apparatus as claimed in claim 1, wherein said first device comprises a laser source for irradiating said target with laser light to generate said aerosol, smoke or vapour.

9. The apparatus as claimed in claim 1, wherein said matrix comprises polar molecules, water, one or more alcohols, methanol, ethanol, isopropanol, acetone or acetonitrile.

10. The apparatus as claimed in claim 1, further comprising a mass analyser and/or ion mobility analyser arranged and adapted to mass analyse and/or ion mobility analyse said analyte ions in order to obtain mass spectrometric and/or ion mobility data.

11. A method comprising:
generating aerosol, smoke or vapour from one or more regions of a target;
providing an inlet conduit to an ion analyser or mass spectrometer, said inlet conduit having an inlet through which said aerosol, smoke or vapour passes;
using a Venturi pump arrangement to direct said aerosol, smoke or vapour towards said inlet, wherein said Venturi pump arrangement directs said aerosol, smoke or vapour onto a deflection device or surface prior to said aerosol, smoke or vapour passing through said inlet, wherein said deflection device comprises a hollow member having a first side and a second side, wherein the first side is solid and the second side comprises one or more apertures arranged and adapted to allow said aerosol, smoke or vapour to pass therethrough and wherein said Venturi pump arrangement is arranged and adapted to direct said aerosol, smoke or vapour onto the first surface of said deflection device;
introducing and mixing a matrix with said aerosol, smoke or vapour prior to said aerosol, smoke or vapour passing through the inlet; and
providing a collision surface located within a vacuum chamber such that said aerosol, smoke or vapour impacts upon said collision surface so as to generate a plurality of analyte ions.

12. The method as claimed in claim 11, wherein said first device comprises an ambient ion source.

13. The method as claimed in claim 11, wherein said first device comprises an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) probe electrospray ionisation ("PESI") ion source; (xix) a solid-probe assisted electrospray ionisation ("SPA-ESI") ion source; (xx) a cavitron ultrasonic surgical aspirator ("CUSA") ion source; (xxi) a focussed or unfocussed ultrasonic ablation ion source; (xxii) a microwave resonance ion source; and (xxiii) a pulsed plasma RF dissection device.

14. The method as claimed in claim 11, further comprising irradiating said target with laser light to generate said aerosol, smoke or vapour.

15. The method as claimed in claim 11, wherein said matrix comprises polar molecules, water, one or more alcohols, methanol, ethanol, isopropanol, acetone or acetonitrile.

16. The method as claimed in claim 11, further comprising mass analysing and/or ion mobility analysing said analyte ions in order to obtain mass spectrometric and/or ion mobility data.

* * * * *